United States Patent
Klun et al.

(10) Patent No.: US 11,945,900 B2
(45) Date of Patent: *Apr. 2, 2024

(54) ORTHODONTIC ARTICLES PREPARED USING A POLYCARBONATE DIOL, POLYMERIZABLE COMPOSITIONS, AND METHODS OF MAKING THE ARTICLES

(71) Applicant: Solventum Intellectual Properties Company, Maplewood, MN (US)

(72) Inventors: Thomas P. Klun, Lakeland, MN (US); Zeba Parkar, Marietta, GA (US); John M. Riedesel, San Jose, CA (US); Richard J. Pokorny, Maplewood, MN (US); Chad M. Amb, Roberts, WI (US); Benjamin R. Coonce, South St. Paul, MN (US); Robert S. Clough, St. Paul, MN (US); Tianyu Wu, St. Paul, MN (US); Saswata Chakraborty, Cottage Grove, MN (US); Yongshang Lu, Woodbury, MN (US); Benjamin C. MacMurray, St. Paul, MN (US); Ahmed S. Abuelyaman, Woodbury, MN (US); Karl J. L. Geisler, St. Paul, MN (US); Jodi L. Connell, St. Paul, MN (US); Ta-Hua Yu, Woodbury, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 622 days.

This patent is subject to a terminal disclaimer.

(21) Appl. No.: 17/052,221

(22) PCT Filed: Jun. 27, 2019

(86) PCT No.: PCT/IB2019/055455
§ 371 (c)(1),
(2) Date: Nov. 2, 2020

(87) PCT Pub. No.: WO2020/003197
PCT Pub. Date: Jan. 2, 2020

(65) Prior Publication Data
US 2021/0171701 A1    Jun. 10, 2021

Related U.S. Application Data

(63) Continuation-in-part of application No. PCT/US2019/033252, filed on May 21, 2019, and a
(Continued)

(51) Int. Cl.
*C08G 18/44* (2006.01)
*A61C 7/00* (2006.01)
(Continued)

(52) U.S. Cl.
CPC .............. *C08G 18/44* (2013.01); *A61C 7/002* (2013.01); *A61C 7/08* (2013.01); *A61C 13/0019* (2013.01); *B29C 71/0009* (2013.01); *B29C 71/02* (2013.01); *B29C 71/04* (2013.01); *B33Y 10/00* (2014.12); *B33Y 40/20* (2020.01); *B33Y 70/00* (2014.12); *B33Y 80/00* (2014.12); *C08G 18/222* (2013.01); *C08G 18/227* (2013.01); *C08G 18/242* (2013.01); *C08G 18/3206* (2013.01);
(Continued)

(58) Field of Classification Search
CPC .... C08G 18/44; C08G 18/222; C08G 18/227; C08G 18/242; B29C 71/04; B29C 71/02
See application file for complete search history.

(56) References Cited

U.S. PATENT DOCUMENTS 3,429,722 A   2/1969   Economy
3,795,524 A   3/1974   Sowman
(Continued)

FOREIGN PATENT DOCUMENTS

CA    1139486     1/1983
CN   104765251    7/2015
(Continued)

OTHER PUBLICATIONS

Database WPI Week 201779 Thomson Scientific, London An 2017-71365U XP002797229, 1 page.
(Continued)

*Primary Examiner* — Michael L Leonard
(74) *Attorney, Agent, or Firm* — Adrian L. Pishko

(57) ABSTRACT

The present disclosure provides an orthodontic article including the reaction product of the polymerizable composition. Further, the present disclosure provides polymerizable compositions and methods of making an orthodontic article. The method includes obtaining a polymerizable composition and selectively curing the polymerizable composition to form an orthodontic article. Further, methods are provided, including receiving, by a manufacturing device having one or more processors, a digital object comprising data specifying an orthodontic article; and generating, with the manufacturing device by an additive manufacturing process, the orthodontic article based on the digital object. A system is also provided, including a display that displays a 3D model of an orthodontic article; and one or more processors that, in response to the 3D model selected by a user, cause a 3D printer to create a physical object of an orthodontic article.

24 Claims, 8 Drawing Sheets

Related U.S. Application Data continuation-in-part of application No. PCT/US2019/033241, filed on May 21, 2019, and a continuation-in-part of application No. PCT/US2018/062074, filed on Nov. 20, 2018, and a continuation-in-part of application No. PCT/US2018/062085, filed on Nov. 20, 2018.

(60) Provisional application No. 62/850,638, filed on May 21, 2019, provisional application No. 62/798,083, filed on Jan. 29, 2019, provisional application No. 62/769,434, filed on Nov. 19, 2018, provisional application No. 62/769,375, filed on Nov. 19, 2018, provisional application No. 62/769,305, filed on Nov. 19, 2018, provisional application No. 62/769,421, filed on Nov. 19, 2018, provisional application No. 62/736,031, filed on Sep. 25, 2018, provisional application No. 62/736,027, filed on Sep. 25, 2018, provisional application No. 62/692,466, filed on Jun. 29, 2018, provisional application No. 62/692,456, filed on Jun. 29, 2018.

(51) Int. Cl.

| | | |
|---|---|---|
| *A61C 7/08* | (2006.01) | |
| *A61C 13/00* | (2006.01) | |
| *B29C 71/00* | (2006.01) | |
| *B29C 71/02* | (2006.01) | |
| *B29C 71/04* | (2006.01) | |
| *B33Y 10/00* | (2015.01) | |
| *B33Y 40/20* | (2020.01) | |
| *B33Y 70/00* | (2020.01) | |
| *B33Y 80/00* | (2015.01) | |
| *C08G 18/22* | (2006.01) | |
| *C08G 18/24* | (2006.01) | |
| *C08G 18/32* | (2006.01) | |
| *C08G 64/30* | (2006.01) | |
| *C08K 5/00* | (2006.01) | |
| *C08K 5/3437* | (2006.01) | |
| *B33Y 30/00* | (2015.01) | |

(52) U.S. Cl.
CPC .......... *C08G 64/305* (2013.01); *C08K 5/0041* (2013.01); *C08K 5/3437* (2013.01); *B29C 2071/0027* (2013.01); *B33Y 30/00* (2014.12); *C08G 2650/16* (2013.01)

(56) References Cited

U.S. PATENT DOCUMENTS

| | | | |
|---|---|---|---|
| 4,047,965 A | 9/1977 | Karst | |
| 4,255,243 A | 3/1981 | Coqueugniot | |
| 4,264,752 A | 4/1981 | Watson, Jr. | |
| 4,578,504 A | 3/1986 | Hammar | |
| 4,591,626 A | 5/1986 | Kawai | |
| 4,954,462 A | 9/1990 | Wood | |
| 5,185,299 A | 2/1993 | Wood | |
| 5,317,074 A | 5/1994 | Hammar | |
| 5,341,799 A | 8/1994 | Fifield | |
| 5,476,749 A | 12/1995 | Steinmann | |
| 5,512,611 A | 4/1996 | Mitra | |
| 5,780,154 A | 7/1998 | Okano | |
| 5,849,270 A | 12/1998 | Podszun | |
| 5,981,621 A | 11/1999 | Clark | |
| 6,183,593 B1 | 2/2001 | Narang | |
| 6,200,732 B1 | 3/2001 | Tamura | |
| 6,379,866 B2 | 4/2002 | Lawton | |
| 8,044,235 B2 | 10/2011 | Nozawa | |
| 9,200,108 B2 | 12/2015 | Bruchmann | |
| 9,205,601 B2 | 12/2015 | DeSimone | |
| 9,360,757 B2 | 6/2016 | DeSimone | |
| 2006/0204452 A1 | 9/2006 | Velamakanni | |
| 2006/0205838 A1 | 9/2006 | Velamakanni | |
| 2007/0031791 A1 | 2/2007 | Cinader, Jr. | |
| 2008/0248442 A1 | 10/2008 | Raby | |
| 2010/0233514 A1 | 9/2010 | Umezawa | |
| 2011/0091832 A1 | 4/2011 | Kim | |
| 2013/0095446 A1 | 4/2013 | Andreiko | |
| 2014/0356799 A1 | 12/2014 | Cinader, Jr. | |
| 2015/0072083 A1* | 3/2015 | Nebioglu | C09D 5/008 427/520 |
| 2016/0184189 A1 | 6/2016 | Hagiwara | |
| 2016/0332367 A1* | 11/2016 | Sun | B33Y 70/10 |
| 2017/0007362 A1 | 1/2017 | Chen | |
| 2017/0158803 A1 | 6/2017 | Amin | |
| 2018/0062074 A1 | 3/2018 | Sung | |
| 2018/0062085 A1 | 3/2018 | Bergmann | |
| 2018/0110683 A1 | 4/2018 | Yoshinaga | |
| 2019/0083208 A1 | 3/2019 | Hansen | |

FOREIGN PATENT DOCUMENTS

| | | |
|---|---|---|
| EP | 3466999 | 4/2019 |
| JP | H08-188630 | 7/1996 |
| JP | H09-216924 | 8/1997 |
| JP | 3115792 | 12/2000 |
| JP | 3301447 | 7/2002 |
| JP | 2004-217809 | 8/2004 |
| JP | 2010-043194 | 2/2010 |
| JP | 4526056 | 6/2010 |
| JP | 4682544 | 2/2011 |
| JP | 4880248 | 12/2011 |
| JP | 5055764 | 8/2012 |
| JP | 5068513 | 8/2012 |
| JP | 2012-184385 | 9/2012 |
| JP | 5224965 | 3/2013 |
| JP | 5445215 | 1/2014 |
| JP | 2014-114444 | 6/2014 |
| JP | 2014-116295 | 6/2014 |
| JP | 2016-112824 | 6/2016 |
| JP | 2017-048288 | 3/2017 |
| JP | 2017-210579 | 11/2017 |
| KR | 2017-0111640 | 10/2017 |
| WO | WO 1991-003503 | 3/1991 |
| WO | WO 1998-021157 | 5/1998 |
| WO | WO 2007-129704 | 11/2007 |
| WO | WO 2009-045752 | 4/2009 |
| WO | WO 2012-045660 | 4/2012 |
| WO | WO 2014-077688 | 5/2014 |
| WO | WO 2015-094842 | 6/2015 |
| WO | WO 2016-094272 | 6/2016 |
| WO | WO 2016-109660 | 7/2016 |
| WO | WO 2016-148960 | 9/2016 |
| WO | WO 2016-149007 | 9/2016 |
| WO | WO 2016-182444 | 11/2016 |
| WO | WO 2017-208959 | 12/2017 |
| WO | WO 2018-005501 | 1/2018 |
| WO | WO 2018-119026 | 6/2018 |
| WO | WO 2019-023009 | 1/2019 |
| WO | WO 2019-103855 | 5/2019 |
| WO | WO 2019-104072 | 5/2019 |
| WO | WO 2019-104079 | 5/2019 |
| WO | WO 2019-175716 | 9/2019 |
| WO | WO 2020-005411 | 1/2020 |
| WO | WO 2020-005413 | 1/2020 |
| WO | WO 2020-104873 | 5/2020 |
| WO | WO 2020-141444 | 7/2020 |
| WO | WO 2020-157598 | 8/2020 |

OTHER PUBLICATIONS

Fang, "The influence of monobutyl itaconate and β-carboxyethyl acrylate on acrylic latex pressure sensitive adhesives", International Journal of Adhesion and Adhesives, Aug. 2018, vol. 84, pp. 387-393.

Fleischhaker, "Glass-Transition-, Melting-, and Decomposition Temperatures of Tailored Polyacrylates and Polymethacrylates: General

(56) References Cited

OTHER PUBLICATIONS

Trends and Structure-Property Relationships", Macromolecular Chemistry and Physics, Jun. 2014, vol. 215, No. 12, pp. 1192-1200.
Hopfinger, "Molecular Modeling of Polymers. IV. Estimation of Glass Transition Temperatures", Journal of Polymer Science: Part B: Polymer Physics, Sep. 1988, vol. 26, No. 10, pp. 2007-2028.
Jakubowski, "Comparison of thermomechanical properties of statistical, gradient and block copolymers of isobornyl acrylate and n-butyl acrylate with various acrylate homopolymers", Polymer, Mar. 2008, vol. 49, No. 06, pp. 1567-1578.
Krause, "Glass Temperatures of Some Acrylic Polymers", Journal of Polymer Science. Part A. General papers, Oct. 1965, vol. 3, No. 10, pp. 3573-3586.
Matsumoto, "Radical Polymerization of 4-*tert*-Butylcyclohexyl Methacrylate: Polymerization Kinetics and Polymer Properties", Macromolecules, Mar. 1993, vol. 26 No. 7, pp. 1659-1665.
Matsumoto, "Synthesis and Characterization of Poly(1-adamantyl methacrylate): Effects of the Adamantyl Group on Radical Polymerization Kinetics and Thermal Properties of the Polymer", Macromolecules, Jul. 1991, vol. 24, No. 14, pp. 4017-4024.
Matsumoto, "Synthesis and Thermal Properties of Poly (cycloalkyl methacrylate) s Bearing Bridged—and Fused-Ring Structures", Journal of Polymer Science: Part A Polymer Chemistry, Sep. 1993, vol. 31, No. 10, pp. 2531-2539.
"Methacrylate Resins", By E. I. du Pont de Nemours & Company, Inc., at the Ninety-second Meeting of the American Chemical Society at Pittsburgh, Pa., Industrial and Engineering Chemistry, Sep. 1936, vol. 28, No. 10, pp. 1160-1163.
"Methyl Methacrylate MMA", Product of Mitsubishi Chemical Corporation, XP055659748, <Retrieved from the Internet on Jan. 2020>, URL <https//www m-chemical co jp/en/products/departments/mcc/chemicals-dept/product/ 1201253 7952 html>, 3 pages.
Muñoz, "Effect of the side chain structure on the glass transition temperature: Part 4. Molecular weight dependence of $T_g$ in chalcogenides containing poly(methacrylates)", Thermochimica Acta, Jun. 1989, vol. 146, pp. 137-147.
Rogers, "Glass Formation in Polymers. I. The Glass Transitions of the Poly-(n-Alkyl Methacrylates)", The Journal of Physical Chemistry, Jul. 1957, vol. 61, No. 7, pp. 985-991.
Russell, "Thermal and Dynamic Mechanical Relaxation Behavior of Stereoregular Poly(2-Hydroxyethyl Methacrylate)", Journal of Polymer Science: Polymer Physics Edition, Jun. 1980, vol. 18, No. 06, pp. 1271-1283.
Song, "In Vitro Evaluation of Chemically Cross-Linked Shape-Memory Acrylate-Methacrylate Copolymer Networks as Ocular Implants", The Journal of Physical Chemistry B, Jun. 2010, vol. 114, No. 21, pp. 7172-7178.
Technical Data Catalog: "Specialty Monomers", BASF, 12pages.
Turner, "The glass transition temperature of poly(N-vinyl pyrrolidone) by differential scanning calorimetry", Polymer, May 1985, vol. 26, No. 5, pp. 757-762.
Wilson, "Thermal Expansion of Amorphous Polymers at Atmospheric Pressure. I. Experimental", Macromolecules, Nov. 1973, vol. 6, No. 6, pp. 902-908.
International Search Report for PCT International Application No. PCT/US2019/033241, dated Aug. 7, 2019, 5 pages.
International Search Report for PCT International Application No. PCT/US2019/033252, dated Aug. 20, 2019, 2 pages.
International Search Report for PCT International Application No. PCT/IB2019/055455, dated Mar. 30, 2020, 10 pages.

* cited by examiner

ORTHODONTIC ARTICLES PREPARED USING A POLYCARBONATE DIOL, POLYMERIZABLE COMPOSITIONS, AND METHODS OF MAKING THE ARTICLES

CROSS REFERENCE TO RELATED APPLICATIONS

This application is a national stage filing under 35 U.S.C. 371 of PCT/IB2019/055455, filed Jun. 27, 2019, which claims the benefit of U.S. Application No. 62/692,456, filed Jun. 29, 2018; U.S. Application No. 62/692,466, filed Jun. 29, 2018; U.S. Application No. 62/736,027, filed Sep. 25, 2018; U.S. Application No. 62/736,031, filed Sep. 25, 2018; U.S. Application No. 62/769,305, filed Nov. 19, 2018; U.S. Application No. 62/769,375, filed Nov. 19, 2018; U.S. Application No. 62/769,421, filed Nov. 19, 2018; U.S. Application No. 62/769,434, filed Nov. 19, 2018; PCT Application No. PCT/US2018/062074, filed Nov. 20, 2018; PCT Application No. PCT/US2018/062085, filed Nov. 20, 2018; U.S. Application No. 62/798,083, filed Jan. 29, 2019; U.S. Application No. 62/850,638, filed May 21, 2019; PCT Application No. PCT/US2019/033241, filed May 21, 2019; and PCT Application No. PCT/US2019/033252, filed May 21, 2019; the disclosures of which are incorporated by reference in their entireties herein.

TECHNICAL FIELD

The present disclosure broadly relates to orthodontic articles and methods of making the orthodontic articles, such as additive manufacturing methods.

BACKGROUND

The use of stereolithography and inkjet printing to produce three-dimensional articles has been known for a relatively long time, and these processes are generally known as methods of so called 3D printing (or additive manufacturing). In vat polymerization techniques (of which stereolithography is one type), the desired 3D article is built up from a liquid, curable composition with the aid of a recurring, alternating sequence of two steps: in the first step, a layer of the liquid, curable composition, one boundary of which is the surface of the composition, is cured with the aid of appropriate radiation within a surface region which corresponds to the desired cross-sectional area of the shaped article to be formed, at the height of this layer, and in the second step, the cured layer is covered with a new layer of the liquid, curable composition, and the sequence of steps is repeated until a so-called green body (i.e., gelled article) of the desired shape is finished. This green body is often not yet fully cured and must, usually, be subjected to post-curing. The mechanical strength of the green body immediately after curing, otherwise known as green strength, is relevant to further processing of the printed articles.

Other 3D printing techniques use inks that are jetted through a print head as a liquid to form various three-dimensional articles. In operation, the print head may deposit curable photopolymers in a layer-by-layer fashion. Some jet printers deposit a polymer in conjunction with a support material or a bonding agent. In some instances, the build material is solid at ambient temperatures and converts to liquid at elevated jetting temperatures. In other instances, the build material is liquid at ambient temperatures.

SUMMARY

Existing printable/polymerizable resins tend to be too brittle (e.g., low elongation, short-chain crosslinked bonds, thermoset composition, and/or high glass transition temperature) for a resilient oral appliance such as an aligner. An aligner or other appliance prepared from such resins could easily break in the patient's mouth during treatment, creating material fragments that may abrade or puncture exposed tissue or be swallowed. These fractures at the very least interrupt treatment and could have serious health consequences for the patient. Thus, there is a need for curable liquid resin compositions that are tailored and well suited for creation of resilient articles using 3D printing (e.g., additive manufacturing) method. Preferably, curable liquid resin compositions to be used in the vat polymerization 3D printing process have low viscosity, a proper curing rate, and excellent mechanical properties in the final cured article. In contrast, compositions for inkjet printing processes need to be much lower viscosity to be able to be jetted through nozzles, which is not the case for most vat polymerization resins.

In a first aspect, an orthodontic article is provided. The orthodontic article includes the reaction product of a polymerizable composition. The polymerizable composition includes 30-65 parts by weight of monofunctional (meth)acrylate monomer(s) and at least one urethane (meth)acrylate including polymerized units of an aliphatic polycarbonate diol. A cured homopolymer of at least one monofunctional (meth)acrylate monomer has a $T_g$ of 30 degrees Celsius (° C.) or greater. The reaction product of the polymerizable composition has a shape of the orthodontic article.

In a second aspect, a polymerizable composition is provided. The polymerizable composition includes 30-65 parts by weight of monofunctional (meth)acrylate monomer(s) and at least one urethane (meth)acrylate including polymerized units of an aliphatic polycarbonate diol. A cured homopolymer of at least one monofunctional (meth)acrylate monomer has a $T_g$ of 30° C. or greater.

In a third aspect, a method of making an orthodontic article is provided. The method includes a) obtaining a photopolymerizable composition (e.g., the polymerizable composition according to the second aspect); b) selectively curing the photopolymerizable composition; and c) repeating steps a) and b) to form multiple layers and create the orthodontic article.

In a fourth aspect, a non-transitory machine readable medium is provided. The non-transitory machine readable medium includes data representing a three-dimensional model of an orthodontic article, when accessed by one or more processors interfacing with a 3D printer, causes the 3D printer to create an orthodontic article comprising a reaction product of a photopolymerizable composition (e.g., the polymerizable composition according to the second aspect).

In a fifth aspect, a method is provided. The method includes a) retrieving, from a non-transitory machine readable medium, data representing a 3D model of an article; b) executing, by one or more processors, a 3D printing application interfacing with a manufacturing device using the data; and c) generating, by the manufacturing device, a physical object of the orthodontic article. The orthodontic article includes a reaction product of a photopolymerizable composition (e.g., the polymerizable composition according to the second aspect).

In a sixth aspect, another method is provided. The method includes a) receiving, by a manufacturing device having one or more processors, a digital object comprising data specifying a plurality of layers of an orthodontic article; and b) generating, with the manufacturing device by an additive manufacturing process, the orthodontic article based on the digital object. The orthodontic article includes a reaction product of a photopolymerizable composition (e.g., the polymerizable composition according to the second aspect).

In a seventh aspect, a system is provided. The system includes a) a display that displays a 3D model of an orthodontic article; and b) one or more processors that, in response to the 3D model selected by a user, cause a 3D printer to create a physical object of an orthodontic article. The orthodontic article includes a reaction product of a photopolymerizable composition (e.g., the polymerizable composition according to the second aspect).

Clear tray aligners (e.g., orthodontic alignment trays) and tensile bars made according to at least certain embodiments of this disclosure were found to show low brittleness, good resistance to water, and good toughness.

The above summary of the present disclosure is not intended to describe each disclosed embodiment or every implementation of the present disclosure. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

Figure 1:
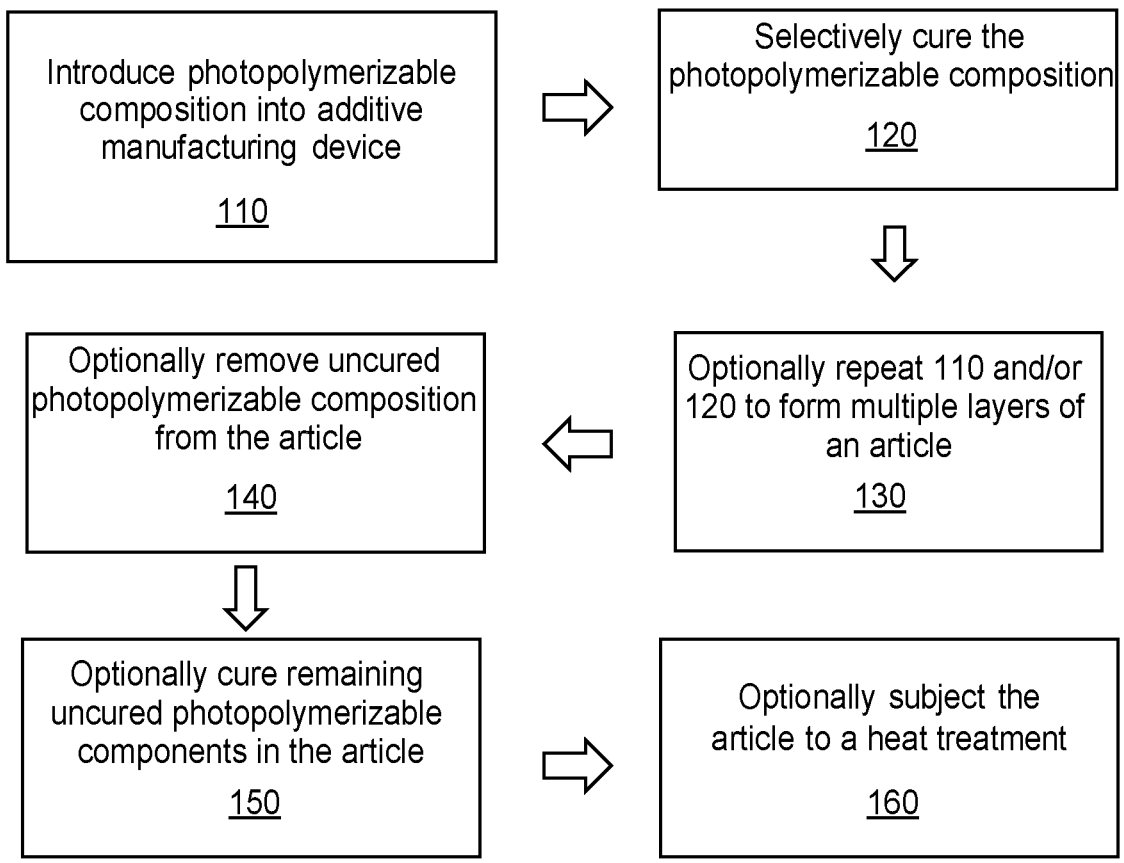
FIG. 1 is a flowchart of a process for building an article using photopolymerizable compositions disclosed herein.

While the above-identified figures set forth several embodiments of the disclosure other embodiments are also contemplated, as noted in the description. The figures are not necessarily drawn to scale. In all cases, this disclosure presents the invention by way of representation and not limitation. It should be understood that numerous other modifications and embodiments can be devised by those skilled in the art, which fall within the scope and spirit of the principles of the invention.

DETAILED DESCRIPTION OF ILLUSTRATIVE EMBODIMENTS

As used herein, "aliphatic group" means a saturated or unsaturated linear, branched, or cyclic hydrocarbon group. This term is used to encompass alkyl, alkenyl, and alkynyl groups, for example.

As used herein, "alkyl" means a linear or branched, cyclic or acyclic, saturated monovalent hydrocarbon having from one to thirty-two carbon atoms, e.g., methyl, ethyl, 1-propyl, 2-propyl, pentyl, and the like.

As used herein, "alkylene" means a linear saturated divalent hydrocarbon having from one to twelve carbon atoms or a branched saturated divalent hydrocarbon radical having from three to twelve carbon atoms, e.g., methylene, ethylene, propylene, 2-methylpropylene, pentylene, hexylene, and the like.

As used herein, "alkenyl" refers to a monovalent linear or branched unsaturated aliphatic group with one or more carbon-carbon double bonds, e.g., vinyl. Unless otherwise indicated, the alkenyl groups typically contain from one to twenty carbon atoms.

As used herein, the term "arylene" refers to a divalent group that is carbocyclic and aromatic. The group has one to five rings that are connected, fused, or combinations thereof. The other rings can be aromatic, non-aromatic, or combinations thereof. In some embodiments, the arylene group has up to 5 rings, up to 4 rings, up to 3 rings, up to 2 rings, or one aromatic ring. For example, the arylene group can be phenylene.

As used herein, "aralkylene" refers to a divalent group that is an alkylene group substituted with an aryl group or an alkylene group attached to an arylene group. The term "alkarylene" refers to a divalent group that is an arylene group substituted with an alkyl group or an arylene group attached to an alkylene group. Unless otherwise indicated, for both groups, the alkyl or alkylene portion typically has from 1 to 20 carbon atoms, 1 to 10 carbon atoms, 1 to 6 carbon atoms, or 1 to 4 carbon atoms. Unless otherwise indicated, for both groups, the aryl or arylene portion typically has from 6 to 20 carbon atoms, 6 to 18 carbon atoms, 6 to 16 carbon atoms, 6 to 12 carbon atoms, or 6 to 10 carbon atoms.

As used herein, the term "essentially free" in the context of a composition being essentially free of a component, refers to a composition containing less than 1% by weight (wt. %), 0.5 wt. % or less, 0.25 wt. % or less, 0.1 wt. % or less, 0.05 wt. % or less, 0.001 wt. % or less, or 0.0001 wt. % or less of the component, based on the total weight of the composition.

As used herein, the term "glass transition temperature" ($T_g$), of a polymer refers to the transition of a polymer from a glassy state to a rubbery state and can be measured using Differential Scanning Calorimetry (DSC), such as at a heating rate of 10° C. per minute in a nitrogen stream. When the $T_g$ of a monomer is mentioned, it is the $T_g$ of a homopolymer of that monomer. The homopolymer must be sufficiently high molecular weight such that the $T_g$ reaches a limiting value, as it is generally appreciated that a $T_g$ of a homopolymer will increase with increasing molecular weight to a limiting value. The homopolymer is also understood to be substantially free of moisture, residual monomer, solvents, and other contaminants that may affect the $T_g$. A suitable DSC method and mode of analysis is as described in Matsumoto, A. et. al., J. Polym. Sci. A., Polym. Chem. 1993, 31, 2531-2539.

As used herein, the terms "hardenable" refers to a material that can be cured or solidified, e.g., by heating to remove solvent, heating to cause polymerization, chemical cross-linking, radiation-induced polymerization or crosslinking, or the like.

As used herein, "curing" means the hardening or partial hardening of a composition by any mechanism, e.g., by heat, light, radiation, e-beam, microwave, chemical reaction, or combinations thereof.

As used herein, "cured" refers to a material or composition that has been hardened or partially hardened (e.g., polymerized or crosslinked) by curing.

As used herein, "integral" refers to being made at the same time or being incapable of being separated without damaging one or more of the (integral) parts.

As used herein, the term "(meth)acrylate" is a shorthand reference to acrylate, methacrylate, or combinations thereof, "(meth)acrylic" is a shorthand reference to acrylic, methacrylic, or combinations thereof, and "(meth)acryl" is a shorthand reference to acryl and methacryl groups. "Acryl" refers to derivatives of acrylic acid, such as acrylates, methacrylates, acrylamides, and methacrylamides. By "(meth)acryl" is meant a monomer or oligomer having at least one acryl or methacryl groups, and linked by an aliphatic segment if containing two or more groups. As used herein, "(meth)acrylate-functional compounds" are compounds that include, among other things, a (meth)acrylate moiety.

As used herein, "polymerizable composition" means a hardenable composition that can undergo polymerization upon initiation (e.g., free-radical polymerization initiation). Typically, prior to polymerization (e.g., hardening), the polymerizable composition has a viscosity profile consistent with the requirements and parameters of one or more 3D printing systems. In some embodiments, for instance, hardening comprises irradiating with actinic radiation having sufficient energy to initiate a polymerization or cross-linking reaction. For instance, in some embodiments, ultraviolet (UV) radiation, e-beam radiation, or both, can be used. When actinic radiation can be used, the polymerizable composition is referred to as a "photopolymerizable composition".

As used herein, a "resin" contains all polymerizable components (monomers, oligomers and/or polymers) being present in a hardenable composition. The resin may contain only one polymerizable component compound or a mixture of different polymerizable compounds.

As used herein, the "residue of a diisocyanate", is the structure of the diisocyanate after the —NCO groups are removed. For example, 1,6-hexamethylene diisocyanate has the structure $OCN-(CH_2)_6-NCO$, and its residue, $R_{di}$, after removal of the isocyanate groups is $-(CH_2)_6-$.

As used herein, the "residue of a polycarbonate polyol", is the structure of the polycarbonate polyol after the —OH groups are removed. For example, a polycarbonate diol having the structure $H(O-R_1-O-C(=O))_m-O-R_2-OH$, has a residue, (e.g., $R_{dOH}$, $R_{dOH1}$, or $R_{dOH2}$) after removal of the end —OH groups, of $-R_1-O-C(=O)-(O-R_1-O-C(=O))_{m-1}-R_2-$, wherein each $R_1$ in each repeat unit and $R_2$ is independently an aliphatic, cycloaliphatic, or aliphatic/cycloaliphatic alkylene group and m is 2 to 23. Examples of $R_1$ and $R_2$ groups include $-CH_2-CH_2-CH(CH_3)-CH_2-CH_2-$, $-CH_2-C(CH_3)_2-CH_2-$, $-(CH_2)_6-$, $-(CH_2)_9-$, and $-(CH_2)_{10}-$.

As used herein, the "residue of a (meth)acrylated diol" is the structure of the (meth)acrylated diol after the —OH groups are removed. For example, a (meth)acrylated diol having the structure HO-Q(A)-OH has a residue, $R_{AD}$, after removal of the end —OH groups, of $-Q_1(A)-$, wherein $Q_1$ is a straight or branched chain or cycle-containing aliphatic polyvalent connecting group and A is a (meth)acryl functional group of the formula $-XC(=O)C(R)=CH_2$, wherein X is O, S, or $NR_4$, $R_4$ is H or alkyl of 1 to 4 carbon atoms, and $R_1$ is a lower alkyl of 1 to 4 carbon atoms or H. An example of a methacrylated diol is

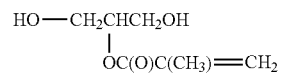

and an example of $R_{AD}$ is

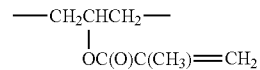

As used herein, the "residue of a polyester polyol" is the structure of the polyester polyol after the —OH groups are removed. For example, a polyester polyol having the structure $H[O-R_3-O-C(=O)-R_4-C(=O)]_{m1}-O-R_3-OH$, has a residue, (e.g., $R_{dOH2}$ or $R_{dOH3}$) after removal of the end —OH groups, of $-R_3-O-C(=O)-R_4-C(=O)-[O-R_3-O-C(=O)-R_4-C(=O)]_{m1-1}-O-R_3-$, wherein $R_3$ and R are independently straight or branched chain or cycle-containing alkylene, groups, that optionally include heteroatoms, such as oxygen. $R_3$ and $R_4$ independently comprise 2 to 40 carbon atoms. The subscript "m1" is typically at least 2, 3, 4, 5, 6, or 7.

As used herein, "thermoplastic" refers to a polymer that flows when heated sufficiently above its glass transition point and become solid when cooled.

As used herein, "thermoset" refers to a polymer that permanently sets upon curing and does not flow upon subsequent heating. Thermoset polymers are typically cross-linked polymers.

As used herein, "occlusal" means in a direction toward the outer tips of the patient's teeth; "facial" means in a direction toward the patient's lips or cheeks; and "lingual" means in a direction toward the patient's tongue.

The words "preferred" and "preferably" refer to embodiments of the disclosure that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the disclosure.

In this application, terms such as "a", "an", and "the" are not intended to refer to only a singular entity, but include the general class of which a specific example may be used for illustration. The terms "a", "an", and "the" are used interchangeably with the term "at least one." The phrases "at least one of" and "comprises at least one of" followed by a list refers to any one of the items in the list and any combination of two or more items in the list.

As used herein, the term "or" is generally employed in its usual sense including "and/or" unless the content clearly dictates otherwise.

The term "and/or" means one or all of the listed elements or a combination of any two or more of the listed elements.

Also herein, all numbers are assumed to be modified by the term "about" and preferably by the term "exactly." As used herein in connection with a measured quantity, the term "about" refers to that variation in the measured quantity as would be expected by the skilled artisan making the measurement and exercising a level of care commensurate with the objective of the measurement and the precision of the measuring equipment used. Also herein, the recitations of numerical ranges by endpoints include all numbers subsumed within that range as well as the endpoints (e.g., 1 to 5 includes 1, 1.5, 2, 2.75, 3, 3.80, 4, 5, etc.).

As used herein as a modifier to a property or attribute, the term "generally", unless otherwise specifically defined, means that the property or attribute would be readily recognizable by a person of ordinary skill but without requiring absolute precision or a perfect match (e.g., within +/−20% for quantifiable properties). The term "substantially", unless otherwise specifically defined, means to a high degree of approximation (e.g., within +/−10% for quantifiable properties) but again without requiring absolute precision or a perfect match. Terms such as same, equal, uniform, constant, strictly, and the like, are understood to be within the usual tolerances or measuring error applicable to the particular circumstance rather than requiring absolute precision or a perfect match.

In a first aspect, the present disclosure provides an orthodontic article. The orthodontic article comprises the reaction product of a polymerizable composition comprising:

30-65 parts by weight of monofunctional (meth)acrylate monomer(s), wherein a cured homopolymer of at least one monofunctional (meth)acrylate monomer has a $T_g$ of 30 degrees Celsius (° C.) or greater; and at least one urethane (meth)acrylate comprising polymerized units of an aliphatic polycarbonate diol.

In a second aspect, the present disclosure provides a polymerizable composition. The polymerizable composition comprises:

30-65 parts by weight of monofunctional (meth)acrylate monomer(s), wherein a cured homopolymer of at least one monofunctional (meth)acrylate monomer has a $T_g$ of 30 degrees Celsius (° C.) or greater; and at least one urethane (meth)acrylate comprising polymerized units of an aliphatic polycarbonate diol.

The monofunctional (meth)acrylate monomer(s) and urethane (meth)acrylates are discussed in detail below.

Monofunctional (Meth)Acrylate Monomer

In any embodiment, the polymerizable composition comprises a monofunctional (meth)acrylate monomer having a glass transition temperature ($T_g$), i.e., whose cured homopolymer has a $T_g$ of 30° C. or greater. In some embodiments, a monofunctional (meth)acrylate monomer is present whose cured homopolymer has a $T_g$ of 40° C. or greater, 50° C. or greater, 60° C. or greater, 70° C. or greater, 80° C. or greater, 90° C. or greater, 100° C. or greater, 110° C. or greater, 120° C. or greater, 125° C. or greater, 130° C. or greater, 135° C. or greater, 140° C. or greater, 145° C. or greater, 150° C. or greater, 155° C. or greater, 160° C. or greater, 165° C. or greater, 170° C. or greater, 175° C. or greater, 180° C. or greater, 185° C. or greater, 190° C. or greater, or even 195° C. or greater. In select embodiments, a monofunctional (meth)acrylate monomer is present whose cured homopolymer has a $T_g$ of 150° C. or greater, 170° C. or greater, or 180° C. or greater. The $T_g$ of the homopolymer of the monofunctional (meth)acrylate monomer is typically no greater than about 260° C. For example, 1-adamantyl methacrylate decomposes at about 260° C. In some embodiments, the $T_g$ of the homopolymer of the monofunctional (meth)acrylate monomer is no greater than 255° C., 250° C., 245° C., 240° C., 235° C., 230° C., 225° C., 220° C., 215° C., 210° C., 205° C. or 200° C. The inclusion of one or more monofunctional (meth)acrylate monomers whose cured homopolymer has a $T_g$ of 90° C. or greater in a polymerizable composition contributes to increasing the relaxation modulus of a polymerization reaction product of the composition as measured after soaking in deionized water. Often, the $T_g$ of a homopolymer of a monomer can be found in the literature, such as in Table 1 below. Table 1 includes the reported $T_g$ of the homopolymer of a number of monofunctional (meth)acrylate monomers and the literature source of the reported $T_g$.

In some embodiments, the monofunctional (meth)acrylate monomer comprises a cycloaliphatic monofunctional (meth)acrylate. Suitable monofunctional (meth)acrylate monomers include for instance and without limitation, dicyclopentadienyl acrylate, dicyclopentanyl acrylate, dimethyl-1-adamantyl acrylate, cyclohexyl methacrylate, tetrahydrofurfuryl methacrylate, 2-phenoxyethyl methacrylate, butyl methacrylate (e.g., tert-butyl methacrylate or isobutyl methacrylate), benzyl methacrylate, n-propylmethacrylate, 3,3,5-trimethylcyclohexyl methacrylate, butylcyclohexylmethacrylate (e.g., cis-4-tert-butylcyclohexylmethacrylate, 73/27 trans/cis-4-tert-butylcyclohexylmethacrylate, or trans-4-tert-butylcyclohexyl methacrylate), 2-decahydronapthyl methacrylate, 1-adamantyl acrylate, dicyclopentadienyl methacrylate, dicyclopentanyl methacrylate, isobornyl methacrylate (e.g., d,l-isobornyl methacrylate), dimethyl-1-adamantyl methacrylate, bornyl methacrylate (e.g., d,l-bornyl methacrylate), 3-tetracyclo[4.4.0.1.1]dodecyl methacrylate, 1-adamantyl methacrylate, isobornyl acrylate, tertiary butyl acrylate, or combinations thereof. In an embodiment, the monofunctional (meth)acrylate monomer comprises isobornyl methacrylate.

In certain embodiments, the weight ratio of the monofunctional (meth)acrylate monomer to the polyurethane (meth)acrylate is 60:40 to 40:60, 55:45 to 45:55, or 50:50. In some embodiments, the urethane (meth)acrylate and the monofunctional (meth)acrylate monomer(s) are present at a weight ratio ranging from 2:1 to 1:2. Often, the monofunctional (meth)acrylate monomer is present in an amount of 40 parts or more by weight per 100 parts of the total polymerizable composition, 45 parts or more, 46 parts or more, 47 parts or more, 48 parts or more, 49 parts or more, or 50 parts or more; and 65 parts or less, 64 parts or less, 63 parts or less, 62 parts or less, 61 parts or less, 60 parts or less, 59 parts or less, 58 parts or less, 57 parts or less, 56 parts or less, or 55 parts or less, by weight per 100 parts of the total polymerizable composition. In some embodiments, the monofunctional (meth)acrylate monomer(s) having a $T_g$ of at least 30° C. are present in an amount of at least 15, 20, 25, 30, 35, 40, 45, or 50 wt. %, based on the total weight of the organic components of the composition (e.g., excluding inorganic components, such as filler).

In some embodiments of the invention, the cured material will be in contact with an aqueous environment. In those cases, it is advantageous to utilize materials which have low affinity for water. The affinity for water of certain (meth)acrylate monomers can be estimated by the calculation of a partition coefficient (P) between water and an immiscible solvent, such as octanol. This can serve as a quantitative descriptor of hydrophilicity or lipophilicity. The octanol/water partition coefficient can be calculated by software programs such as ACD ChemSketch, (Advanced Chemistry Development, Inc., Toronto, Canada) using the log of octanol/water partition coefficient (log P) module. In embodiments of the present invention, the calculated log P value is greater than 1, 1.5, 2, 2.5, 3, 3.5, or 4. The calculated log P value is typically no greater than 12.5. In some embodiments, the calculated log P value is no greater than 12, 11.5, 11, 10.5, 10, 9.5, 9, 8.5, 8, 7.5, 7, 6.5, 6, or 5.5. Moreover, in some embodiments, polymerizable compositions exclude the presence of a significant amount of hydrophilic (meth)

acrylate monomers by being essentially free of any monofunctional (meth)acrylate monomer having a log P value of less than 3, less than 2, or less than 1.

In some embodiments, polymerizable compositions contain hydrophilic (meth)acrylate monomers, oligomers, or polymers (e.g., hydrophilic urethane (meth)acrylate) having a log P value of less than 3, less than 2, or less than 1, in an amount of less than 30% by weight, based on the total weight of the polymerizable composition, such as 29% or less, 28%, 27%, 26%, 25%, 24%, 23%, 22%, 21%, 20%, 19%, 18%, 17%, 16%, 15%, 14%, 13%, 12%, or 11% or less of hydrophilic components; and 1% by weight or more, 2%, 3%, 4%, 5%, 7%, 9%, or 10% or more hydrophilic components, for example 1% to 29% by weight, based on the total weight of the polymerizable composition. In some embodiments, the combination of a hydrophilic component and a monofunctional (meth)acrylate monomer whose cured homopolymer has a $T_g$ of 150° C. or greater can impart advantageous properties to an article, for instance, 20% by weight or more of the high $T_g$ monomer, 22%, 25%, 27%, 30%, 32%, 35%, 37%, 40%, 42%, 45%, 47%, or 50% by weight or more of a monofunctional (meth)acrylate monomer whose cured homopolymer has a $T_g$ of 150° C. may be included when 1% to 29% by weight of a hydrophilic component is present, each based on the total weight of the polymerizable composition.

In embodiments of polymerizable compositions containing little to no low molecular weight difunctional component (e.g., a dimethacrylate), inclusion of an insufficient amount of a relatively high $T_g$ monomer (e.g., over 125° C., 140° C., 150° C., or over 160° C.), may negatively impact the ability of a polymerization reaction product of the polymerization composition to yield (e.g., having increased brittleness).

TABLE 1

Reported glass transition temperature ($T_g$) and calculated log P (log of octanol/water partition coefficient) of homopolymers of monofunctional (meth)acrylate monomers.

| Monomer | $T_g$ (° C.) | $T_g$ Reference | Calculated log P |
| --- | --- | --- | --- |
| 3,3,5-trimethylcyclohexyl acrylate | 15 | Hopfinger et. al.; J. Polym. Sci. B., Polym. Phys. 1988, 26, 2007 | 4.38 |
| d,l-isobornyl acrylate | 94 | Jakubowski et. al. Polymer, 2008, 49, 1567 | 4.22 |
| dicyclopentanyl acrylate | 103 | US 4,591,626 | 3.69 |
| 3,5-dimethyl-1-adamantyl acrylate | 105 | Matsumoto, A. et.al. Macromolecules 1991, 24, 4017 | 4.63 |
| cyclohexyl methacrylate | 107 | Wilson, P.S., Simha, R.; Macromolecules, 1973, 95, 3, 902 | 3.41 |
| tert-butyl methacrylate | 113 | Matsumoto, A. et.al. Macromolecules 1991, 24, 4017 | 2.57 |
| 3,3,5-trimethylcyclohexyl methacrylate | 125 | Hopfinger et. al.; J. Polym. Sci. B., Polym. Phys. 1988, 26, 2007 | 4.93 |
| cis-4-tert-butyl-cyclohexylmethacrylate | 132 | Matsumoto, A. et.al. Macromolecules 1993, 26, 7, 1659 | 5.13 |
| 2-decahydronapthyl methacrylate | 145 | Matsumoto, A. et. al., J. Polym. Sci. A., Polym. Chem. 1993, 31, 2531 | 4.95 |
| 1-adamantyl acrylate | 153 | Matsumoto, A. et.al. Macromolecules 1991, 24, 4017 | 3.68 |
| Mixture of 73% trans-4-tert-butylcyclohexylmethacrylate/27% cis-4-tert-butylcyclohexylmethacrylate | 163 | Matsumoto, A. et.al. Macromolecules 1993, 26, 7, 1659 | 5.13 |
| dicyclopentanyl methacrylate | 173 | US 4,591,626 | 4.24 |
| trans-4-tert-butylcyclohexyl methacrylate | 178 | Matsumoto, A. et.al. Macromolecules 1993, 26, 7, 1659 | 5.13 |
| d,l-isobornyl methacrylate | 191 | Matsumoto, A. et. al., J. Polym. Sci. A., Polym. Chem. 1993, 31, 2531 | 4.77 |
| 3,5-dimethyl-1-adamantyl methacrylate | 194 | Matsumoto, A. et.al. Macromolecules 1991, 24, 4017 | 5.19 |
| d,l-bornyl methacrylate | 194 | Matsumoto, A. et. al., J. Polym. Sci. A., Polym. Chem. 1993, 31, 2531 | 4.77 |
| 3-tetracyclo[4.4.0.1.1]dodecyl methacrylate | 199 | Matsumoto, A. et. al., J. Polym. Sci. A., Polym. Chem. 1993, 31, 2531 | 4.66 |

TABLE 1-continued

Reported glass transition temperature ($T_g$) and calculated log P (log of octanol/water partition coefficient) of homopolymers of monofunctional (meth)acrylate monomers.

| Monomer | $T_g$ (° C.) | $T_g$ Reference | Calculated log P |
|---|---|---|---|
| 1-adamantyl methacrylate | >253 | Matsumoto, A. et.al. Macromolecules 1991, 24, 4017 | 4.23 |
| 2-ethylhexyl methacrylate | −10 | Fleischhaker et. al., Macromol. Chem. Phys. 2014, 215, 1192. | 4.88 |
| tetrahydrofurfuryl methacrylate | 60 | E.I. du Pont de Nemours & Co., Ind. Eng. Chem., 1936, 28, 1160, | 1.38 |
| 2-phenoxyethyl methacrylate | 47 | Song et. al.; J. Phys. Chem. B 2010, 114, 7172 | 3.26 |
| N-vinyl pyrrolidone | 180 | Turner et. al; Polymer, 1985, 26, 757 | 0.37 |
| carboxyethyl acrylate | <30 | Fang et. al.; Int. J. Adhes. andAdhes. 84 (2018) 387-393 | 0.60 |
| 2-hydroxyethyl methacrylate | 105 | Russell et. al.; J. Polym. Sci. Polym. Phys, 1980, 18, 1271 | 0.50 |
| acryloyl morpholine | 147 | Elies, J.; Chimie Moderne, 1959, 4, 26, 53 | −0.94 |
| isobutyl methacrylate | 48 | Krause, S. et al.; J. Polym Sci. A., 1965, 3, 3573-3586 | 2.76 |
| tertiary butyl acrylate | 44 | BASF Specialty Monomers Technical data catalog | 2.02 |
| benzyl methacrylate | 72 | Munoz, M. I. et al., Thermochimica Acta, 1989, 146, 137-147. | 2.82 |
| n-propylmethacrylate | 35 | Rogers, S. S. et al., J. Phys. Chem., 1957, 61, 985-991. | 2.41 |

Urethane (Meth)Acrylate

Orthodontic articles according to the present disclosure comprise at least one urethane (meth)acrylate. Urethanes are prepared by the reaction of an isocyanate with an alcohol to form carbamate linkages. The urethane (meth)acrylate typically provides toughness (e.g., at least a minimum tensile strength and/or modulus and flexibility, (e.g., at least a minimum elongation at break)) to the final orthodontic article. In addition to the urethane functionality, the urethane (meth)acrylate further comprises a polycarbonate linking group. The linking group is afunctional group that connects two or more urethane groups, and may be divalent, trivalent, or tetravalent, and preferably divalent. In addition, the urethane (meth)acrylate optionally further comprises one or more functional groups selected from hydroxyl groups, carboxyl groups, amino groups, and siloxane groups. These functional groups can be reactive with other components of the polymerizable composition during polymerization. The urethane (meth)acrylate preferably has a weight average molecular weight (Mw) of 3,000 g/mol or greater, 4,000 g/mol or greater, 5,000 g/mol or greater, 6,000 g/mol or greater, 6,000 g/mol or greater, 7,000 g/mol or greater, 8,000 g/mol or greater, 9,000 g/mol or greater, 10,000 g/mol or greater, 11,000 g/mol or greater, or 12,000 g/mol or greater; and 50,000 g/mol or less, 45,000 g/mol or less, 40,000 g/mol or less, 35,000 g/mol or less, 32,000 g/mol or less, 30,000 g/mol or less, 28,000 g/mol or less, 25,000 g/mol or less, 23,000 g/mol or less, 20,000 g/mol or less, or 18,000 g/mol or less. Stated another way, the urethane (meth)acrylate may have a Mw of 3,000 g/mol to 50,000 g/mol, 6,000 g/mol to 40,000 g/mol, 6,000 g/mol to 18,000 g/mol, 6,000 g/mol to 35,000 g/mol, or 8,000 g/mol to 32,000 g/mol. Weight average molecular weight may be measured using gel permeation chromatography (GPC), for instance using the method described in the Examples below. Higher molecular weight of the urethane (meth)acrylates will result in higher viscosity resin formulations with comparable compositions and loadings, which makes them less flowable; lower molecular weight of the urethane (meth)acrylates will reduce their toughening effect on the cured orthodontic articles.

The urethane (meth)acrylate may be provided by one or more different urethane (meth)acrylates containing polymerized units of an aliphatic polycarbonate diol. Additionally, one or more urethane (meth)acrylates may also be present in the polymerizable composition that lack polymerized units of an aliphatic polycarbonate diol. Various suitable urethane (meth)acrylates, which can be present in the polymerizable composition alone or in combination, are described below. The polycarbonate urethane (meth)acrylate is the major urethane (meth)acrylate. When other urethane (meth)acrylates and/or or difunctional (e.g. di(meth)acrylate) components are present, the weight ratio of polycarbonate urethane (meth)acrylate to the total of other urethane (meth)acrylates and/or difunctional (e.g. di(meth)acrylate) components typically ranges from 1:1 to 25:1. In some embodiments, the weight ratio of polycarbonate urethane (meth)acrylate to the total of other urethane (meth)acrylates and/or or difunctional (e.g. di(meth)acrylate) components is at least 2:1, at least 3:1, or at least 4:1. The use of more than one urethane(meth) acrylate may provide somewhat different mechanical properties to the orthodontic article than using a single urethane (meth)acrylate in the polymerizable composition.

In one embodied synthetic route, the urethane (meth) acrylate comprises a reaction product of an aliphatic polycarbonate diol, a diisocyanate, and a hydroxy functional (meth)acrylate. One such suitable urethane (meth)acrylate is of Formula (VI):

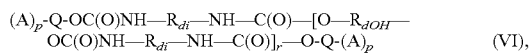
(A)$_p$-Q-OC(O)NH—R$_{di}$—NH—C(O)—[O—R$_{dOH}$— OC(O)NH—R$_{di}$—NH—C(O)]$_r$—O-Q-(A)$_p$ (VI), wherein A has the formula —XC(=O)C(R)=CH$_2$, wherein X is O, S, or NR$_4$, R$_4$ is H or alkyl of 1 to 4 carbon atoms, and R$_1$ is a lower alkyl of 1 to 4 carbon atoms or H, p is 1 or 2, Q is a polyvalent organic linking group, R$_{di}$ is the residue of a diisocyanate, R$_{dOH}$ is the residue of a polycarbonate polyol, and r averages from 1 to 15. In some embodiments, r is no greater than 15, 14, 13, 12, 11, or 10. In some embodiments, r averages at least 2, 3, 4, or 5. In some embodiments, A is a methacryl functional group, such as methacrylate.

Suitable amounts of each of the diisocyanate, hydroxy functional (meth)acrylate, and polycarbonate diol present in the polymerizable composition are based on molar ratios of each of these components to the others. For instance, a ratio of the diisocyanate (which has 2 isocyanate equivalents per mole of isocyanate compound) to the polycarbonate diol typically ranges from 4 molar equivalents of the diisocyanate to 1 molar equivalent of the alcohol of the polycarbonate diol, to 4 molar equivalents of the diisocyanate to 3 molar equivalents of the alcohol of the polycarbonate diol. In select embodiments, a ratio of the isocyanate to the polycarbonate diol is 4 molar equivalents of diisocyanate to 2 molar equivalents of the alcohol of the polycarbonate diol. The closer the ratio of the diisocyanate to the polycarbonate diol is to 1 molar equivalent of diisocyanate to 1 molar equivalent of the alcohol of the polycarbonate diol, the higher the weight average molecular weight of the resulting polyurethane (meth)acrylate produced in the polymerization reaction product.

A ratio of the diisocyanate to the hydroxy functional (meth)acrylate typically ranges from 4 molar equivalents of the diisocyanate to 3 molar equivalents of the hydroxy functional (meth)acrylate, to 4 molar equivalents of the diisocyanate to 1 molar equivalent of the hydroxy functional (meth)acrylate. In select embodiments, a ratio of the diisocyanate to the hydroxy functional (meth)acrylate is 4 molar equivalents of the diisocyanate to 2 molar equivalents of the hydroxy functional (meth)acrylate.

A ratio of the polycarbonate diol to the hydroxy functional (meth)acrylate typically ranges from 1 molar equivalent of the alcohol of the polycarbonate diol to 3 molar equivalents of the hydroxy functional (meth)acrylate, to 3 molar equivalents of the polycarbonate diol to 1 molar equivalents of the hydroxy functional (meth)acrylate. In select embodiments, a ratio of the polycarbonate diol to the hydroxy functional (meth)acrylate is 1 molar equivalent of the alcohol of the polycarbonate diol to 1 molar equivalent of the hydroxy functional (meth)acrylate.

In another embodied synthetic route, the urethane (meth) acrylate comprises a reaction product of an aliphatic polycarbonate diol, a diisocyanate, a diol (meth)acrylate, and a hydroxy functional (meth)acrylate. One such suitable the urethane (meth)acrylate is of Formula (V):

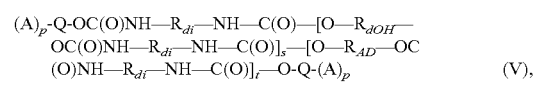
(A)$_p$-Q-OC(O)NH—R$_{di}$—NH—C(O)—[O—R$_{dOH}$— OC(O)NH—R$_{di}$—NH—C(O)]$_s$—[O—R$_{AD}$—OC (O)NH—R$_{di}$—NH—C(O)]$_t$—O-Q-(A)$_p$ (V), wherein A has the formula —XC(=O)C(R)=CH$_2$, wherein X is O, S, or NR$_4$, R$_4$ is H or alkyl of 1 to 4 carbon atoms, and R$_1$ is a lower alkyl of 1 to 4 carbon atoms or H, p is 1 or 2, Q is a polyvalent organic linking group, R$_{di}$ is the residue of a diisocyanate, R$_{dOH}$ is the residue of a polycarbonate polyol, s and t are independently 1 or greater, s+t averages from 2 to 15, wherein the s and t units may be connected to each other in any order, and R$_{AD}$ is the residue of a (meth)acrylated diol. In some embodiments, s+t is no greater than 15, 14, 13, 12, 11, or 10. In some embodiments, s averages at least 2, 3, 4, or 5. In some embodiments, t averages 1 or 2. In some embodiments, A is a (meth)acryl functional group, such as methacrylate. R$_{AD}$ always has a single (meth)acryl group. In some embodiments R$_{AD}$ is represented as

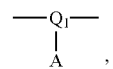

and may also be represented as -Q(A)-, wherein A is defined as above. In some embodiments, Q$_1$ is a straight or branched chain or cycle-containing aliphatic (e.g., divalent) connecting group.

In another embodied synthetic route, the urethane (meth) acrylate comprises a reaction product of an aliphatic polycarbonate diol and an isocyanate functional (meth)acrylate. One such suitable urethane (meth)acrylate is of Formula (VIII):

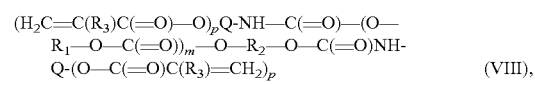
(H$_2$C=C(R$_3$)C(=O)—O)$_p$Q-NH—C(=O)—(O— R$_1$—O—C(=O))$_m$—O—R$_2$—O—C(=O)NH- Q-(O—C(=O)C(R$_3$)=CH$_2$)$_p$ (VIII), wherein Q is a polyvalent organic linking group, R$_3$ is a lower alkyl of 1 to 4 carbon atoms or H, p is 1 or 2, each R$_1$ and R$_2$ are independently an aliphatic, cycloaliphatic, or aliphatic/cycloaliphatic alkylene group and an average number of carbon atoms in a combination of all the R$_1$ and R$_2$ groups is 4 to 10, and m is 2 to 23. As an example, the compound of Formula (VIII) may, in select embodiments, be a compound of Formula (IX):

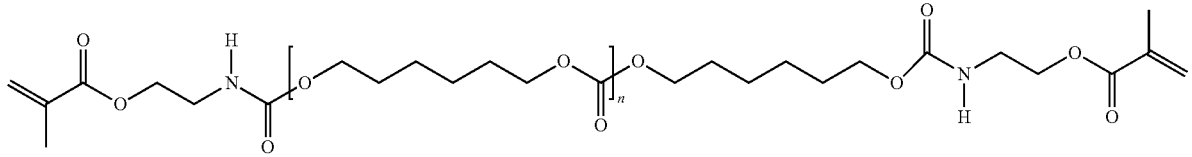

(IX)

In Formula (IX), n is about 6.7 for a 1000 molecular weight polycarbonate diol based on hexane diol.

In another embodied synthetic route, the urethane (meth)acrylate comprises a reaction product of an aliphatic polycarbonate diol, a diisocyanate, and an isocyanate functional (meth)acrylate. One such suitable urethane (meth)acrylate is of Formula (XI):

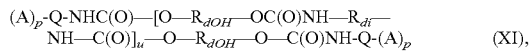

(XI), wherein u is 0 to 15, A has the formula $-XC(=O)C(R_1)=CH_2$, wherein X is O, S, or $NR_4$, $R_4$ is H or alkyl of 1 to 4 carbon atoms, and $R_1$ is a lower alkyl of 1 to 4 carbon atoms or H, p is 1 or 2, Q is a polyvalent organic linking group, $R_{di}$ is the residue of a diisocyanate, and $R_{dOH}$ is the residue of a polycarbonate polyol.

In another embodied synthetic route, the urethane (meth)acrylate comprises a reaction product of an aliphatic polycarbonate diol, a diisocyanate, a diol (meth)acrylate, and an isocyanate functional (meth)acrylate. One such suitable urethane (meth)acrylate is of Formula (XII):

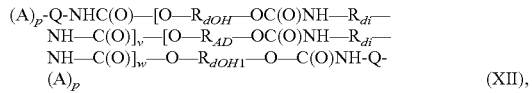

(XII), wherein, $R_{di}$, $R_{AD}$, Q, A, and p, are defined as above, v+w is 1 to 15, and $R_{dOH1}$ selected from $R_{dOH}$ or $R_{AD}$, with the provisos that if v is 0 then $R_{dOH1}$ is $R_{dOH}$, and if w is 0 then $R_{dOH1}$ is $R_{AD}$.

In another embodied synthetic route, the urethane (meth)acrylate containing polycarbonate moieties further comprises polymerized units of a polyester diol. However, the urethane (meth)acrylate contains the same or more polymerized units of the aliphatic polycarbonate diol than of the polyester diol. One such suitable urethane (meth)acrylate is of Formula (XIII):

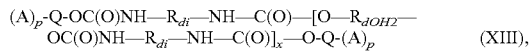

(XIII), wherein each $R_{dOH2}$ is independently selected from the residue of a polyester polyol or the residue of a polycarbonate polyol, and x is greater than 2.

In some embodiments, the polymerizable composition further comprises at least one second urethane (meth)acrylate lacking aliphatic polycarbonate moieties. For instance, such a urethane (meth)acrylate may comprise polymerized units of a polyester diol. One suitable urethane (meth)acrylate comprising polymerized units of a polyester diol is of Formula (XIII) or Formula (XIV):

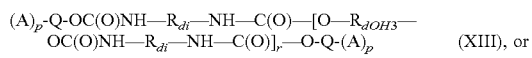

(XIII), or

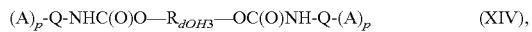

(XIV), wherein A has the formula $-XC(=O)C(R_1)=CH_2$, wherein X is O, S, or $NR_4$, $R_4$ is H or alkyl of 1 to 4 carbon atoms, and $R_1$ is a lower alkyl of 1 to 4 carbon atoms or H, p is 1 or 2, Q is a polyvalent organic linking group, $R_{di}$ is a residue of a diisocyanate, $R_{dOH3}$ is a residue of a polyester polyol, and r averages from 1 to 15.

Any combination of the urethane (meth)acrylates is contemplated to be used in polymerizable compositions and orthodontic articles. The various reactants mentioned above that may be used to form urethane (meth)acrylates (e.g., polycarbonate diols, diisocyanates, hydroxy functional (meth)acrylates, diol (meth)acrylates, isocyanate functional (meth)acrylates, and polyester polyols) are further described below, as well as additional components useful in polymerizable compositions and orthodontic articles according to the present disclosure.

Polycarbonate Diol

In some embodiments, the polycarbonate diol is of Formula (I):

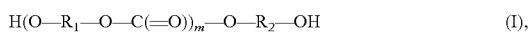

(I), wherein each of $R_1$ in each $(O-R_1-O-C(=O))$ repeat unit, and $R_2$ are independently an aliphatic, cycloaliphatic, or aliphatic/cycloaliphatic alkylene group and an average number of carbon atoms in a combination of all the $R_1$ and $R_2$ groups is 4 to 10, and m is (an integer of) 2 to 23. Stated another way, while some repeat units of $R_1$ and/or $R_2$ may have a carbon number of less than 4 (e.g., 2 or 3), enough of the repeat units have a sufficiently high carbon number that when the carbon numbers of all the repeat units of $R_1$ and $R_2$ in the polycarbonate diol of Formula (I) are averaged, that average falls within the range of 4 to 10, or any of 4 to 6, 4 to 7, 4 to 8, 4 to 9, 5 to 7, 5 to 8, 5 to 9, 5 to 10, 6 to 8, 6 to 9, 6 to 10, 7 to 9, 7 to 10, or 8 to 10. In contrast, a polycarbonate diol having a molecular weight of about 1,500 g/mol made with $CO_2$ and propylene oxide available as "CONVERGE POLYOL 212-20" from Aramco, (Dhahran, Saudi Arabia), has an average number of carbon atoms in a combination of all the $R_1$ and $R_2$ groups is just 3. In select embodiments, at least one of $R_1$ or $R_2$ is $-CH_2CH_2CH(CH_3)CH_2CH_2-$, $-(CH_2)_6-$, or $-(CH_2)_4-$, and preferably a combination of $-CH_2CH_2CH(CH_3)CH_2CH_2-$, and $-(CH_2)_6-$.

In some embodiments, either the polycarbonate diol has a number average molecular weight (Mn) of greater than 1,000 grams per mole (g/mol) or a weighted average of all polycarbonate diols present in the components has a Mn of greater than 1,000 g/mol, wherein Mn is determined by OH value. Stated a different way, when the components contain a single polycarbonate diol of Formula (I), the polycarbonate diol has a Mn higher than 1,000 g/mol. When the components contain two or more polycarbonate diols (e.g., one or more being of Formula (I)), the Mn of at least one of the polycarbonate diols may be 1,000 g/mol or less with the proviso that a weighted average of all the Mn values of the two or more polycarbonate diols is higher than 1,000 g/mol. For instance, components containing two polycarbonate diols could include a molar ratio of a first polycarbonate diol having a Mn of about 500 g/mol of 1 to a second polycarbonate diol having a Mn of about 1,500 g/mol of 2, resulting in a weighted average Mn of 1,167 g/mol. In certain embodiments, a polycarbonate diol (or a weighted average of all the polycarbonate diols present in the components) has a number average molecular weight of 1,500 g/mol or higher.

In some embodiments, one or more polycarbonate diols are present having a Mn of 450 grams per mole (g/mol) or greater, 500 g/mol or greater, 550 g/mol or greater, 600 g/mol or greater, 650 g/mol or greater, 700 g/mol or greater, 750 g/mol or greater, 800 g/mol or greater, 850 g/mol or greater, 900 g/mol or greater, 950 g/mol or greater, or 1,000 g/mol or greater; and 3,200 g/mol or less, 3,100 g/mol or less, 3,000 g/mol or less, 2,900 g/mol or less, 2,800 g/mol or less, 2,700 g/mol or less, 2,600 g/mol or less, 2,500 g/mol or less, 2,400 g/mol or less, 2,300 g/mol or less, 2,200 g/mol or less, 2,100 g/mol or less, 2,000 g/mol or less, 1,900 g/mol or less, 1,800 g/mol or less, or 1,700 g/mol or less. Stated another way, the polycarbonate diol may have a Mn of 450 g/mol to 3,200 g/mol, 800 g/mol to 3,200 g/mol, 1,000 g/mol to 3,200 g/mol, 1,500 g/mol to 3,200 g/mol, 1,800 g/mol to 3,200 g/mol, 450 g/mol to 2,200 g/mol, 800 g/mol to 2,200 g/mol, 1,000 g/mol to 2,200 g/mol, 1,500 g/mol to 2,200 g/mol, or 1,800 g/mol to 2,200 g/mol. Inclusion of a polycarbonate diol having a Mn of greater than 3,200 g/mol, on the other hand, may negatively impact the stiffness of a polymerization reaction product of the polymerization composition, by increasing the elastomeric character of the polymerization reaction product. In select embodiments, the polymerizable composition is essentially free of any diols that have a Mn lower than the one or more polycarbonate diols present in the components. In embodiments of polymerizable compositions containing a relatively low $T_g$ monomer (e.g., under 90° C., 80° C., or under 60° C.), inclusion of a polycarbonate diol having a Mn of greater than 1,500 g/mol may negatively impact the ability of a polymerization reaction product of the polymerization composition to yield (e.g., having increased brittleness). Similarly, in embodiments of polymerizable compositions containing a polycarbonate diol having a Mn of greater than 1,500 g/mol, inclusion of an insufficient amount of a relatively high $T_g$ monomer (e.g., over 90° C., 100° C., 125° C., or over 150° C.), may negatively impact the ability of a polymerization reaction product of the polymerization composition to yield (e.g., having increased brittleness).

Suitable polycarbonate diols for use in the components include for instance and without limitation, those commercially available from Kuraray Co. Ltd. (Tokyo, JP) under the trade designation "KURARAY POLYOL", e.g., specifically, each of the KURARAY POLYOL C series: C-590, C-1090, C-2050, C-2090, and C-3090; from Covestro LLC (Pittsburgh, PA) under the trade designation "DESMOPHEN", e.g., specifically, each of the DESMOPHEN C series: C-2100, C-2200, and C XP-2613.

Polyester Diol

In some embodiments, polyester diols are utilized in the preparation of the urethane (meth)acrylate.

In some embodiments, the polyester diol has Formula (XVI), as follows:

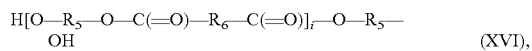

(XVI), wherein $R_5$ and $R_6$ are independently straight or branched chain or cycle-containing alkylene, groups, that optionally include heteroatoms, such as oxygen. $R_5$ and $R_6$ independently comprise 2 to 40 carbon atoms. The subscript "i" is typically at least 2, 3, 4, 5, 6, or 7. The subscript "i" is typically no greater than 50, 45, 40, 35, 30, 25, 20, or 15. In some embodiments, the $R_5$ and $R_6$ are alkylene.

Representative polyester diols include for example neopentyl glycol adipate diol, butane diol adipate diol; 3-methyl-1,5-pentanediol adipate diol; and 3-methyl-1,5-pentanediol sebecate diol, and dimer acid based polyols in which the dimer acid is derived for example from dimerization of two 18 carbon diacids such as linoleic acid.

In some embodiments, such as the diols just described, the polyester diol comprises a single $R_5$ group (e.g. neopentyl or 3-methyl-1,5-pentyl) and a single $R_6$ group (e.g. adipate).

In other embodiments, the polyester diol can be prepared from more than one diol and more than one acid. In this embodiment, the diol can contain two or more different $R_5$ groups and two or more different $R_6$ groups such as in the case of ethylene glycol-hexane diol/adipate-azelate copolyester diol.

In other embodiments, the polyester diol has Formula (XVII), as follows:

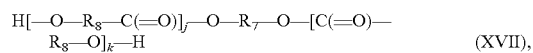

(XVII), wherein $R_7$ and $R_8$ are independently straight or branched chain or cycle-containing alkylene groups that optionally include heteroatoms such as oxygen, the alkylene groups independently comprise 2 to 40 carbon atoms. The subscripts "j" and "k" are typically independently at least 4, 5 or 6. The subscripts "j" and "k" are typically independently no greater than 25, 20, or 15.

One representative polyester diol of this type is polycaprolactone diol, such as available from Perstorp. In this embodiment, $R_8$ is a $C_5$ alkylene group and $R_7$ is the residue of an alcohol, such as ethylene glycol, butylene glycol, diethylene glycol, and the like.

In some embodiments, at least one of $R_5$ or $R_6$ of Formula (XVI) and at least one of R and $R_8$ of Formula (XVII) is a straight or branched chain or cycle-containing alkylene group independently comprising at least 4, 5, or 6 carbon atoms.

In some embodiments, each of the $R_5$ and $R_6$ groups of Formula (XVI) are alkylene groups independently comprising at least 4, 5, or 6 carbon atoms. In some embodiments, each of the $R_7$ and $R_8$ groups of Formula (XVII) are alkylene groups independently comprising at least 4, 5, or 6 carbon atoms.

The values of i, j, and k are chosen such that the molecular weight (Mn) of the diol is at least 500, 600, 700, 800, 900, or 1000 g/mole. In some embodiments, the molecular weight (Mn) of the diol is at least 1100, 1200, 1300, 1400, 1500 g/mole. In some embodiments, the molecular weight (Mn) of the diol is at least 1600, 1700, 1800, 1900, or 2000 g/mole. In some embodiments, the molecular weight (Mn) of the diol is no greater than 10,000; 9,000; 8,000; 7,000; 6,000; 5000; 4000; or 3000 g/mole. The values of i, j, and k can vary widely due to the range of carbons for the $R_5$, $R_6$, $R_7$, and $R_8$ groups.

Polyether Diol

In some embodiments, polyether diols are utilized in the preparation of the urethane (meth)acrylate. The polyether diol is typically of Formula (XVIII) as follows:

(XVIII),

Wherein each $R_9$ is independently selected from straight or branched chain or cycle-containing alkylene groups of 2 to 6 carbon atoms, more preferably 3-4 carbon atoms, and h is typically is at least 7, but no higher than 80. The value of h is chosen such that the molecular weight (Mn) of the diol is at least 500, 600, 700, 800, 900, or 1000 g/mole. In some embodiments, the molecular weight (Mn) of the diol is at least 1100, 1200, 1300, 1400, 1500 g/mole. In some embodiments, the molecular weight (Mn) of the diol is at least 1600, 1700, 1800, 1900, or 2000 g/mole. In some embodiments, the molecular weight (Mn) of the diol is no greater than 10,000; 9,000; 8,000; 7,000; 6,000; 5000; 4000; or 3000 g/mole. When the molecular weight is too low the elongation can be insufficient (i.e. less than 15-20%).

Diisocyanate

Diisocyanates that can be employed can be any organic isocyanate having two free isocyanate groups. Included are aliphatic, cycloaliphatic, aromatic and araliphatic isocyanates. Any of the known polyisocyanates such as alkyl and alkylene polyisocyanates, cycloalkyl and cycloalkylene polyisocyanates, and combinations such as alkylene and cycloalkylene polyisocyanates can be employed. In some embodiments, diisocyanates having the formula $R_{di}(NCO)_2$ can be used, with $R_{di}$ as defined above (e.g., an aliphatic and/or aromatic moiety between the isocyanate groups).

Specific examples of suitable diisocyanates include for instance and without limitation, 2,6-toluene diisocyanate (TDI), 2,4-toluene diisocyanate, methylenedicyclohexylene-4,4'-diisocyanate (H12MDI), 3-isocyanatomethyl-3,5, 5-trimethylcyclohexyl isocyanate (IPDI), 1,6-diisocyanatohexane (HDI), tetramethyl-m-xylylene diisocyanate, a mixture of 2,2,4- and 2,4,4-trimethyl-1,6-diisocyanatohexane (TMXDI), trans-1,4-hydrogenated xylylene diisocyanates (H6XDI), cyclohexyl-1,4-diisocyanate, 4,4'-methylene diphenyl diisocyanate, 2,4'-methylene diphenyl diisocyanate, a mixture of 4,4'-methylene diphenyl diisocyanate and 2,4'-methylene diphenyl diisocyanate, 1,5-naphthalene diisocyanate, 1,4-tetramethylene diisocyanate, 1,4-phenylene diisocyanate, 2,6- and 2,4-toluene diisocyanate, 1,5-naphthylene diisocyanate, 2,4' and 4,4'-diphenylmethane diisocyanate, pentamethylene diisocyanate, dodecamethylene diisocyanate, 1,3-cyclopentane diisocyanate, 1,3-cyclohexane diisocyanate, methyl 2,4-cyclohexane diisocyanate, methyl-2,6-cyclohexane diisocyanate, 1,4-bis (isocyanatomethyl) cyclohexane, 1,3-bis (isocyanatomethyl) cyclohexane, 4,4'-toluidine diisocyanate, 4,4'-diphenyl ether diisocyanate, 1,3- or 1,4-xylylene diisocyanate, lysine diisocyanate methyl ester, 3,3'-dimethyl-4,4'-diphenylmethane diisocyanate, 3,3'-dimethyl-phenylene diisocyanate, 2,5-bis (isocyanate methyl)-bicyclo[2.2.1]heptane, 2,6-bis (isocyanate methyl)-bicyclo[2.2.1]heptane, bis (2-isocyanate ethyl) fumarate, 4-diphenylpropane diisocyanate, trans-cyclohexane-1,4-diisocyanatehydrogenated dimer acid diisocyanate, a norbornene diisocyanate, methylenebis 6-isopropyl-1,3-phenyl diisocyanate, and any combination thereof. In select embodiments, the diisocyanate comprises IPDI.

It is also possible to include higher-functional polyisocyanates known from polyurethane chemistry or else modified polyisocyanates, for example containing carbodiimide groups, allophanate groups, isocyanurate groups and/or biuret groups.

Hydroxy Functional (Meth)Acrylate

In some embodiments, hydroxy functional (meth)acrylates are utilized in the preparation of the urethane (meth) acrylate. Typically, the hydroxy functional (meth)acrylate is of Formula (II):

wherein Q is a polyvalent organic linking group, A is a (meth)acryl functional group of the formula —XC(=O)C (R)=CH$_2$, wherein X is O, S, or NR$_4$, R$_4$ is H or alkyl of 1 to 4 carbon atoms, R$_1$ is a lower alkyl of 1 to 4 carbon atoms (e.g., methyl) or H, and wherein p is 1 or 2.

Q can be a straight or branched chain or cycle-containing connecting group. Q comprises typically no greater than 20 carbon atoms. Q can include a covalent bond, an alkylene, an arylene, an aralkylene, an alkarylene. Q can optionally include heteroatoms such as O, N, and S, and combinations thereof. Q can also optionally include a heteroatom-containing functional group such as carbonyl or sulfonyl, and combinations thereof. In some embodiments, Q is a straight chain, branched chain, or cycle-containing connecting group selected from arylene, aralkylene, and alkarylene. In yet other embodiments, Q is a straight chain, branched chain, or cycle-containing connecting group containing heteroatoms such as O, N, and S and/or a heteroatom containing functional group such as carbonyl and sulfonyl. In other embodiments, Q is a branched or cycle-containing alkylene group that optionally contains heteroatoms selected from O, N, S, and/or a heteroatom-containing functional group such as carbonyl and sulfonyl.

In some embodiments, in the hydroxy functional (meth) acrylate of Formula (II), Q is an alkylene group, p is 1, and in the (meth)acryl functional group A, X is O and R$_2$ is methyl or H. In certain preferred embodiments, in the hydroxy functional (meth)acrylate of Formula (II), Q is an alkylene group, p is 1, and in the (meth)acryl functional group A, X is O and R$_2$ is methyl. In some embodiments, Q is an alkylene comprising no greater than 12, 10, 8, or 6 carbon atoms, and may be a C$_2$, C$_3$, or C$_4$ alkylene group.

Suitable example hydroxy functional (meth)acrylates include for instance and without limitation, 2-hydroxyethyl (meth)acrylate, hydroxypropyl acrylate (all isomers), hydroxybutyl acrylate (all isomers), poly(e-caprolactone) mono[2-(meth)acryloxy ethyl] esters such as caprolactone monoacrylate available under the trade designation "SR-495" from Sartomer USA (Arkema Group) (Exton, PA), glycerol dimethacrylate, 1-(acryloxy)-3-(methacryloxy)-2-propanol, 2-hydroxy-3-phenyloxypropyl (meth)acrylate, 2-hydroxyalkyl (meth)acryloyl phosphate, 4-hydroxycyclohexyl (meth)acrylate, trimethylolpropane di(meth)acrylate, trimethylolethane di(meth)acrylate, 1,4-butanediol mono (meth)acrylate, neopentyl glycol mono(meth)acrylate, 1,6-hexanediol mono(meth)acrylate, 3-chloro-2-hydroxypropyl (meth)acrylate, 2-hydroxy-3-alkyloxy(meth)acrylate, polyethylene glycol mono(meth)acrylate, polypropylene glycol mono(meth)acrylate, ethylene oxide-modified phthalic acid (meth)acrylate, and 4-hydroxycyclohexyl (meth)acrylate.

Diol (Meth)Acrylate

In some embodiments, diol (meth)acrylates are utilized in the preparation of the urethane (meth)acrylate. Typically, the diol (meth)acrylate is of Formula (XV):

wherein A has the formula —XC(=O)C(R$_1$)=CH$_2$, wherein X is O, S, or NR$_4$, R$_4$ is H or alkyl of 1 to 4 carbon atoms, and R$_1$ is a lower alkyl of 1 to 4 carbon atoms or H, and Q$_1$ is a polyvalent organic linking group. Q$_1$ comprises typically no greater than 20 carbon atoms. Q$_1$ can include a covalent bond, an alkylene, an arylene, an aralkylene, an alkarylene. Q$_1$ can optionally include heteroatoms such as O, N, and S, and combinations thereof. Q$_1$ can also optionally include a heteroatom-containing functional group such as carbonyl or sulfonyl, and combinations thereof. In some embodiments, Q$_1$ is a straight chain, branched chain, or cycle-containing connecting group (e.g., divalent group) selected from arylene, aralkylene, and alkarylene. In yet other embodiments, Q$_1$ is a straight chain, branched chain, or cycle-containing connecting group containing heteroatoms such as O, N, and S and/or a heteroatom containing functional group such as carbonyl and sulfonyl. In other embodiments, $Q_1$ is a branched or cycle-containing alkylene group that optionally contains heteroatoms selected from O, N, S, and/or a heteroatom-containing functional group such as carbonyl and sulfonyl.

Examples of the diol (meth)acrylate include, glycerol-2-methacrylate (1,3-bis hydroxy-propyl-2-methacrylate), 2,3-Dihydroxypropyl methacrylate, glycerin mono(meth)acrylate, trimethylolpropane monoacrylate (shown in the structure below), and

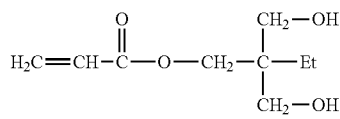

trimethylolpropane monomethacrylate (shown in the structure below),

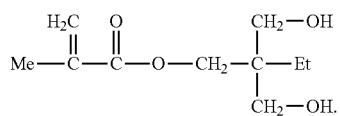

Additional suitable diol (meth)acrylates may be synthesized as described in the Examples below, for instance an acrylated diol adduct of diethanolamine and isocyanatoethyl methacrylate, an acrylated diol adduct of diethanolamine and isocyanatoethyl acrylate, an acrylated diol adduct of diethanolamine and isocyanatoethoxyethyl methacrylate, and an acrylated diol adduct of ethylene glycol mono-acetoacetate mono-methacrylate and 2-hydroxyethyl acrylate.

Isocyanate Functional (Meth)Acrylate

In some embodiments, isocyanate functional (meth)acrylates are utilized in the preparation of the urethane (meth)acrylate. In typical embodiments, the isocyanate functional (meth)acrylate is of Formula (VII):

$(A)_p$-Q-NCO    (VII);

wherein A and Q are the same as described above with respect to the hydroxy functional (meth)acrylate, and p is 1 or 2.

Examples of the isocyanate functional (meth)acrylates include isocyanatoethyl methacrylate, isocyanatoethoxyethyl methacrylate, isocyanatoethyl acrylate, and 1,1-(bisacryloyloxymethyl) ethyl isocyanate, which are for instance commercially available from Showa Denko (Tokyo, Japan).

Catalyst

The polymerizable composition optionally comprises a catalyst. Typically, catalyst is included in an amount of 0.01 wt. % to 5 wt. %, based on the total weight of the polymerizable components.

Examples of suitable catalysts include for instance and without limitation, dioctyl dilaurate (DOTDL), stannous octoate, dibutyltin diacetate, dibutyltin dilaurate, dibutyltin mercaptide, dibutyltin thiocarboxylate, dibutyltin dimaleate, dioctyltin mercaptide, dioctyltin thiocarboxylate, lead 2-ethylhexanoate, tetra-alkyl titanates such as tetrabutyl titanate (TBT), triethylamine, N, N-dimethylcyclohexylamine, N-methylmorpholine, N-ethylmorpholine, N, N-dimethyl-p-toluidine, beta-(dimethylamino) propionitrile, N-methylpyrrolidone, N, N-dicyclohexylmethylamine, dimethylamino-ethanol, dimethylamino-ethoxyethanol, triethylenediamine, N, N, N'-trimethyl aminoethyl ethanol amine, N, N, N', N'-tetramethylethylenediamine, N, N, N', N'-tetramethyl-1,3-diamine, N, N, N', N'-tetramethyl-1,6-hexanediol-diamine, bis(N, N-dimethylaminoethyl) ether, N'-cyclohexyl-N, N-dimethyl-formamidine, N, N'-dimethylpiperazine, trimethyl piperazine, bis(aminopropyl) piperazine, N—(N, N'-dimethylaminoethyl) morpholine, bis(morpholinoethyl) ether, 1,2-dimethyl imidazole, N-methylimidazole, 1,4-diamidines, diazabicyclo-[2.2.2]-octane (DABCO), 1,4-diazabicyclo[3.3.0]-oct-4-ene (DBN), 1,8-diazabicyclo-[4.3.0]-non-5-ene (DBN), 1,8-diazabicyclo-[5.4.0]-undec-7-ene (DBU), and phenol salts, salts such as octyl acid salts, N, N, N', N''-pentamethyldiethylenetriamine, N, N, N', N''-pentamethyl dipropylenetriamine, tetramethylguanidine, N-cyclohexyl-N', N', N'', N''-tetramethyl guanidine, N-methyl-N'-(2-dimethyl amino ethyl) piperazine, 1,3,5-tris(N, N-dimethyl-propyl)-hexahydro-1,3,5-triazine.

In any embodiment, the catalyst comprises zinc, an amine, tin, zirconium, or bismuth. The catalyst can comprise tin, such as dibutyltin diacrylate. Preferably, however, the catalyst is free of tin, as tin catalysts may not be desirable to include in orthodontic articles that will be in contact with a patient's mouth.

The catalyst may comprise an organometallic zinc complex that is free of 2-ethylhexyl carboxylate and 2-ethylhexanoic acid, such as the zinc catalyst commercially available from King Industries, Inc. (Norwalk, CT) under the trade designation K-KAT XK-672, and/or other zinc catalysts available from King Industries, such as K-KAT XK-661, and K-KAT XK-635. Another suitable catalyst is bismuth neodecanoate, for instance commercially available from Sigma-Aldrich (St. Louis, MO), as well as bismuth catalysts available from King Industries under the trade designations K-KAT XK-651 and K-KAT 348. Available aluminum based catalysts include K-KAT 5218 from King Industries. Further, zirconium based catalysts include K-KAT 4205 and K-KAT 6212 available from King Industries.

Photoinitiator

Polymerizable compositions of the present disclosure typically include at least one photoinitiator. Suitable exemplary photoinitiators are those available under the trade designations OMNIRAD from IGM Resins (Waalwijk, The Netherlands) and include 1-hydroxycyclohexyl phenyl ketone (OMNIRAD 184), 2,2-dimethoxy-1,2-diphenylethan-1-one (OMNIRAD 651), bis(2,4,6 trimethylbenzoyl) phenylphosphineoxide (OMNIRAD 819), 1-[4-(2-hydroxyethoxy)phenyl]-2-hydroxy-2-methyl-1-propane-1-one (OMNIRAD 2959), 2-benzyl-2-dimethylamino-1-(4-morpholinophenyl)butanone (OMNIRAD 369), 2-Dimethylamino-2-(4-methyl-benzyl)-1-(4-morpholin-4-yl-phenyl)-butan-1-one (OMNIRAD 379), 2-methyl-1-[4-(methylthio) phenyl]-2-morpholinopropan-1-one (OMNIRAD 907), Oligo[2-hydroxy-2-methyl-1-[4-(1-methylvinyl)phenyl] propanone] ESACURE ONE (Lamberti S.p.A., Gallarate, Italy), 2-hydroxy-2-methyl-1-phenyl propan-1-one (DAROCUR 1173), 2, 4, 6-trimethylbenzoyldiphenylphosphine oxide (OMNIRAD TPO), and 2, 4, 6-trimethylbenzoylphenyl phosphinate (OMNIRAD TPO-L). Additional suitable photoinitiators include for example and without limitation, benzyl dimethyl ketal, 2-methyl-2-hydroxypropiophenone, benzoin methyl ether, benzoin isopropyl ether, anisoin methyl ether, aromatic sulfonyl chlorides, photoactive oximes, and combinations thereof.

In some embodiments, a photoinitiator is present in a photopolymerizable composition in an amount of up to about 5% by weight, based on the total weight of polymerizable components in the photopolymerizable composition. In some cases, a photoinitiator is present in an amount of 0.1 wt. % or more, 0.2 wt. % or more, 0.3 wt. % or more, 0.4 wt. % or more, 0.5 wt. % or more, 0.6 wt. % or more, 0.7 wt. % or more, 0.8 wt. % or more, 0.9 wt. % or more, 1.0 wt. % or more, 1.25 wt. % or more, or 1.5 wt. % or more; and 5 wt. % or less, 4.8 wt. % or less, 4.6 wt. % or less, 4.4 wt. % or less, 4.2 wt. % or less, 4.0 wt. % or less, 3.8 wt. % or less, 3.6 wt. % or less, 3.4 wt. % or less, 3.2 wt. % or less, 3.0 wt. % or less, 2.8 wt. % or less, 2.6 wt. % or less, 2.4 wt. % or less, 2.2 wt. % or less, 2.0 wt. % or less, 1.8 wt. % or less, or 1.6 wt. % or less. Stated another way, the photoinitiator may be present in an amount of about 0.1-5% by weight, 0.2-5% by weight, or 0.5-5% by weight, based on the total weight of the photopolymerizable composition.

Further, a thermal initiator can optionally be present in a polymerizable composition described herein. In some embodiments, a thermal initiator is present in a polymerizable composition or in an amount of up to about 5% by weight, based on the total weight of polymerizable components in the polymerizable composition. In some cases, a thermal initiator is present in an amount of about 0.1-5% by weight, based on the total weight of polymerizable components in the polymerizable composition. Suitable thermal initiators include for instance and without limitation, peroxides such as benzoyl peroxide, dibenzoyl peroxide, dilauryl peroxide, cyclohexane peroxide, methyl ethyl ketone peroxide, hydroperoxides, e.g., tert-butyl hydroperoxide and cumene hydroperoxide, dicyclohexyl peroxydicarbonate, 2,2,-azo-bis(isobutyronitrile), and t-butyl perbenzoate. Examples of commercially available thermal initiators include initiators available from DuPont Specialty Chemical (Wilmington, DE) under the VAZO trade designation including VAZO 67 (2,2'-azo-bis(2-methybutyronitrile)) VAZO 64 (2,2'-azo-bis(isobutyronitrile)) and VAZO 52 (2,2'-azo-bis(2,2-dimethyvaleronitrile)), and LUCIDOL 70 from Elf Atochem North America, Philadelphia, PA.

In some embodiments, an initiator comprises a polymer comprising a free-radical photoinitiator group, e.g., a polymer backbone and pendent photoinitiator groups or terminal photoinitiator groups linked by a polymer chain. In some embodiments, an initiator comprises a macromolecule comprising a photoinitiator group, in which the macromolecule typically has a molecular weight of at least 500 g/mole. Such initiators are described in detail in co-owned International Application No. US2018/062074 (Chakraborty et al.).

In certain aspects, the use of more than one initiator assists in increasing the percentage of monomer that gets incorporated into the reaction product of polymerizable components and thus decreasing the percentage of the monomer that remains uncured. In some embodiments, at least one initiator comprises a first free-radical photoinitiator having sufficient absorbance at a first wavelength range; and a second free-radical initiator selected from a second photoinitiator having sufficient absorbance at a second wavelength range, wherein the second wavelength range is different than the first wavelength range, or a thermal free-radical initiator. Such initiator systems are described in detail in co-owned International Application No. US2018/062085 (Chakraborty et al.).

Additional Components

In some embodiments, the polymerizable composition further comprises one or more side reaction products in addition to the urethane (meth)acrylate. Depending on the selectivity of the catalyst and/or the weight ratios of the components, oligomers of the reactants may be produced. The order of addition of components in preparing the polymerizable composition affects the relative amounts of polymers and oligomers produced in the polymerized reaction product. For instance, adding a diisocyanate to a polycarbonate diol first, followed by adding the monofunctional (meth)acrylate results in a higher ratio of urethane (meth) acrylate to side products such as oligomers, than instead adding the monofunctional (meth)acrylate to the diisocyanate first, followed by adding the polycarbonate diol.

Oligomers having a structure of monofunctional (meth) acrylate monomer-isocyanate-monofunctional (meth)acrylate monomer have been found to be a byproduct of the polymerization reaction of components in certain embodiments. It is possible to purify the urethane (meth)acrylate to remove such side products. Alternatively, additional side products such as oligomers may be added to the polymerized reaction product, particularly when a specific reaction generates a small amount of one or more side products. It has been discovered that some side product components can improve at least one of modulus or extent of crosslinking after the polymerizable composition has been cured.

For example, polymerizable compositions optionally comprise a compound of Formula (III):

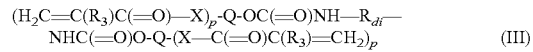

$$(H_2C=C(R_3)C(=O)-X)_p\text{-Q-OC}(=O)NH-R_{di}-NHC(=O)O\text{-Q-}(X-C(=O)C(R_3)=CH_2)_p \quad \text{(III)}$$

wherein Q is a polyvalent organic linking group, X is O, S, or $NR_4$, $R_4$ is H or alkyl of 1 to 4 carbon atoms, $R_3$ is a lower alkyl of 1 to 4 carbon atoms or H, p is 1 or 2, and $R_{di}$ is the residue of a diisocyanate as defined above. Typically, the compound of Formula (III) is produced during the polymerization of the a diisocyanate, polycarbonate diol, and a monofunctional (meth)acrylate monomer, as described above. The specific formulation of the components will affect how much of a compound of Formula (III) is made during the polymerization. For instance, the specificity of the catalyst towards catalyzing the formation of the urethane (meth)acrylate can affect the amount of the compound of Formula (III) generated during the polymerization of the components. In certain embodiments, the compound of Formula (III) is added to the polymerizable composition, particularly when a smaller amount of the compound of Formula (III) is produced by the polymerization of components than desired. In any embodiment, the compound may advantageously improve crosslinking during the polymerization reaction, increase the modulus or the polymerization reaction product, or both. Regardless of if the compound of Formula (III) is formed during the polymerization of the components, added separately to the polymerizable composition, or both, in some embodiments the compound of Formula (III) is present in an amount of 0.05 weight percent (wt. %) or greater, based on the weight of the polymerizable composition, 0.1 wt. % or greater, 0.5 wt. % or greater, 1 wt. % or greater, 1.5 wt. % or greater, 2.5 wt. % or greater, 2 wt. % or greater, 3 wt. % or greater, 4 wt. % or greater, 5 wt. % or greater, 6 wt. % or greater, 7 wt. % or greater, 8 wt. % or greater, or 9 wt. % or greater; and 20 wt. % or less, 18 wt. % or less, 16 wt. % or less, 15 wt. % or less, 14 wt. % or less, 12 wt. % or less, or 10 wt. % or less, based on the weight of the polymerizable composition. Stated another way, the compound of Formula (III) may be present in the polymerizable composition in an amount of 0.05 to 20 weight percent (wt. %), 1.5 to 12 wt. %, 2.5 to 12 wt. %, 5 to 15 wt. %, 5 to 12 wt. %, 7 to 15 wt. %, 7 to 12 wt. %, or 5 to 20 wt. %, based on the weight of the polymerizable composition. Optionally, X is O in the compound of Formula (III). In select embodiments, the compound of Formula (III) is of Formula (IV).

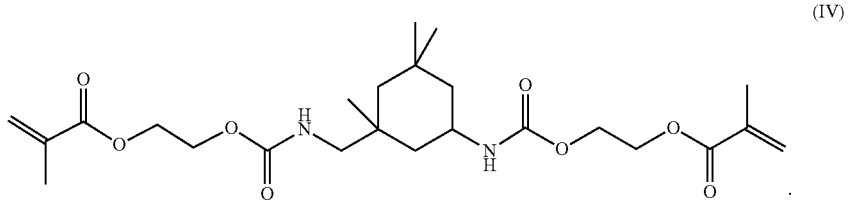 [SMILES: C=C(C)C(=O)OCCOC(=O)NCC1(C)CC(NC(=O)OCCOC(=O)C(=C)C)CC(C)(C)C1]

(IV)

Difunctional Component

Polymerizable compositions of the present disclosure optionally include at least one difunctional component, such as a difunctional (meth)acrylate monomer or oligomer. A difunctional component present in a polymerizable composition can co-react with the polyurethane (meth)acrylate (e.g., is capable of undergoing addition polymerization).

A difunctional component (e.g., monomer) is optionally present in an amount of up to 15 wt. %, based on the total weight of the polymerizable composition, up to 12 wt. %, up to 10 wt. %, or up to 8 wt. %, based on the total weight of the polymerizable composition. Including more than 15 wt. % difunctional components may lead to more crosslinking than desired and decrease the elongation of the orthodontic article.

Suitable difunctional monomers include for instance and without limitation, compounds having the Formula (X):

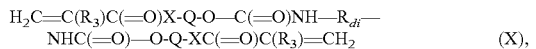

wherein $R_3$ is as defined for Formula (II) and $R_{di}$ is the residue of a diisocyanate, or compounds having the Formula (XI):

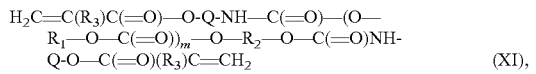

wherein Q, X, and $R_3$ are as defined for Formula (II) and $R_1$ and $R_2$ are as defined for Formula (I). Additional suitable difunctional monomers include hydroxyethyl methacrylate diester of terephthalic acid, 1,12-dodecanediol dimethacrylate, alkoxylated hexanediol diacrylate, alkoxylated neopentyl glycol diacrylate, caprolactone modified neopentylglycol hydroxypivalate diacrylate, caprolactone modified neopentylglycol hydroxypivalate diacrylate, cyclohexanedimethanol diacrylate, diethylene glycol diacrylate, dipropylene glycol diacrylate, ethoxylated (10) bisphenol A diacrylate, ethoxylated (3) bisphenol A diacrylate, ethoxylated (30) bisphenol A diacrylate, ethoxylated (4) bisphenol A diacrylate, hydroxypivalaldehyde modified trimethylolpropane diacrylate, neopentyl glycol diacrylate, polyethylene glycol (200) diacrylate, polyethylene glycol (400) diacrylate, polyethylene glycol (600) diacrylate, propoxylated neopentyl glycol diacrylate, tetraethylene glycol diacrylate, tricyclodecanedimethanol diacrylate, triethylene glycol diacrylate, tripropylene glycol diacrylate, or any combination thereof. Further suitable difunctional monomers include the dimethacrylates of each of the above listed diacrylates.

Typically, the polymerizable compositions are essentially free of trihydric alcohols, which are alcohols having three hydroxyl groups. This is due to such alcohols increasing the hydrophilicity of the polymerizable composition, which may result in an undesirably high water absorption during use of an orthodontic article prepared from the polymerizable composition.

Additives

Polymerizable compositions described herein, in some instances, further comprise one or more additives, such as one or more additives selected from the group consisting of inhibitors, stabilizing agents, sensitizers, absorption modifiers, fillers and combinations thereof.

In addition, a polymerizable material composition described herein can further comprise one or more sensitizers to increase the effectiveness of one or more photoinitiators that may also be present. In some embodiments, a sensitizer comprises isopropylthioxanthone (ITX) or 2-chlorothioxanthone (CTX). Other sensitizers may also be used. If used in the polymerizable composition, a sensitizer can be present in an amount ranging of about 0.01% by weight or about 1% by weight, based on the total weight of the polymerizable composition.

A polymerizable composition described herein optionally also comprises one or more polymerization inhibitors or stabilizing agents. A polymerization inhibitor is often included in a polymerizable composition to provide additional thermal stability to the composition. A stabilizing agent, in some instances, comprises one or more anti-oxidants. Any anti-oxidant not inconsistent with the objectives of the present disclosure may be used. In some embodiments, for example, suitable anti-oxidants include various aryl compounds, including butylated hydroxytoluene (BHT), which can also be used as a polymerization inhibitor in embodiments described herein. In addition to or as an alternative, a polymerization inhibitor comprises methoxyhydroquinone (MEHQ).

In some embodiments, a polymerization inhibitor, if used, is present in an amount of about 0.001-2% by weight, 0.001 to 1% by weight, or 0.01-1% by weight, based on the total weight of the polymerizable composition. Further, if used, a stabilizing agent is present in a polymerizable composition described herein in an amount of about 0.1-5% by weight, about 0.5-4% by weight, or about 1-3% by weight, based on the total weight of the polymerizable composition.

A polymerizable composition as described herein can also comprise one or more UV absorbers including dyes, optical brighteners, pigments, particulate fillers, etc., to control the penetration depth of actinic radiation. One particularly suitable UV absorber is Tinuvin 326 (2-(5-chloro-2H-benzotriazol-2-yl)-6-(1,1-dimethylethyl)-4-methylphenol, obtained from BASF Corporation, Florham Park, NJ Another particularly suitable UV absorber that is an optical brightener that is Tinopal OB, a benzoxazole, 2,2'-(2,5-thiophenediyl) bis[5-(1,1-dimethylethyl)], also available from BASF Corporation. Another suitable UV absorber is an optical brightener comprising a compound of the following structure:

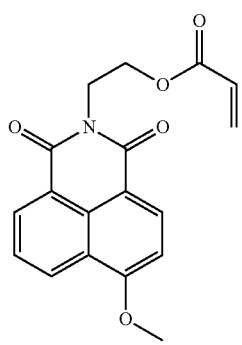 [SMILES: C=CC(=O)OCCN1C(=O)c2cccc3c(OC)ccc(c23)C1=O]

This compound may be synthesized as described in detail in the Examples below. The UV absorber, if used, can be present in an amount of about 0.001-5% by weight, about 0.01-1% by weight, about 0.1-3% by weight, or about 0.1-1% by weight, based on the total weight of the photopolymerizable composition.

Polymerizable compositions may include fillers, including nano-scale fillers. Examples of suitable fillers are naturally occurring or synthetic materials including, but not limited to: silica ($SiO_2$ (e.g., quartz)); alumina ($Al_2O_3$), zirconia, nitrides (e.g., silicon nitride); glasses and fillers derived from, for example, Zr, Sr, Ce, Sb, Sn, Ba, Zn, and Al; feldspar; borosilicate glass; kaolin (china clay); talc; zirconia; titania; and submicron silica particles (e.g., pyrogenic silicas such as those available under the trade designations AEROSIL, including "OX 50," "130," "150" and "200" silicas from Degussa Corp., Akron, OH and CAB-O-SIL M5 and TS-720 silica from Cabot Corp., Tuscola, IL). Organic fillers made from polymeric materials are also possible, such as those disclosed in International Publication No. WO09/045752 (Kalgutkar et al.).

The compositions may further contain fibrous reinforcement and colorants such as dyes, pigments, and pigment dyes. Examples of suitable fibrous reinforcement include PGA microfibrils, collagen microfibrils, and others as described in U.S. Pat. No. 6,183,593 (Narang et al.). Examples of suitable colorants as described in U.S. Pat. No. 5,981,621 (Clark et al.) include 1-hydroxy-4-[4-methylphenylamino]-9,10-anthracenedione (FD&C violet No. 2); disodium salt of 6-hydroxy-5-[(4-sulfophenyl)oxo]-2-naphthalenesulfonic acid (FD&C Yellow No. 6); 9-(o-carboxyphenyl)-6-hydroxy-2,4,5,7-tetraiodo-3H-xanthen-3-one, disodium salt, monohydrate (FD&C Red No. 3); and the like.

Discontinuous fibers are also suitable fillers, such as fibers comprising carbon, ceramic, glass, or combinations thereof. Suitable discontinuous fibers can have a variety of compositions, such as ceramic fibers. The ceramic fibers can be produced in continuous lengths, which are chopped or sheared to provide the discontinuous ceramic fibers. The ceramic fibers can be produced from a variety of commercially available ceramic filaments. Examples of filaments useful in forming the ceramic fibers include the ceramic oxide fibers sold under the trademark NEXTEL (3M Company, St. Paul, MN). NEXTEL is a continuous filament ceramic oxide fiber having low elongation and shrinkage at operating temperatures, and offers good chemical resistance, low thermal conductivity, thermal shock resistance, and low porosity. Specific examples of NEXTEL fibers include NEXTEL 312, NEXTEL 440, NEXTEL 550, NEXTEL 610 and NEXTEL 720. NEXTEL 312 and NEXTEL 440 are refractory aluminoborosilicate that includes $Al_2O_3$, $SiO_2$ and $B_2O_3$. NEXTEL 550 and NEXTEL 720 are aluminosilica and NEXTEL 610 is alumina. During manufacture, the NEXTEL filaments are coated with organic sizings or finishes which serves as aids in textile processing. Sizing can include the use of starch, oil, wax or other organic ingredients applied to the filament strand to protect and aid handling. The sizing can be removed from the ceramic filaments by heat cleaning the filaments or ceramic fibers as a temperature of 700° C. for one to four hours.

The ceramic fibers can be cut, milled, or chopped so as to provide relatively uniform lengths, which can be accomplished by cutting continuous filaments of the ceramic material in a mechanical shearing operation or laser cutting operation, among other cutting operations. Given the highly controlled nature of certain cutting operations, the size distribution of the ceramic fibers is very narrow and allow to control the composite property. The length of the ceramic fiber can be determined, for instance, using an optical microscope (Olympus MX61, Tokyo, Japan) fit with a CCD Camera (Olympus DP72, Tokyo, Japan) and analytic software (Olympus Stream Essentials, Tokyo, Japan). Samples may be prepared by spreading representative samplings of the ceramic fiber on a glass slide and measuring the lengths of at least 200 ceramic fibers at 10× magnification.

Suitable fibers include for instance ceramic fibers available under the trade name NEXTEL (available from 3M Company, St. Paul, MN), such as NEXTEL 312, 440, 610 and 720. One presently preferred ceramic fiber comprises polycrystalline α-$Al_2O_3$. Suitable alumina fibers are described, for example, in U.S. Pat. No. 4,954,462 (Wood et al.) and U.S. Pat. No. 5,185,299 (Wood et al.). Exemplary alpha alumina fibers are marketed under the trade designation NEXTEL 610 (3M Company, St. Paul, MN). In some embodiments, the alumina fibers are polycrystalline alpha alumina fibers and comprise, on a theoretical oxide basis, greater than 99 percent by weight $Al_2O_3$ and 0.2-0.5 percent by weight $SiO_2$, based on the total weight of the alumina fibers. In other embodiments, some desirable polycrystalline, alpha alumina fibers comprise alpha alumina having an average grain size of less than one micrometer (or even, in some embodiments, less than 0.5 micrometer). In some embodiments, polycrystalline, alpha alumina fibers have an average tensile strength of at least 1.6 GPa (in some embodiments, at least 2.1 GPa, or even, at least 2.8 GPa). Suitable aluminosilicate fibers are described, for example, in U.S. Pat. No. 4,047,965 (Karst et al). Exemplary aluminosilicate fibers are marketed under the trade designations NEXTEL 440, and NEXTEL 720, by 3M Company (St. Paul, MN). Aluminoborosilicate fibers are described, for example, in U.S. Pat. No. 3,795,524 (Sowman). Exemplary aluminoborosilicate fibers are marketed under the trade designation NEXTEL 312 by 3M Company. Boron nitride fibers can be made, for example, as described in U.S. Pat. No. 3,429,722 (Economy) and U.S. Pat. No. 5,780,154 (Okano et al.).

Ceramic fibers can also be formed from other suitable ceramic oxide filaments. Examples of such ceramic oxide filaments include those available from Central Glass Fiber Co., Ltd. (e.g., EFH75-01, EFH150-31). Also preferred are aluminoborosilicate glass fibers, which contain less than about 2% alkali or are substantially free of alkali (i.e., "E-glass" fibers). E-glass fibers are available from numerous commercial suppliers.

Examples of useful pigments include, without limitation: white pigments, such as titanium oxide, zinc phosphate, zinc sulfide, zinc oxide and lithopone; red and red-orange pigments, such as iron oxide (maroon, red, light red), iron/ chrome oxide, cadmium sulfoselenide and cadmium mercury (maroon, red, orange); ultramarine (blue, pink and violet), chrome-tin (pink) manganese (violet), cobalt (violet); orange, yellow and buff pigments such as barium titanate, cadmium sulfide (yellow), chrome (orange, yellow), molybdate (orange), zinc chromate (yellow), nickel titanate (yellow), iron oxide (yellow), nickel tungsten titanium, zinc ferrite and chrome titanate; brown pigments such as iron oxide (buff, brown), manganese/antimony/titanium oxide, manganese titanate, natural siennas (umbers), titanium tungsten manganese; blue-green pigments, such as chrome aluminate (blue), chrome cobalt-alumina (turquoise), iron blue (blue), manganese (blue), chrome and chrome oxide (green) and titanium green; as well as black pigments, such as iron oxide black and carbon black. Combinations of pigments are generally used to achieve the desired color tone in the cured composition.

The use of florescent dyes and pigments can also be beneficial in enabling the printed composition to be viewed under black-light. A particularly useful hydrocarbon soluble fluorescing dye is 2,5-bis(5-tert-butyl-2-benzoxazolyl) 1 thiophene. Fluorescing dyes, such as rhodamine, may also be bound to cationic polymers and incorporated as part of the resin.

If desired, the compositions of the disclosure may contain other additives such as indicators, accelerators, surfactants, wetting agents, antioxidants, tartaric acid, chelating agents, buffering agents, and other similar ingredients that will be apparent to those skilled in the art. Additionally, medicaments or other therapeutic substances can be optionally added to the polymerizable compositions. Examples include, but are not limited to, fluoride sources, whitening agents, anticaries agents (e.g., xylitol), remineralizing agents (e.g., calcium phosphate compounds and other calcium sources and phosphate sources), enzymes, breath fresheners, anesthetics, clotting agents, acid neutralizers, chemotherapeutic agents, immune response modifiers, thixotropes, polyols, anti-inflammatory agents, antimicrobial agents, antifungal agents, agents for treating xerostomia, desensitizers, and the like, of the type often used in dental compositions.

In select embodiments, the additive comprises an antimicrobial lipid. Certain preferred embodiments have good to excellent activity against *Streptococcus mutans* (*S. mutans*) bacteria, which is known to lead to a number of undesirable clinical side effects that include origination of caries, calcified plaque, irritation of gum tissue leading up to periodontal diseases, etc. As used herein, "antimicrobial lipid" means an antiseptic having at least one (C6)alkyl or alkylene chain (preferably at least one (C7) or (C8) chain, and preferably having a solubility in water of no greater than 1.0 gram per 100 grams (1.0 g/100 g) deionized water, such as no greater than 0.5 g/100 g, 0.25 g/100 g, or 0.10 g/100 g deionized water. Preferred antimicrobial lipids have a solubility in deionized water of at least 100 micrograms (μg) per 100 grams deionized water, 500 μg/100 g deionized water, or at least 1000 μg/100 g deionized water. The antimicrobial lipids preferably have a hydrophile/lipophile balance (HLB) of at most 6.2, 5.8, or 5.5; and at least 3, 3.2, or at least 3.4.

In certain embodiments, the antimicrobial lipid component includes one or more fatty acid esters of a polyhydric alcohol, fatty ethers of a polyhydric alcohol, or alkoxylated derivatives thereof (of either or both of the ester and ether), or combinations thereof. Typically, the antimicrobial component is selected from the group consisting of a (C7-C14) saturated fatty acid ester of a polyhydric alcohol (preferably (C7-C12) or (C8-C12)), a (C8-C22)unsaturated fatty acid ester of a polyhydric alcohol (preferably (C12-C22)), a (C7-C14)saturated fatty ether of a polyhydric alcohol (preferably (C7-C12) or (C8-C12)), a (C8-C22)unsaturated fatty ether of a polyhydric alcohol (preferably (C12-C22)), an alkoxylated derivative thereof, and combinations thereof. Often, the esters and ethers are monoesters and monoethers. Various combinations of monoesters, diesters, monoethers, and diethers can be used in a polymerizable composition of the present disclosure.

Exemplary fatty acid monoesters include, but are not limited to, glycerol monoesters of lauric (monolaurin), caprylic (monocaprylin), and capric (monocaprin) acid, and propylene glycol monoesters of lauric, caprylic, and capric acid, as well as lauric, caprylic, and capric acid monoesters of sucrose. Other fatty acid monoesters include glycerin and propylene glycol monoesters of oleic (18:1), linoleic (18:2), linolenic (18:3), and arachonic (20:4) unsaturated (including polyunsaturated) fatty acids. As is generally known, 18:1, for example, means the compound has 18 carbon atoms and 1 carbon-carbon double bond. Preferred unsaturated chains have at least one unsaturated group in the cis isomer form. In certain preferred embodiments, the fatty acid monoesters that are suitable for use in the present composition include known monoesters of lauric, caprylic, and capric acid, such as that known as GML or the trade designation LAURICIDIN (the glycerol monoester of lauric acid commonly referred to as monolaurin or glycerol monolaurate), glycerol monocaprate, glycerol monocaprylate, propylene glycol monolaurate, propylene glycol monocaprate, propylene glycol monocaprylate, and combinations thereof.

The antimicrobial lipid is often present in the polymerizable composition in an amount of 0.1 wt. % or greater, 0.5 wt. %, 1 wt. %, 1.5 wt. %, 2 wt. %, 3 wt. %, or 4 wt. % or greater, based on the total weight of the polymerizable composition, and 20 wt. % or less, 15 wt. %, 12 wt. %, 10 wt. %, 8 wt. %, or 5 wt. % or less, based on the total weight of the polymerizable composition.

In some embodiments, an enhancer is also provided to enhance the effectiveness of the antimicrobial lipid, usually acting as a synergist with the antimicrobial lipid. Suitable enhancers include for instance and without limitation, a carboxylic acid (e.g., an alpha-hydroxy acid and/or a beta-hydroxy acid), a phenolic compound (e.g., certain antioxidants and parabens), a monohydroxy alcohol, a chelating agent (e.g., EDTA), a glycol ether (i.e., ether glycol), a surfactant, and combinations thereof. In some embodiments, the presence of a surfactant may be used to emulsify the composition and to help wet the surface and/or to aid in contacting the microorganisms. As used herein, the term "surfactant" means an amphiphile (a molecule possessing both polar and nonpolar regions which are covalently bound) capable of reducing the surface tension of water and/or the interfacial tension between water and an immiscible liquid. The term is meant to include soaps, detergents, emulsifiers, surface active agents, and the like. The surfactant can be cationic, anionic, nonionic, or amphoteric. This includes a wide variety of conventional surfactants. Combinations of various surfactants can be used if desired.

The at least one enhancer may be present in a total amount of 0.01 wt. % or greater, based on the total weight of the polymerizable composition, 0.05 wt. %, 0.1 wt. %, 0.2 wt. %, 0.25 wt. %, or 0.4 wt. % or greater; and 20 wt. % or less, 15 wt. %, 10 wt. %, or 6 wt. % or less, based on the total weight of the polymerizable composition.

Suitable antimicrobial lipids and enhancers are described in detail in U.S. Application Publication 2006/0205838 (Velamakanni et al.), incorporated herein by reference in its entirety.

Combinations of any of the above additives may also be employed. The selection and amount of any one such additive can be selected by one of skill in the art to accomplish the desired result without undue experimentation.

Photopolymerizable compositions materials herein can also exhibit a variety of desirable properties, non-cured, cured, and as post-cured articles. A polymerizable composition, when non-cured, has a viscosity profile consistent with the requirements and parameters of one or more additive manufacturing devices (e.g., 3D printing systems). Advantageously, in many embodiments the polymerizable composition contains a minimal amount of solvent. For instance, the composition may comprise 95% to 100% solids, preferably 100% solids. In some instances, a polymerizable composition described herein when non-cured exhibits a dynamic viscosity of about 0.1-1,000 Pa·s, about 0.1-100 Pa·s, or about 1-10 Pa·s using a TA Instruments AR-G2 magnetic bearing rheometer using a 40 mm cone and plate measuring system at 40 degrees Celsius and at a shear rate of 0.1 l/s. In some cases, a polymerizable composition described herein when non-cured exhibits a dynamic viscosity of less than about 10 Pa·s.

Orthodontic Articles

A polymerized reaction product of a polymerizable composition according to the above disclosure comprises a shape of an orthodontic article. The conformability and durability of a cured orthodontic article made from the polymerizable compositions of the present disclosure can be determined in part by standard tensile, modulus, and/or elongation testing. The polymerizable compositions can typically be characterized by at least one of the following parameters after hardening.

As orthodontic articles are used in the moisture-rich environment of a patient's mouth, the extent of water absorption is relevant to the composition of an orthodontic article. Select articles absorb less than 3%, less than 2.5%, less than 2%, less than 1.5%, or even less than 1% water when soaked in deionized water for 7 days at 37° C.

The orthodontic article preferably exhibits at least one desirable physical property. These physical properties include the following: initial relaxation modulus, elongation at break, tensile strength, relaxation modulus at 30 minutes, percent loss of relaxation modulus, weight percent extractable components, and exhibiting peaks in loss modulus and tan delta with large temperature separation, and percent weight of water absorption. Preferably, the orthodontic article exhibits at least two different desirable physical properties, more preferably at least three different desirable physical properties, and most preferably at least initial relaxation modulus, elongation at break, and tensile strength. The values of these different physical properties are described below.

An orthodontic article optionally exhibits an initial relaxation modulus of 100 megapascals (MPa) or greater measured at 37° C. and 2% strain, as determined by Dynamic Mechanical Analysis (DMA) following conditioning (i.e., soaking) of a sample of the material of the orthodontic article in deionized water for 48 hours at room temperature (i.e., 22 to 25° C.) ("Water Conditioning"). The DMA procedure is described in detail in the Examples below. Preferably, an orthodontic article exhibits an initial relaxation modulus of 200 MPa or greater, 300 MPa or greater, 400 MPa or greater, 500 MPa or greater, 600 MPa or greater, 700 MPa or greater, 800 MPa or greater, 900 MPa or greater, 1,000 MPa or greater, 1,100 MPa or greater, or even 1,200 MPa or greater. In some embodiments, the initial relaxation modulus is no greater than about 3000, 2500, 2000, or 1500 MPa.

An orthodontic article optionally exhibits a (e.g., 30 minute) relaxation modulus of 100 MPa or greater as determined by DMA following 30 minutes of soaking in water at 37° C. under a 2% strain. The DMA procedure for relaxation modulus is described in detail in the Examples below, and is performed on a sample of the material of the orthodontic article following Water Conditioning and initial relaxation modulus testing. Preferably, an orthodontic article exhibits a (e.g., 30 minute) relaxation modulus of 200 MPa or greater, 300 MPa or greater, 400 MPa or greater, 500 MPa or greater, 600 MPa or greater, 700 MPa or greater, 800 MPa or greater, 900 MPa or greater, or even 1,000 MPa or greater. In some embodiments, the (e.g., 30 minute) relaxation modulus is no greater than about 1500, 1200, 1000, or 800 MPa.

An orthodontic article optionally exhibits a percent loss of relaxation modulus of 70% or less as determined by DMA. The loss is determined by comparing the initial relaxation modulus to the (e.g., 30 minute) relaxation modulus at 37° C. and 2% strain. It was discovered that orthodontic articles according to at least certain embodiments of the present disclosure exhibit a smaller loss in relaxation modulus following exposure to water than articles made of different materials. Preferably, an orthodontic article exhibits loss of relaxation modulus of 65% or less, 60% or less, 55% or less, 50% or less, 45% or less 40% or less, or even 35% or less. In some embodiments, the loss of relaxation modulus is 10%, 15%, or 20% or greater.

An orthodontic article optionally exhibits an elongation at break of a printed article of 15% or greater, as determined according to the Examples section below, after conditioning (i.e., soaking) of a sample of the material of the orthodontic article in phosphate-buffered saline having a pH of 7.4, for 24 hours at a temperature of 37° C. ("PBS Conditioning"). High elongation at break helps prevent the orthodontic article from being too brittle and potentially breaking during use by a patient. Preferably, an orthodontic article exhibits an elongation at break of 20% or greater, 25%, 30%, 35%, 40%, 45%, 50%, 55%, 60%, 65%, 70%, 75%, 80%, 85%, 90%, 95%, 100%, 110%, or even 120% or greater. In some embodiments, the elongation at break is no greater than 250%, 240%, 230%, 220%, 210%, 200%, 190%, 180%, 170%, 160%, 150%, or 140%.

Figure 11:
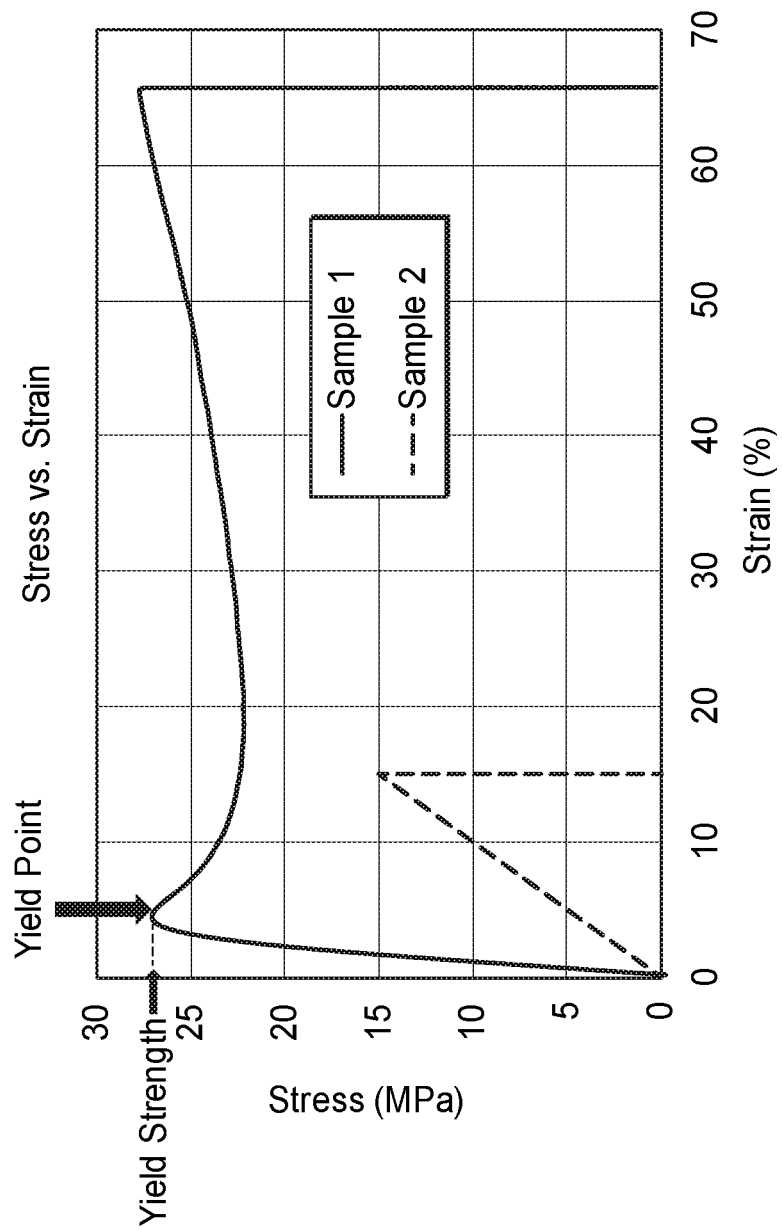
FIG. 11 is a graph of stress-strain curves for two different materials.

An orthodontic article optionally exhibits a tensile strength at yield (or maximum) of 10 MPa or greater as determined according to ASTM-D638-14, using test specimen V, after PBS Conditioning. Strength at yield (i.e., yield strength) is defined as the maximum tensile stress a material can handle before it is permanently deformed. Tensile strength at break refers to the point on the stress-strain curve where the material breaks. Samples that yield can undergo strain hardening by deformation, prior to breaking. The stress strain curves for brittle materials, however, do not have a yield point and are typically linear over the full range of strain, eventually terminating in fracture at a maximum tensile strength without appreciable plastic flow. Referring to FIG. 11, plots of stress-strain are shown of materials having different yield behavior. For instance, Sample 1 has a yield strength of 27 MPa, which is at the yield point on the curve, as well as a tensile strength at break of about 27 MPa. In contrast, Sample 2 does not yield, but has a tensile strength at break of 15 MPa. High tensile strength contributes to the orthodontic article having sufficient strength to be resilient during use in a patient's mouth. Preferably, an orthodontic article exhibits a tensile strength of 12 MPa or greater, 14 MPa, 15 MPa, 17 MPa, 20 MPa, 25 MPa, 30 MPa, 35 MPa, 40 MPa, 45 MPa, 50 MPa, or even 55 MPa or greater. In some embodiments, the tensile strength is no greater than 100 MPa, 95 MPa, 90 MPa, 85 MPa, 80 MPa, 75 MPa, or 70 MPa.

In certain embodiments, a polymerized composition (e.g., an orthodontic article) exhibits an initial relaxation modulus of 100 MPa, an elongation at break of 15% or greater, and a tensile strength of 10 MPa or greater, as determined according to ASTM D638-14 after conditioning in phosphate-buffered saline having a pH of 7.4, for 24 hours at a temperature of 37° C. In select embodiments, an orthodontic article exhibits an initial relaxation modulus of 100 MPa, an elongation at break of 20% or greater, and a tensile strength of 14 MPa or greater. Similarly, an article may exhibit any combination of the preferred values described above, of each of the initial relaxation modulus, elongation at break, and tensile strength at yield. It was unexpectedly found that polymerizable compositions according to at least certain embodiments are capable of forming articles simultaneously having all three of these physical properties.

In select embodiments, dynamic mechanical analysis of articles showed a specific type of response that gave high elongation with high relaxation modulus at 30 minutes. When measured at a frequency of 1 Hz and a temperature heating ramp rate of 2° C./min from below −40° C. to above 200° C., some embodiments according to the present disclosure display a peak in the loss modulus below 20° C., more preferably below 15° C., most preferably below 10° C. In some embodiments, the peak loss modulus temperature is at least −70° C., −60° C., or −50° C. The term peak does not necessarily mean the global maximum value in loss modulus, but can be a local maximum value, or a shoulder on a larger peak. These articles tend to display high levels of elongation at break. In other embodiments, articles may display a tan delta peak >60° C., >80° C., more preferably >100° C., most preferably >110° C. In some embodiments, the peak tan delta temperature is no greater than 150° C., 140° C., 135° C., or 130° C. Articles which displayed high 30 minute relaxation modulus displayed tan delta peaks >60° C. Articles which displayed both high elongation and high 30 minute relaxation modulus displayed a peak in the loss modulus below 20° C. and a tan delta peak greater than 60° C. In some embodiments, an article has a first phase having a peak loss modulus temperature of less than 0, −5, or −10° C. and a second phase having a peak tan delta temperature greater than 30, 40, 50, 60, 70, or 80° C. as determined according to dynamic mechanical analysis after conditioning in deionized water at 37° C. for 24 hours. Loss modulus and tan delta are explained, for instance, in Sepe, M. P. (1998 Dynamic Mechanical Analysis for Plastics Engineering. William Andrew Publishing/Plastics Design Library).

In at least certain embodiments of orthodontic articles of the present disclosure, the articles are advantageously more resistant to staining than articles made from different, more hydrophilic components. For instance, dyes and other colored materials in beverages are typically hydrophilic, thus they will have a greater affinity for a more hydrophilic composition than a more hydrophobic composition.

In certain embodiments, an orthodontic article comprises 2 wt. % or less extractable components, 1 wt. % or less, 0.75 wt. % or less, 0.5 wt. % or less, or even 0.1% or less extractable components, based on the total weight of the article. Either an organic solvent or water can be used to extract component, as described in detail in the Examples below. Post-processing of the orthodontic article to assist in achieving a low extractable component-containing article is discussed in more detail below.

The above mechanical properties are particularly well suited for orthodontic articles that require resiliency and flexibility, along with adequate wear strength and low hygroscopicity.

Methods

In a third aspect, the present disclosure provides a method of making an orthodontic article. The method comprises:
a) obtaining a photopolymerizable composition comprising:
30-65 parts by weight of monofunctional (meth)acrylate monomer(s), wherein a cured homopolymer of at least one monofunctional (meth)acrylate monomer has a $T_g$ of 30° C. or greater; and
at least one urethane (meth)acrylate comprising polymerized units of an aliphatic polycarbonate diol;
b) selectively curing the photopolymerizable composition; and
c) repeating steps a) and b) to form multiple layers and create the orthodontic article.

Polymerizable (e.g., photopolymerizable) compositions described herein can be mixed by known techniques. In some embodiments, for instance, a method for the preparation of a polymerizable composition described herein comprises the steps of mixing all or substantially all of the components of the composition, heating the mixture, and optionally filtering the heated mixture. Softening the mixture, in some embodiments, is carried out at a temperature of about 50° C. or in a range from about 50° C. to about 85° C. In some embodiments, a polymerizable composition described herein is produced by placing all or substantially all components of the composition in a reaction vessel and heating the resulting mixture to a temperature ranging from about 50° C. to about 85° C. with stirring. The heating and stirring are continued until the mixture attains a substantially homogenized state.

In many embodiments, the polymerizable composition is vat polymerized, as discussed in detail below.

The shape of the article is not limited, and typically comprises a shaped integral (e.g., unitary) article, in which more than one variation in dimension is provided by a single integral article. For example, the article can comprise one or more channels, one or more undercuts, one or more perforations, or combinations thereof. Such features are typically not possible to provide in an integral article using conventional molding methods. Specific orthodontic articles are described in further detail below.

The components of the photopolymerizable (e.g., polymerizable) composition are as discussed in detail above. In many embodiments, the photopolymerizable composition is cured using actinic radiation comprising UV radiation, e-beam radiation, visible radiation, or a combination thereof. Moreover, the method optionally further comprises post curing the orthodontic article using actinic radiation.

In certain embodiments, the method comprises vat polymerization of the photopolymerizable composition. When vat polymerization is employed, the radiation may be directed through a wall of a container (e.g., a vat) holding the photopolymerizable composition, such as a side wall or a bottom wall.

A polymerizable composition described herein in a cured state, in some embodiments, can exhibit one or more desired properties. A polymerizable composition in a "cured" state can comprise a polymerizable composition that includes a polymerizable component that has been at least partially polymerized and/or crosslinked. For instance, in some instances, a cured article is at least about 10% polymerized or crosslinked or at least about 30% polymerized or crosslinked. In some cases, a cured polymerizable composition is at least about 50%, at least about 70%, at least about 80%, or at least about 90% polymerized or crosslinked. A cured polymerizable composition can also be between about 10% and about 99% polymerized or crosslinked.

Fabricating an Orthodontic Article

Once prepared as set forth above, the polymerizable (e.g., photopolymerizable) compositions of the present disclosure may be used in myriad additive manufacturing processes to create a variety of e.g., orthodontic articles. A generalized method 100 for creating three-dimensional articles is illustrated in FIG. 1. Each step in the method will be discussed in greater detail below. First, in Step 110 the desired photopolymerizable composition (e.g., comprising at least one polyurethane (meth)acrylate) is provided and introduced into a reservoir, cartridge, or other suitable container for use by or in an additive manufacturing device. The additive manufacturing device selectively cures the photopolymerizable composition according to a set of computerized design instructions in Step 120. In Step 130, Step 110 and/or Step 120 is repeated to form multiple layers to create the article comprising a three-dimensional structure (i.e., an orthodontic article). Optionally uncured photopolymerizable composition is removed from the article in Step 140, further optionally, the article is subjected to additional curing to polymerize remaining uncured photopolymerizable components in the article in Step 150, and yet further optionally, the article is subjected to a heat treatment in Step 160.

Methods of printing a three-dimensional article or object described herein can include forming the article from a plurality of layers of a photopolymerizable composition described herein in a layer-by-layer manner. Further, the layers of a build material composition can be deposited according to an image of the three-dimensional article in a computer readable format. In some or all embodiments, the photopolymerizable composition is deposited according to preselected computer aided design (CAD) parameters.

Additionally, it is to be understood that methods of manufacturing a 3D article described herein can include so-called "stereolithography/vat polymerization" 3D printing methods. Other techniques for three-dimensional manufacturing are known, and may be suitably adapted to use in the applications described herein. More generally, three-dimensional fabrication techniques continue to become available. All such techniques may be adapted to use with photopolymerizable compositions described herein, provided they offer compatible fabrication viscosities and resolutions for the specified article properties. Fabrication may be performed using any of the fabrication technologies described herein, either alone or in various combinations, using data representing a three-dimensional object, which may be reformatted or otherwise adapted as necessary for a particular printing or other fabrication technology.

It is entirely possible to form a 3D article from a photopolymerizable composition described herein using vat polymerization (e.g., stereolithography). For example, in some cases, a method of printing a 3D article comprises retaining a photopolymerizable composition described herein in a fluid state in a container and selectively applying energy to the photopolymerizable composition in the container to solidify at least a portion of a fluid layer of the photopolymerizable composition, thereby forming a hardened layer that defines a cross-section of the 3D article. Additionally, a method described herein can further comprise raising or lowering the hardened layer of photopolymerizable composition to provide a new or second fluid layer of unhardened photopolymerizable composition at the surface of the fluid in the container, followed by again selectively applying energy to the photopolymerizable composition in the container to solidify at least a portion of the new or second fluid layer of the photopolymerizable composition to form a second solidified layer that defines a second cross-section of the 3D article. Further, the first and second cross-sections of the 3D article can be bonded or adhered to one another in the z-direction (or build direction corresponding to the direction of raising or lowering recited above) by the application of the energy for solidifying the photopolymerizable composition. Moreover, selectively applying energy to the photopolymerizable composition in the container can comprise applying actinic radiation, such as UV radiation, visible radiation, or e-beam radiation, having a sufficient energy to cure the photopolymerizable composition. A method described herein can also comprise planarizing a new layer of fluid photopolymerizable composition provided by raising or lowering an elevator platform. Such planarization can be carried out, in some cases, by utilizing a wiper or roller or a recoater. Planarization corrects the thickness of one or more layers prior to curing the material by evening the dispensed material to remove excess material and create a uniformly smooth exposed or flat up-facing surface on the support platform of the printer.

It is further to be understood that the foregoing process can be repeated a selected number of times to provide the 3D article. For example, in some cases, this process can be repeated "n" number of times. Further, it is to be understood that one or more steps of a method described herein, such as a step of selectively applying energy to a layer of photopolymerizable composition, can be carried out according to an image of the 3D article in a computer-readable format. Suitable stereolithography printers include the Viper Pro SLA, available from 3D Systems, Rock Hill, SC and the Asiga PICO PLUS 39, available from Asiga USA, Anaheim Hills, CA.

Figure 2:
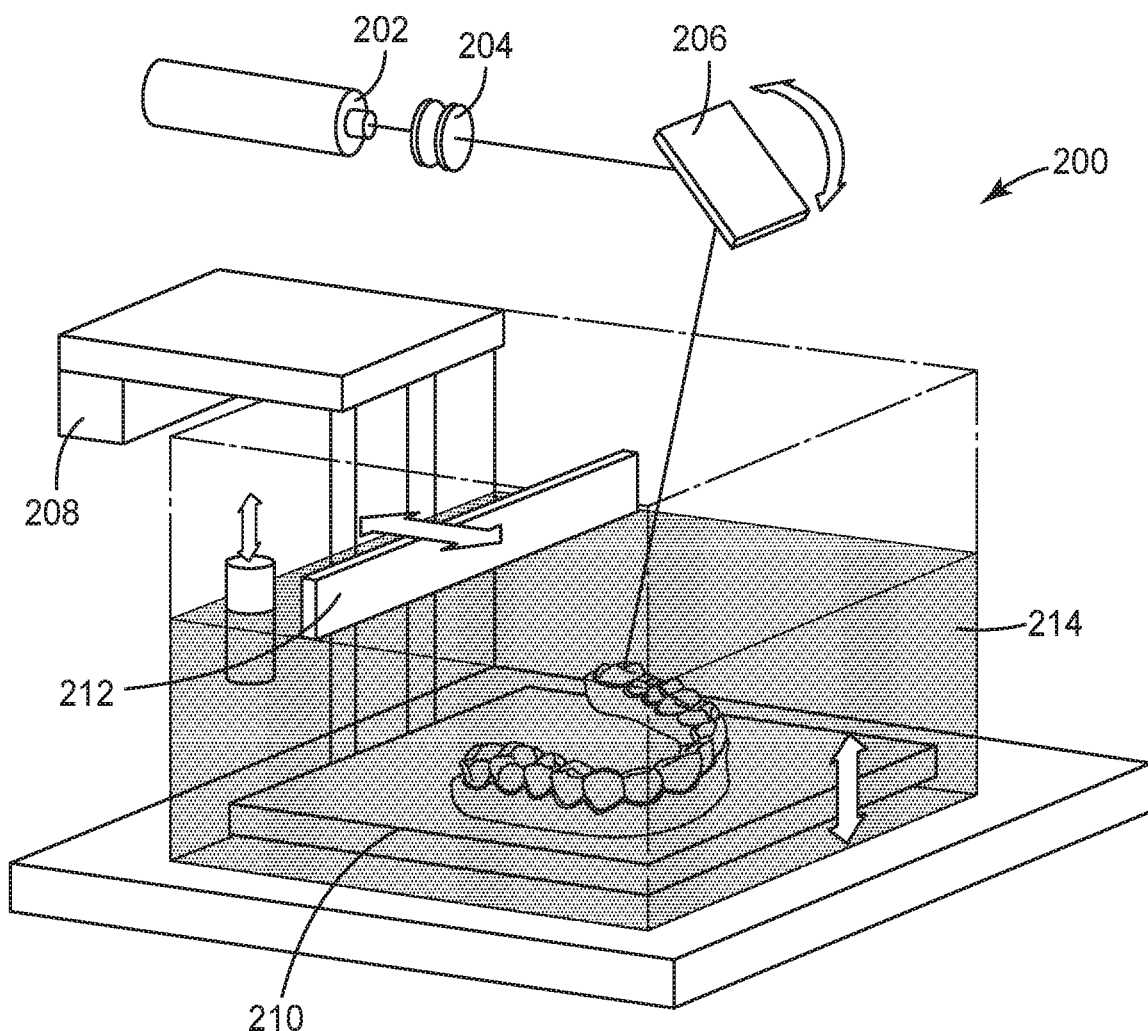
FIG. 2 is a generalized schematic of a stereolithography apparatus.

FIG. 2 shows an exemplary stereolithography apparatus ("SLA") that may be used with the photopolymerizable compositions and methods described herein. In general, the SLA 200 may include a laser 202, optics 204, a steering lens 206, an elevator 208, a platform 210, and a straight edge 212, within a vat 214 filled with the photopolymerizable composition. In operation, the laser 202 is steered across a surface of the photopolymerizable composition to cure a cross-section of the photopolymerizable composition, after which the elevator 208 slightly lowers the platform 210 and another cross section is cured. The straight edge 212 may sweep the surface of the cured composition between layers to smooth and normalize the surface prior to addition of a new layer. In other embodiments, the vat 214 may be slowly filled with liquid resin while an article is drawn, layer by layer, onto the top surface of the photopolymerizable composition.

A related technology, vat polymerization with Digital Light Processing ("DLP"), also employs a container of curable polymer (e.g., photopolymerizable composition). However, in a DLP based system, a two-dimensional cross section is projected onto the curable material to cure the desired section of an entire plane transverse to the projected beam at one time. All such curable polymer systems as may be adapted to use with the photopolymerizable compositions described herein are intended to fall within the scope of the term "vat polymerization system" as used herein. In certain embodiments, an apparatus adapted to be used in a continuous mode may be employed, such as an apparatus commercially available from Carbon 3D, Inc. (Redwood City, CA), for instance as described in U.S. Pat. Nos. 9,205,601 and 9,360,757 (both to DeSimone et al.).

Figure 5:
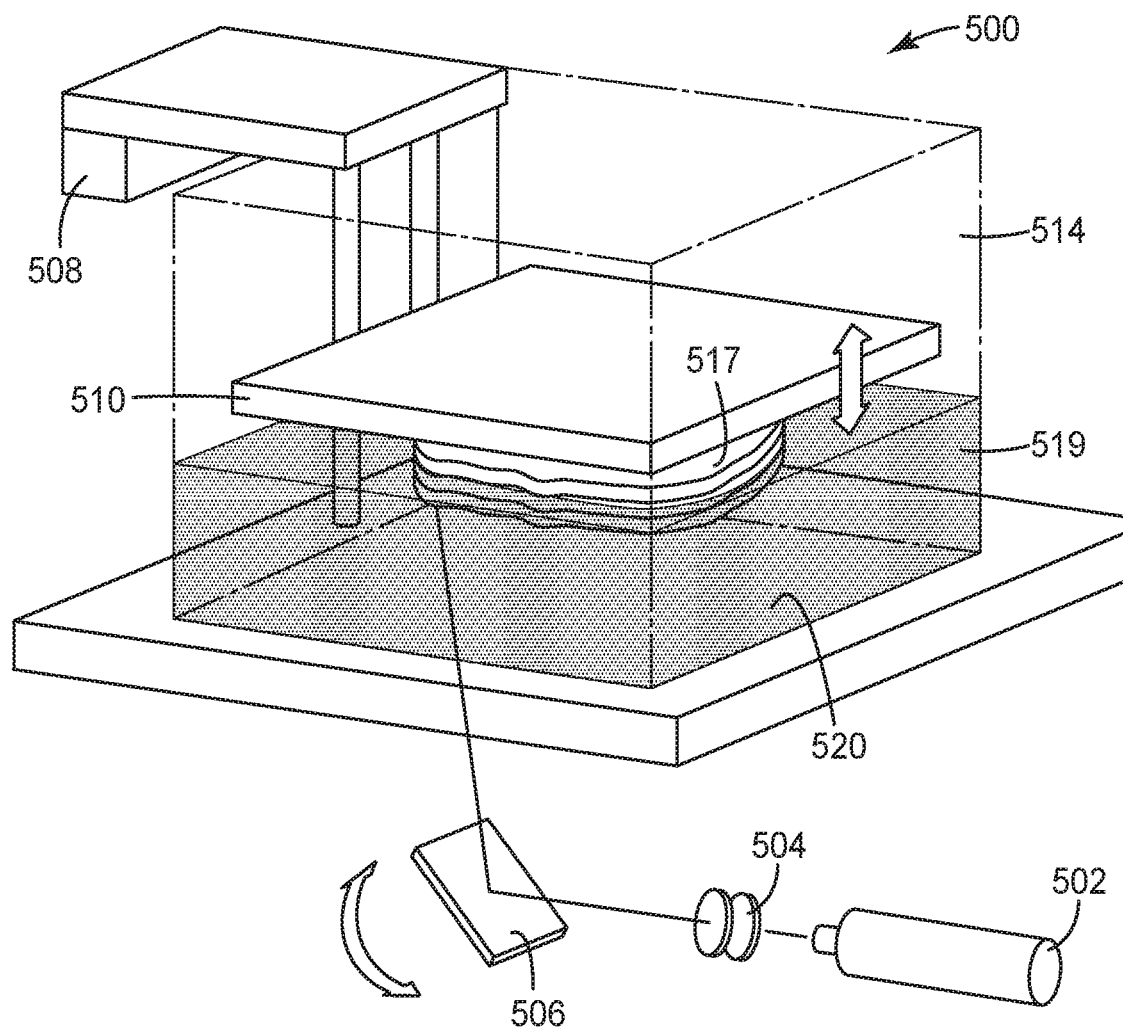
FIG. 5 is a generalized schematic of an apparatus in which radiation is directed through a container.

Referring to FIG. 5, a general schematic is provided of another SLA apparatus that may be used with photopolymerizable compositions and methods described herein. In general, the apparatus 500 may include a laser 502, optics 504, a steering lens 506, an elevator 508, and a platform 510, within a vat 514 filled with the photopolymerizable composition 519. In operation, the laser 502 is steered through a wall 520 (e.g., the floor) of the vat 514 and into the photopolymerizable composition to cure a cross-section of the photopolymerizable composition 519 to form an article 517, after which the elevator 508 slightly raises the platform 510 and another cross section is cured.

More generally, the photopolymerizable composition is typically cured using actinic radiation, such as UV radiation, e-beam radiation, visible radiation, or any combination thereof. The skilled practitioner can select a suitable radiation source and range of wavelengths for a particular application without undue experimentation.

After the 3D article has been formed, it is typically removed from the additive manufacturing apparatus and rinsed, (e.g., an ultrasonic, or bubbling, or spray rinse in a solvent, which would dissolve a portion of the uncured photopolymerizable composition but not the cured, solid state article (e.g., green body). Any other conventional method for cleaning the article and removing uncured material at the article surface may also be utilized. At this stage, the three-dimensional article typically has sufficient green strength for handling in the remaining optional steps of method 100.

It is expected in certain embodiments of the present disclosure that the formed article obtained in Step 120 will shrink (i.e., reduce in volume) such that the dimensions of the article after (optional) Step 150 will be smaller than expected. For example, a cured article may shrink less than 5% in volume, less than 4%, less than 3%, less than 2%, or even less than 1% in volume, which is contrast to other compositions that provide articles that shrink about 6-8% in volume upon optional post curing. The amount of volume percent shrinkage will not typically result in a significant distortion in the shape of the final object. It is particularly contemplated, therefore, that dimensions in the digital representation of the eventual cured article may be scaled according to a global scale factor to compensate for this shrinkage. For example, in some embodiments, at least a portion of the digital article representation can be at least 101% of the desired size of the printed appliance, in some embodiments at least 102%, in some embodiments at least 104%, in some embodiments, at least 105%, and in some embodiments, at least 110%.

A global scale factor may be calculated for any given photopolymerizable composition formulation by creating a calibration part according to Steps 110 and 120 above. The dimensions of the calibration article can be measured prior to post curing.

In general, the three-dimensional article formed by initial additive manufacturing in Step 120, as discussed above, is not fully cured, by which is meant that not all of the photopolymerizable material in the composition has polymerized even after rinsing. Some uncured photopolymerizable material is typically removed from the surface of the printed article during a cleaning process (e.g., optional Step 140). The article surface, as well as the bulk article itself, typically still retains uncured photopolymerizable material, suggesting further cure. Removing residual uncured photopolymerizable composition is particularly useful when the article is going to subsequently be post cured, to minimize uncured residual photopolymerizable composition from undesirably curing directly onto the article.

Further curing can be accomplished by further irradiating with actinic radiation, heating, or both. Exposure to actinic radiation can be accomplished with any convenient radiation source, generally UV radiation, visible radiation, and/or e-beam radiation, for a time ranging from about 10 to over 60 minutes. Heating is generally carried out at a temperature in the range of about 75-150° C., for a time ranging from about 10 to over 60 minutes in an inert atmosphere. So called post cure ovens, which combine UV radiation and thermal energy, are particularly well suited for use in the post cure processes of Step 150 and/or Step 160. In general, post curing improves the mechanical properties and stability of the three-dimensional article relative to the same three-dimensional article that is not post cured.

One particularly attractive opportunity for 3D printing is in the direct creation of orthodontic clear tray aligners. These trays, also known as aligners or polymeric or shell appliances, are provided in a series and are intended to be worn in succession, over a period of months, in order to gradually move the teeth in incremental steps towards a desired target arrangement. Some types of clear tray aligners have a row of tooth-shaped receptacles for receiving each tooth of the patient's dental arch, and the receptacles are oriented in slightly different positions from one appliance to the next in order to incrementally urge each tooth toward its desired target position by virtue of the resilient properties of the polymeric material. A variety of methods have been proposed in the past for manufacturing clear tray aligners and other resilient appliances. Typically, positive dental arch models are fabricated for each dental arch using additive manufacturing methods such as stereolithography described above. Subsequently, a sheet of polymeric material is placed over each of the arch models and formed under heat, pressure and/or vacuum to conform to the model teeth of each model arch. The formed sheet is cleaned and trimmed as needed and the resulting arch-shaped appliance is shipped along with the desired number of other appliances to the treating professional.

An aligner or other resilient appliance created directly by 3D printing would eliminate the need to print a mold of the dental arch and further thermoform the appliance. It also would allow new aligner designs and give more degrees of freedom in the treatment plan. Exemplary methods of direct printing clear tray aligners and other resilient orthodontic apparatuses are set forth in PCT Publication Nos. WO2016/109660 (Raby et al.), WO2016/148960 (Cinader et al.), and WO2016/149007 (Oda et al.) as well as US Publication Nos. US2011/0091832 (Kim, et al.) and US2013/0095446 (Kitching).

The following describes general methods for creating a clear tray aligner as printed appliance 300. However, other dental and orthodontic articles can be created using similar techniques and the photopolymerizable compositions of the present disclosure. Representative examples include, but are not limited to, the removable appliances having occlusal windows described in International Application Publication No. WO2016/109660 (Raby et al.), the removable appliances with a palatal plate described in US Publication No. 2014/0356799 (Cinader et al); the resilient polymeric arch members described in International Application Nos. WO2016/148960 and WO2016/149007 (Oda et al.) as well as US Publication No. 2008/0248442 (Cinader et al.); and molding techniques and tools for forming a dental restoration in a mouth as described in WO2016/094272 (Hansen et al.) and US Publication No. 2019/0083208 (Hansen et al.). Moreover, the photopolymerizable compositions can be used in the creation of indirect bonding trays, such as those described in International Publication No. WO2015/094842 (Paehl et al.) and US Publication No. 2011/0091832 (Kim, et al.) and other dental articles, including but not limited to crowns, bridges, veneers, inlays, onlays, fillings, and prostheses (e.g., partial or full dentures). Other orthodontic appliances and devices include, but not limited to, orthodontic brackets, buccal tubes, lingual retainers, orthodontic bands, class II and class III correctors, sleep apnea devices, bite openers, buttons, cleats, and other attachment devices.

Fabricating an Orthodontic Appliance with the Polymerizable Compositions

Figure 3:
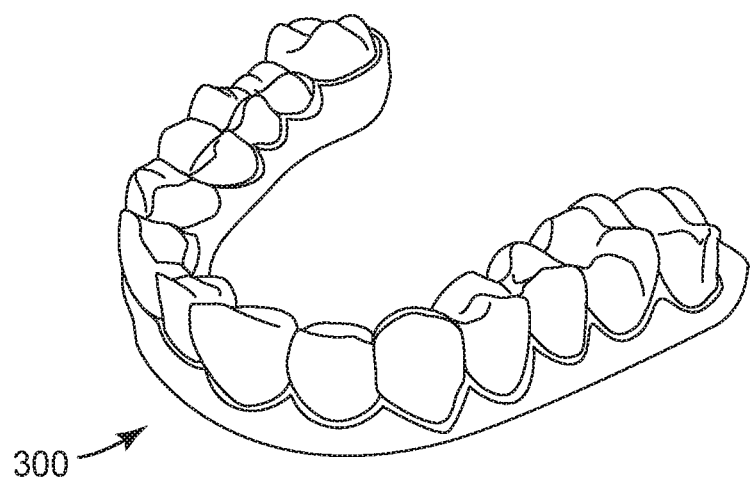
FIG. 3 is an isometric view of a printed clear tray aligner, according to one embodiment of the present disclosure.

One particularly interesting implementation of an article is generally depicted in FIG. 3. The additive manufactured article 300 is a clear tray aligner and is removably positionable over some or all of a patient's teeth. In some embodiments, the appliance 300 is one of a plurality of incremental adjustment appliances. The appliance 300 may comprise a shell having an inner cavity. The inner cavity is shaped to receive and resiliently reposition teeth from one tooth arrangement to a successive tooth arrangement. The inner cavity may include a plurality of receptacles, each of which is adapted to connect to and receive a respective tooth of the patient's dental arch. The receptacles are spaced apart from each other along the length of the cavity, although adjoining regions of adjacent receptacles can be in communication with each other. In some embodiments, the shell fits over all teeth present in the upper jaw or lower jaw. Typically, only certain one(s) of the teeth will be repositioned while others of the teeth will provide a base or anchor region for holding the dental appliance in place as it applies the resilient repositioning force against the tooth or teeth to be treated.

In order to facilitate positioning of the teeth of the patient, at least one of the receptacles may be aligned to apply rotational and/or translational forces to the corresponding tooth of the patient when the appliance 300 is worn by the patient in order to eventually align said tooth to a new desired position. In some particular examples, the appliance 300 may be configured to provide only compressive or linear forces. In the same or different examples, the appliance 300 may be configured to apply translational forces to one or more of the teeth within receptacles.

In some embodiments, the shell of the appliance 300 fits over some or all anterior teeth present in an upper jaw or lower jaw. Typically, only certain one(s) of the teeth will be repositioned while others of the teeth will provide a base or anchor region for holding the appliance in place as it applies the resilient repositioning force against the tooth or teeth to be repositioned. An appliance 300 can accordingly be designed such that any receptacle is shaped to facilitate retention of the tooth in a particular position in order to maintain the current position of the tooth.

Figure 4:
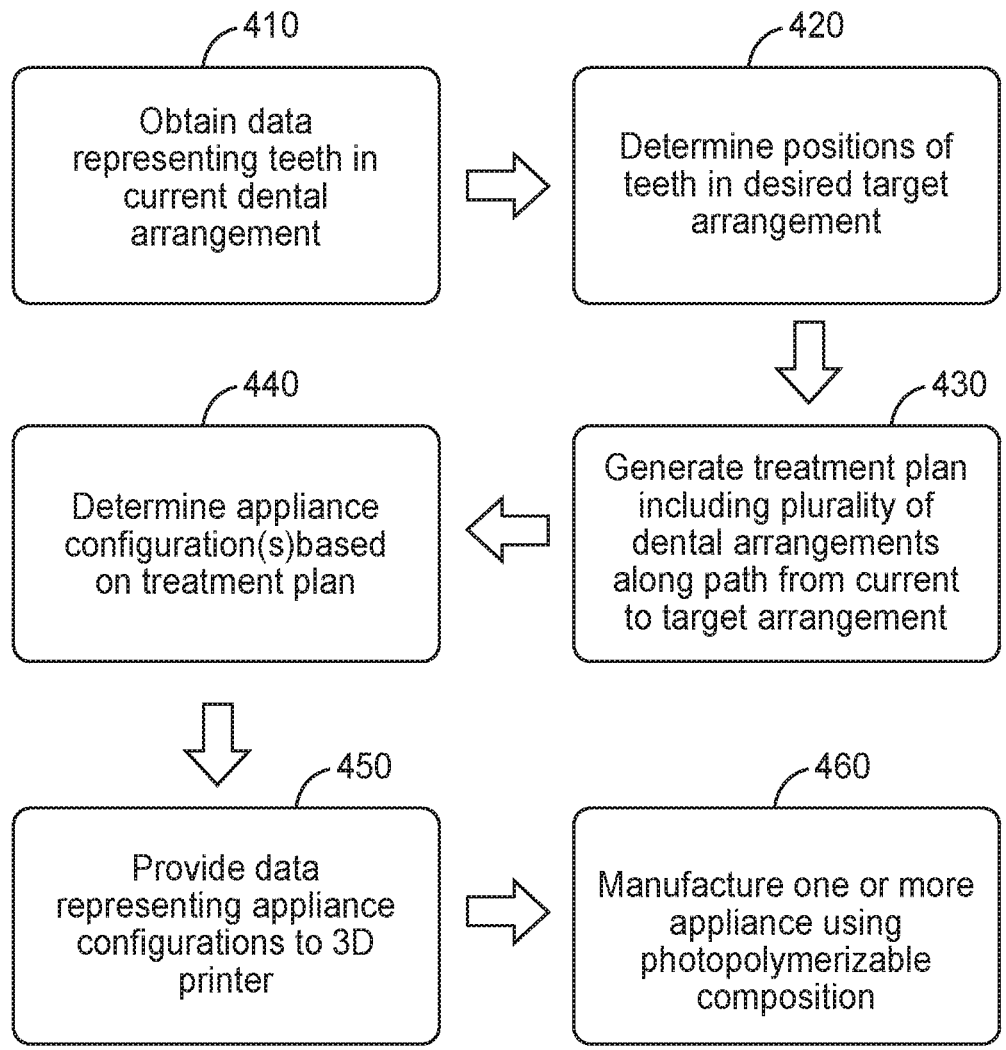
FIG. 4 is a flowchart of a process for manufacturing a printed orthodontic appliance according to the present disclosure.

A method 400 of creating an orthodontic appliance using the photopolymerizable compositions of the present disclosure can include general steps as outlined in FIG. 4. Individual aspects of the process are discussed in further detail below. The process includes generating a treatment plan for repositioning a patient's teeth. Briefly, a treatment plan can include obtaining data representing an initial arrangement of the patient's teeth (Step 410), which typically includes obtaining an impression or scan of the patient's teeth prior to the onset of treatment. The treatment plan will also include identifying a final or target arrangement of the patient's anterior and posterior teeth as desired (Step 420), as well as a plurality of planned successive or intermediary tooth arrangements for moving at least the anterior teeth along a treatment path from the initial arrangement toward the selected final or target arrangement (Step 430). One or more appliances can be virtually designed based on the treatment plan (Step 440), and image data representing the appliance designs can exported in STL format, or in any other suitable computer processable format, to an additive manufacturing device (e.g., a 3D printer system) (Step 450). An appliance can be manufactured using a photopolymerizable composition of the present disclosure retained in the additive manufacturing device (Step 460).

In some embodiments, a (e.g., non-transitory) machine-readable medium is employed in additive manufacturing of articles according to at least certain aspects of the present disclosure. Data is typically stored on the machine-readable medium. The data represents a three-dimensional model of an article, which can be accessed by at least one computer processor interfacing with additive manufacturing equipment (e.g., a 3D printer, a manufacturing device, etc.). The data is used to cause the additive manufacturing equipment to create an article comprising a reaction product of a photopolymerizable composition, the photopolymerizable composition includes a blend of 30-65 parts by weight of monofunctional (meth)acrylate monomer(s) and at least one urethane (meth)acrylate including polymerized units of an aliphatic polycarbonate diol. A cured homopolymer of at least one monofunctional (meth)acrylate monomer has a $T_g$ of 30 degrees Celsius (° C.) or greater. The polymerized reaction product of the photopolymerizable composition has a shape of the orthodontic article. The details of the photopolymerizable composition are as described above.

Data representing an article may be generated using computer modeling such as computer aided design (CAD) data. Image data representing the (e.g., polymeric) article design can be exported in STL format, or in any other suitable computer processable format, to the additive manufacturing equipment. Scanning methods to scan a three-dimensional object may also be employed to create the data representing the article. One exemplary technique for acquiring the data is digital scanning. Any other suitable scanning technique may be used for scanning an article, including X-ray radiography, laser scanning, computed tomography (CT), magnetic resonance imaging (MRI), and ultrasound imaging. Other possible scanning methods are described, e.g., in U.S. Patent Application Publication No. 2007/0031791 (Cinader, Jr., et al.). The initial digital data set, which may include both raw data from scanning operations and data representing articles derived from the raw data, can be processed to segment an article design from any surrounding structures (e.g., a support for the article). In select embodiments, scanning techniques may include, for example, scanning a patient's mouth to customize an orthodontic article for the patient.

Figure 10:
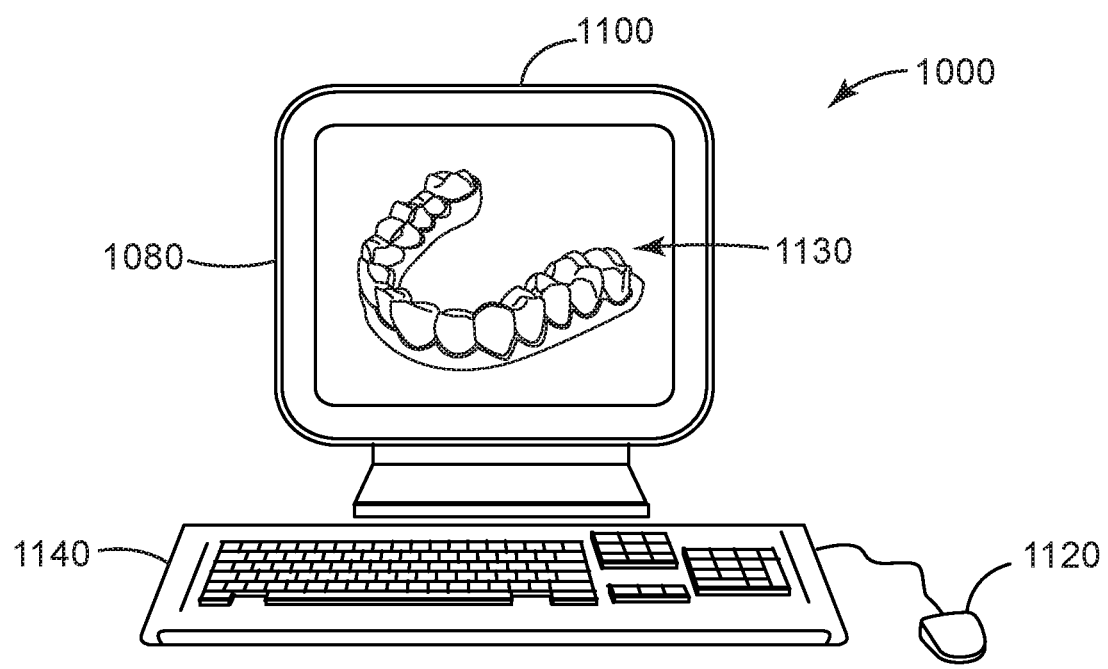
FIG. 10 is a schematic front view of an exemplary computing device 1000.

Often, machine-readable media are provided as part of a computing device. The computing device may have one or more processors, volatile memory (RAM), a device for reading machine-readable media, and input/output devices, such as a display, a keyboard, and a pointing device. Further, a computing device may also include other software, firmware, or combinations thereof, such as an operating system and other application software. A computing device may be, for example, a workstation, a laptop, a personal digital assistant (PDA), a server, a mainframe or any other general-purpose or application-specific computing device. A computing device may read executable software instructions from a computer-readable medium (such as a hard drive, a CD-ROM, or a computer memory), or may receive instructions from another source logically connected to computer, such as another networked computer. Referring to FIG. 10, a computing device 1000 often includes an internal processor 1080, a display 1100 (e.g., a monitor), and one or more input devices such as a keyboard 1140 and a mouse 1120. In FIG. 10, an aligner article 1130 is shown on the display 1100.

Figure 6:
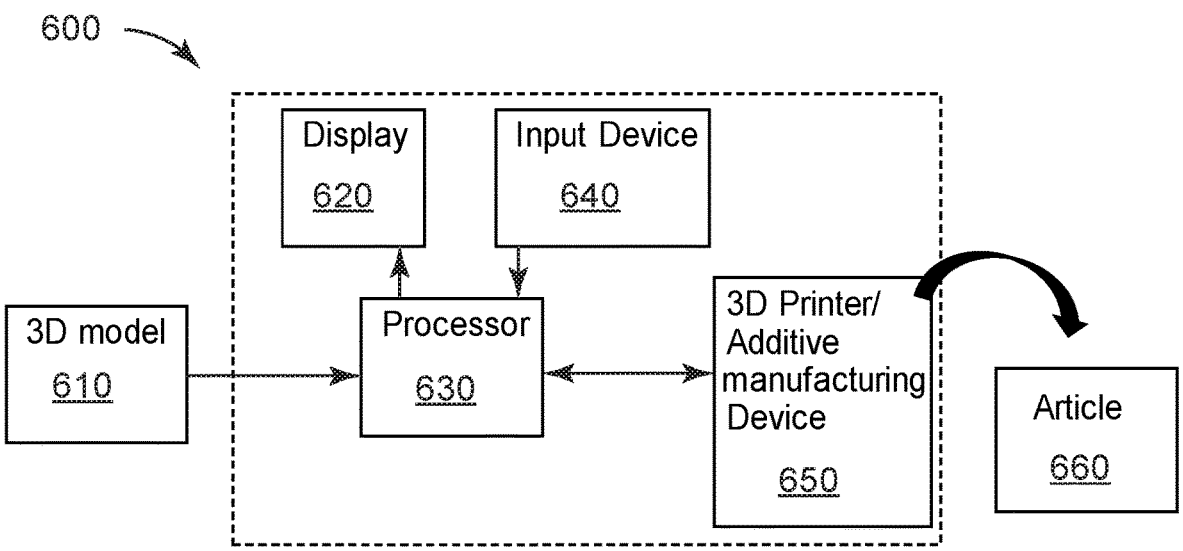
FIG. 6 is a block diagram of a generalized system 600 for additive manufacturing of an article.

Referring to FIG. 6, in certain embodiments, the present disclosure provides a system 600. The system 600 comprises a display 620 that displays a 3D model 610 of an article (e.g., an aligner 1130 as shown on the display 1100 of FIG. 10); and one or more processors 630 that, in response to the 3D model 610 selected by a user, cause a 3D printer/additive manufacturing device 650 to create a physical object of the article 660. Often, an input device 640 (e.g., keyboard and/or mouse) is employed with the display 620 and the at least one processor 630, particularly for the user to select the 3D model 610. The article 660 comprises a reaction product of a photopolymerizable composition, the photopolymerizable composition includes a blend of 30-65 parts by weight of monofunctional (meth)acrylate monomer(s) and at least one urethane (meth)acrylate including polymerized units of an aliphatic polycarbonate diol. A cured homopolymer of at least one monofunctional (meth)acrylate monomer has a $T_g$ of 30 degrees Celsius (° C.) or greater. The polymerized reaction product of the photopolymerizable composition has a shape of the orthodontic article. The details of the photopolymerizable composition are as described above.

Figure 7:
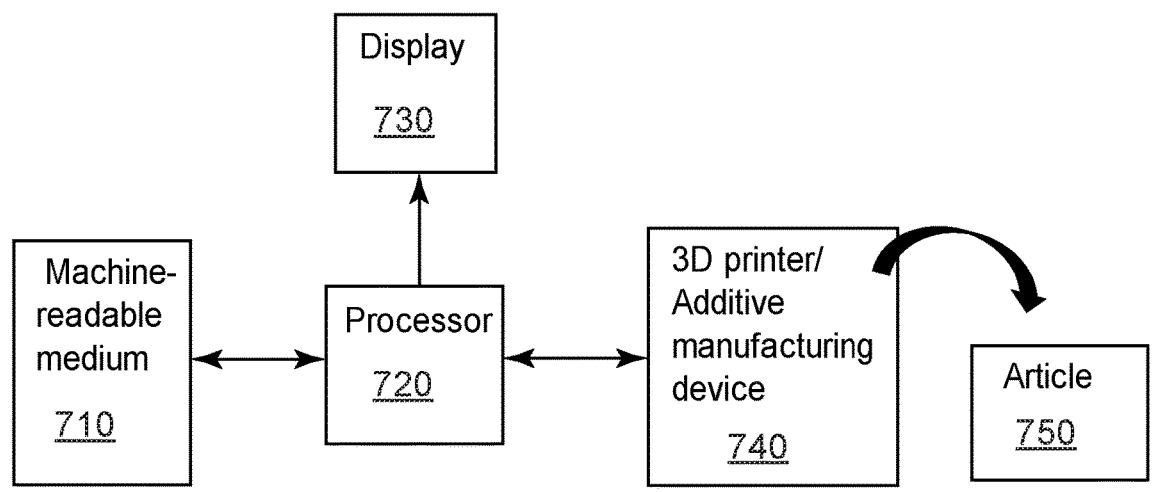
FIG. 7 is a block diagram of a generalized manufacturing process for an article.

Referring to FIG. 7, a processor 720 (or more than one processor) is in communication with each of a machine-readable medium 710 (e.g., a non-transitory medium), a 3D printer/additive manufacturing device 740, and optionally a display 730 for viewing by a user. The 3D printer/additive manufacturing device 740 is configured to make one or more articles 750 based on instructions from the processor 720 providing data representing a 3D model of the article 750 (e.g., an aligner article 1130 as shown on the display 1100 of FIG. 10) from the machine-readable medium 710.

Figure 8:
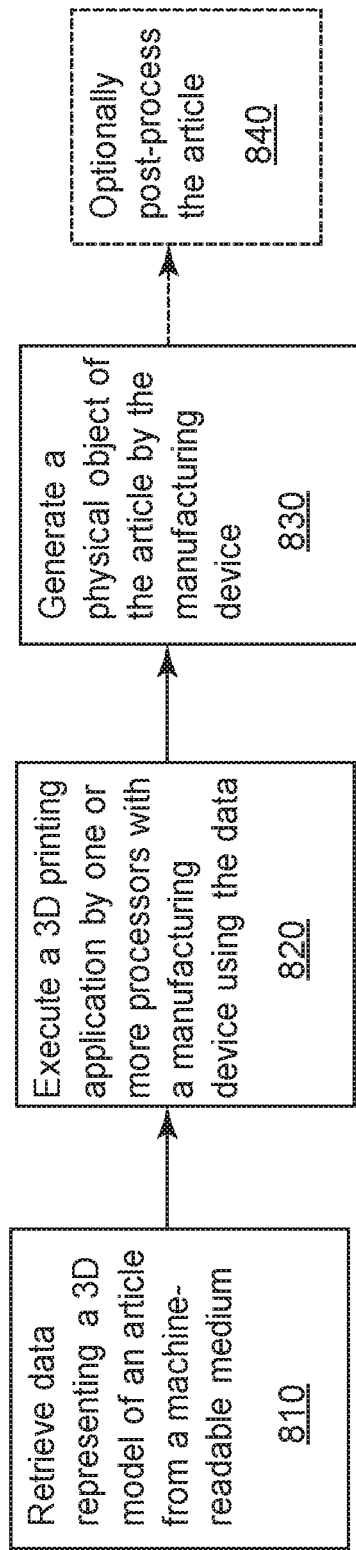
FIG. 8 is a high-level flow chart of an exemplary article manufacturing process.

Referring to FIG. 8, for example and without limitation, an additive manufacturing method comprises retrieving 810, from a (e.g., non-transitory) machine-readable medium, data representing a 3D model of an article according to at least one embodiment of the present disclosure. The method further includes executing 820, by one or more processors, an additive manufacturing application interfacing with a manufacturing device using the data; and generating 830, by the manufacturing device, a physical object of the article. The additive manufacturing equipment can selectively cure a photopolymerizable composition to form an article. The article comprises a reaction product of a photopolymerizable composition, the photopolymerizable composition includes a blend of 30-65 parts by weight of monofunctional (meth)acrylate monomer(s) and at least one urethane (meth)acrylate including polymerized units of an aliphatic polycarbonate diol. A cured homopolymer of at least one monofunctional (meth)acrylate monomer has a $T_g$ of 30 degrees Celsius (° C.) or greater. The polymerized reaction product of the photopolymerizable composition has a shape of the orthodontic article. The details of the photopolymerizable composition are as described above. One or more various optional post-processing steps 840 may be undertaken. Typically, remaining unpolymerized photopolymerizable component may be cured. The article comprises an orthodontic article.

Figure 9:
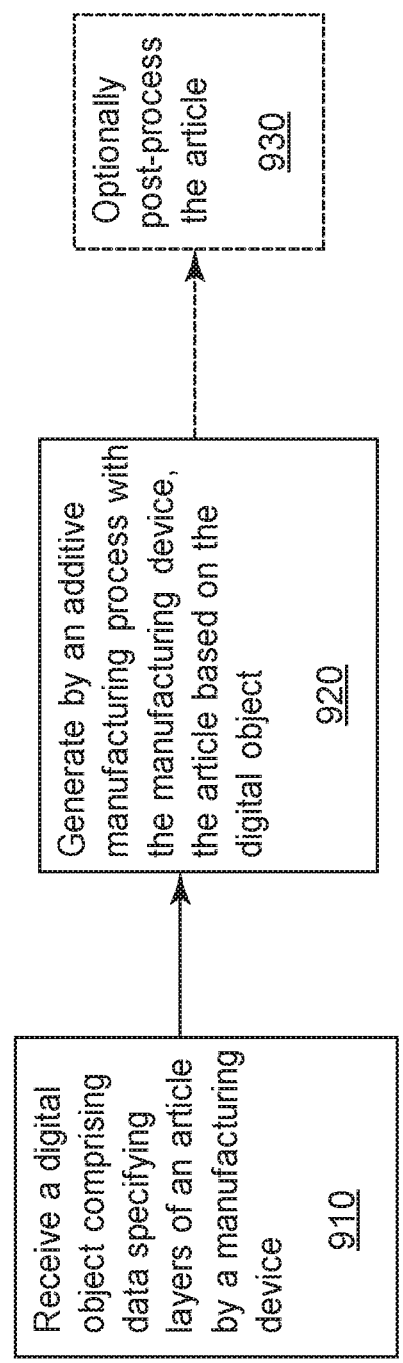
FIG. 9 is a high-level flow chart of an exemplary article additive manufacturing process.

Additionally, referring to FIG. 9, a method of making an article comprises receiving 910, by a manufacturing device having one or more processors, a digital object comprising data specifying a plurality of layers of an article; and generating 920, with the manufacturing device by an additive manufacturing process, the article based on the digital object. Again, the article may undergo one or more steps of post-processing 930.

Select Embodiments of the Disclosure

Embodiment 1 is an orthodontic article. The orthodontic article includes a reaction product of a polymerizable composition. The polymerizable composition includes 30-65 parts by weight of monofunctional (meth)acrylate monomer(s) and at least one urethane (meth)acrylate including polymerized units of an aliphatic polycarbonate diol. A cured homopolymer of at least one monofunctional (meth)acrylate monomer has a $T_g$ of 30 degrees Celsius (° C.) or greater.

Embodiment 2 is the orthodontic article of embodiment 1, wherein the at least one urethane (meth)acrylate and the monofunctional (meth)acrylate monomer(s) are present at a weight ratio ranging from 2:1 to 1:2.

Embodiment 3 is the orthodontic article of embodiment 1 or embodiment 2, wherein the monofunctional (meth)acrylate monomer(s) having a $T_g$ of at least 30° C. has a log P value of greater than 1, 1.5, 2, 2.5, or 3.

Embodiment 4 is the orthodontic article of any of embodiments 1 to 3, wherein the monofunctional (meth)acrylate monomer(s) having a $T_g$ of at least 30° C. are present in an amount of at least 15, 20, 25, 30, 35, 40, 45, or 50 wt. %, based on the total weight of the organic components of the composition.

Embodiment 5 is the orthodontic article of any of embodiments 1 to 4, wherein the at least one monofunctional (meth)acrylate monomer(s) have a $T_g$ of at least 40, 50, 60, 70, 80, or 90° C.

Embodiment 6 is the orthodontic article of any of embodiments 1 to 5, wherein at least one monofunctional (meth)acrylate monomer having a $T_g$ of at least 30° C. comprises a cycloaliphatic group.

Embodiment 7 is the orthodontic article of any of embodiments 1 to 6, wherein the at least one urethane (meth)acrylate includes a reaction product of an aliphatic polycarbonate diol, a diisocyanate, and a hydroxy functional (meth)acrylate.

Embodiment 8 is the orthodontic article of embodiment 7, wherein the hydroxy functional (meth)acrylate is of Formula (II):

$$HO-Q-(A)_p \quad (II),$$

wherein Q is a polyvalent organic linking group and A is a (meth)acryl functional group of the formula —XC(=O)C(R)=CH$_2$, wherein X is O, S, or NR$_4$, R$_4$ is H or alkyl of 1 to 4 carbon atoms, R$_1$ is a lower alkyl of 1 to 4 carbon atoms or H, and p is 1 or 2.

Embodiment 9 is the orthodontic article of embodiment 7 or embodiment 8, wherein the at least one urethane (meth)acrylate is of Formula (VI):

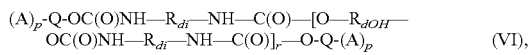

$$(A)_p-Q-OC(O)NH-R_{di}-NH-C(O)-[O-R_{dOH}-OC(O)NH-R_{di}-NH-C(O)]_r-O-Q-(A)_p \quad (VI),$$

wherein A has the formula —XC(=O)C(R$_1$)=CH$_2$, wherein X is O, S, or NR$_4$, R$_4$ is H or alkyl of 1 to 4 carbon atoms, and $R_1$ is a lower alkyl of 1 to 4 carbon atoms or H, p is 1 or 2, Q is a polyvalent organic linking group, $R_{di}$ is the residue of a diisocyanate, $R_{dOH}$ is the residue of a polycarbonate polyol, and r averages from 1 to 15.

Embodiment 10 is the orthodontic article of any of embodiments 1 to 9, wherein the at least one urethane (meth)acrylate includes a reaction product of an aliphatic polycarbonate diol, a diisocyanate, a diol (meth)acrylate, and a hydroxy functional (meth)acrylate.

Embodiment 11 is the orthodontic article of embodiment 10, wherein the at least one urethane (meth)acrylate is of Formula (V):

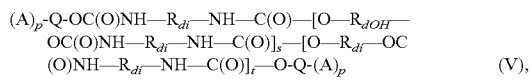
(V), wherein A has the formula —XC(=O)C($R_1$)=CH$_2$, wherein X is O, S, or NR$_4$, $R_4$ is H or alkyl of 1 to 4 carbon atoms, and $R_1$ is a lower alkyl of 1 to 4 carbon atoms or H, p is 1 or 2, Q is a polyvalent organic linking group, $R_{di}$ is the residue of a diisocyanate, $R_{dOH}$ is the residue of a polycarbonate polyol, s and t are independently 1 or greater, and s+t averages from 2 to 15, wherein the s and t units may be connected to each other in any order, wherein $R_{AD}$ is the residue of a (meth)acrylated diol.

Embodiment 12 is the orthodontic article of any of embodiments 1 to 11, wherein the at least one urethane (meth)acrylate includes a reaction product of an aliphatic polycarbonate diol and an isocyanate functional (meth)acrylate.

Embodiment 13 is the orthodontic article of claim 12, wherein the at least one urethane (meth)acrylate is of Formula (VIII):

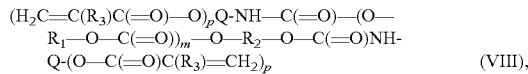
(VIII), wherein Q is a polyvalent organic linking group, $R_3$ is a lower alkyl of 1 to 4 carbon atoms or H, p is 1 or 2, each $R_1$ and $R_2$ are independently an aliphatic, cycloaliphatic, or aliphatic/cycloaliphatic alkylene group and an average number of carbon atoms in a combination of all the $R_1$ and $R_2$ groups is 4 to 10, and m is 2 to 23.

Embodiment 14 is the orthodontic article of any of embodiments 1 to 13, wherein the at least one urethane (meth)acrylate includes a reaction product of an aliphatic polycarbonate diol, a diisocyanate, and an isocyanate functional (meth)acrylate.

Embodiment 15 is the orthodontic article of embodiment 14, wherein the at least one urethane (meth)acrylate is of Formula (XI):

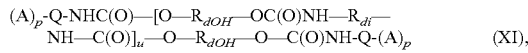
(XI)

wherein u is 0 to 15, A has the formula —XC(=O)C($R_1$)=CH$_2$, wherein X is O, S, or NR$_4$, $R_4$ is H or alkyl of 1 to 4 carbon atoms, and $R_1$ is a lower alkyl of 1 to 4 carbon atoms or H, p is 1 or 2, Q is a polyvalent organic linking group, $R_{di}$ is the residue of a diisocyanate, and $R_{dOH}$ is the residue of a polycarbonate polyol.

Embodiment 16 is the orthodontic article of any of embodiments 1 to 15, wherein the at least one urethane (meth)acrylate includes a reaction product of an aliphatic polycarbonate diol, a diisocyanate, a diol (meth)acrylate, and an isocyanate functional (meth)acrylate.

Embodiment 17 is the orthodontic article of embodiment 16, wherein the at least one urethane (meth)acrylate is of Formula (XII):

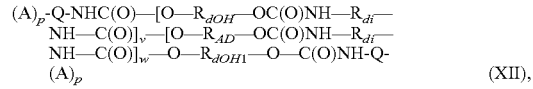
(XII), wherein $R_{di}$, $R_{AD}$, Q, A, and p, are defined as above, v+w is 1 to 15, and $R_{dOH1}$ is selected from $R_{dOH}$ or $R_{AD}$, with the provisos that if v is 0 then $R_{dOH1}$ is $R_{dOH}$, and if w is 0 then $R_{dOH1}$ is $R_{AD}$.

Embodiment 18 is the orthodontic article of any of embodiments 1 to 12, wherein the at least one urethane (meth)acrylate further includes polymerized units of a polyester diol, wherein the urethane (meth)acrylate contains the same or more polymerized units of the aliphatic polycarbonate diol than the polyester diol.

Embodiment 19 is the orthodontic article of embodiment 18, wherein the at least one urethane (meth)acrylate is of Formula (XIII):

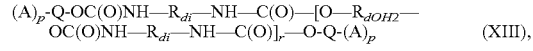
(XIII), wherein each $R_{dOH2}$ is independently selected from the residue of a polyester polyol or the residue of a polycarbonate polyol, with the proviso that x is greater than 2.

Embodiment 20 is the orthodontic article of any of embodiments 1 to 19, wherein the polymerizable composition further includes at least one urethane (meth)acrylate lacking aliphatic polycarbonate moieties.

Embodiment 21 is the orthodontic article of any of embodiments 1 to 20, wherein the polymerizable composition further includes a urethane (meth)acrylate comprising polymerized units of a polyester diol, wherein the urethane (meth)acrylate comprising polymerized units of a polyester diol is present in an amount no more than the amount present of the at least one urethane (meth)acrylate including polymerized units of an aliphatic polycarbonate diol.

Embodiment 22 is the orthodontic article of embodiment 21, wherein the at least one urethane (meth)acrylate including polymerized units of a polyester diol is of Formula (XIII) or Formula (XIV):

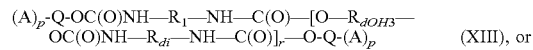
(XIII), or

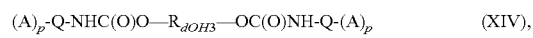
(XIV), wherein A has the formula —XC(=O)C(R)=CH$_2$, wherein X is O, S, or NR$_4$, $R_4$ is H or alkyl of 1 to 4 carbon atoms, and $R_1$ is a lower alkyl of 1 to 4 carbon atoms or H, p is 1 or 2, Q is a polyvalent organic linking group, $R_{di}$ is a residue of a diisocyanate, $R_{dOH3}$ is a residue of a polyester polyol, and r averages from 1 to 15.

Embodiment 23 is the orthodontic article of any of embodiments 1 to 22, wherein the aliphatic polycarbonate diol is of Formula (I):

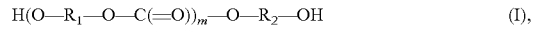
(I), wherein each of $R_1$ in each (O—$R_1$—O—C(=O)) repeat unit and each $R_2$ are independently an aliphatic, cycloaliphatic, or aliphatic/cycloaliphatic alkylene group and an average number of carbon atoms in a combination of all the $R_1$ and $R_2$ groups is 4 to 10, and m is 2 to 23.

Embodiment 24 is the orthodontic article of any of embodiments 1 to 23, wherein the polymerizable composition further includes a compound of Formula (III):

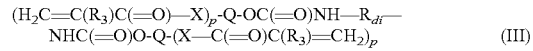
(III)

wherein Q is a polyvalent organic linking group, X is O, S, or NR$_4$, $R_4$ is H or alkyl of 1 to 4 carbon atoms, $R_3$ is a lower alkyl of 1 to 4 carbon atoms or H, p is 1 or 2, and $R_{di}$ is the residue of a diisocyanate.

Embodiment 25 is the orthodontic article of embodiment 24, wherein the compound of Formula (III) is of Formula (IV):

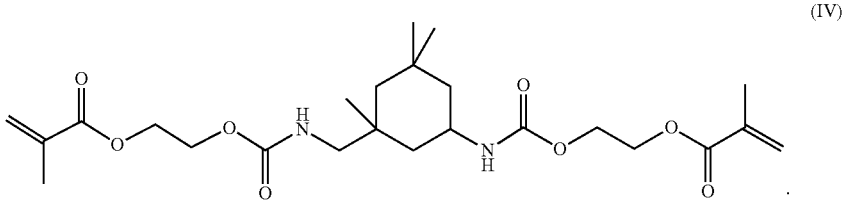 [SMILES: C=C(C)C(=O)OCCOC(=O)NCC1(C)CC(NC(=O)OCCOC(=O)C(=C)C)CC(C)(C)C1]

(IV)

Embodiment 26 is the orthodontic article of any of embodiments 1 to 25, wherein an average of the at least one urethane (meth)acrylate has a weight average molecular weight (Mw) of 1,000 g/mol to 35,000 g/mol.

Embodiment 27 is the orthodontic article of any of embodiments 1 to 26, wherein the polymerizable composition further includes a difunctional monomer in an amount of up to 15 wt. %, based on the total weight of the polymerizable composition.

Embodiment 28 is the orthodontic article of any of embodiments 1 to 27, wherein the polymerizable composition is polymerized and the polymerized composition has a first phase having a peak loss modulus temperature of less than 0, −5, or −10° C. and a second phase having a peak tan delta temperature greater than 30, 40, 50, 60, 70, or 80° C. as determined according to dynamic mechanical analysis after conditioning in deionized water at 37° C. for 24 hours.

Embodiment 29 is the orthodontic article of any of embodiments 1 to 28, wherein the polymerizable composition is polymerized and the polymerized composition exhibits an elongation at break of 15% or greater and a tensile strength at yield of at least 10 MPa as determined according to ASTM D638-14 after conditioning in phosphate-buffered saline having a pH of 7.4, for 24 hours at a temperature of 37° C.

Embodiment 30 is the orthodontic article of embodiments 1 to 29, wherein the polymerizable composition is polymerized and the polymerized composition exhibits a 3-point bend modulus of at least 100 MPa as determined according to dynamic mechanical analysis at 2% strain after conditioning in deionized water at 20-25° C. for 48 hours.

Embodiment 31 is the orthodontic article of any of embodiments 1 to 30, wherein the polymerizable composition further includes a photoinitiator.

Embodiment 32 is the orthodontic article of any of embodiments 1 to 31, wherein the polymerizable composition includes at least one hydrophilic monomer or polymer having a log P of less than 3, present in an amount of 1% to 29% by weight, based on the total weight of the polymerizable composition.

Embodiment 33 is the orthodontic article of embodiment 32, wherein the polymerizable composition includes at least one monofunctional (meth)acrylate monomer whose homopolymer has a $T_g$ of 150° C. or greater in an amount of 20% by weight or greater, based on the total weight of the polymerizable composition.

Embodiment 34 is a polymerizable composition. The polymerizable composition includes 30-65 parts by weight of monofunctional (meth)acrylate monomer(s) and at least one urethane (meth)acrylate including polymerized units of an aliphatic polycarbonate diol. A cured homopolymer of at least one monofunctional (meth)acrylate monomer has a $T_g$ of 30 degrees Celsius (° C.) or greater.

Embodiment 35 is the polymerizable composition of embodiment 34, wherein the at least one urethane (meth)acrylate and the monofunctional (meth)acrylate monomer(s) are present at a weight ratio ranging from 2:1 to 1:2.

Embodiment 36 is the polymerizable composition of embodiment 34 or embodiment 35, wherein the monofunctional (meth)acrylate monomer(s) having a $T_g$ of at least 30° C. has a log P value of greater than 1, 1.5, 2, 2.5, or 3.

Embodiment 37 is the polymerizable composition of any of embodiments 34 to 36, wherein the monofunctional (meth)acrylate monomer(s) having a $T_g$ of at least 30° C. are present in an amount of at least 15, 20, 25, 30, 35, 40, 45, or 50 wt. %, based on the total weight of the organic components of the composition.

Embodiment 38 is the polymerizable composition of any of embodiments 34 to 37, wherein the at least one monofunctional (meth)acrylate monomer(s) have a $T_g$ of at least 40, 50, 60, 70, 80, or 90° C.

Embodiment 39 is the polymerizable composition of any of embodiments 34 to 38, wherein at least one monofunctional (meth)acrylate monomer having a $T_g$ of at least 30° C. includes a cycloaliphatic group.

Embodiment 40 is the polymerizable composition of any of embodiments 34 to 39, wherein the at least one urethane (meth)acrylate includes a reaction product of an aliphatic polycarbonate diol, a diisocyanate, and a hydroxy functional (meth)acrylate.

Embodiment 41 is the polymerizable composition of embodiment 40, wherein the hydroxy functional (meth)acrylate is of Formula (II):

(II), wherein Q is a polyvalent organic linking group and A is a (meth)acryl functional group of the formula —XC(=O)C(R)=CH$_2$, wherein X is O, S, or NR$_4$, R$_4$ is H or alkyl of 1 to 4 carbon atoms, R$_1$ is a lower alkyl of 1 to 4 carbon atoms or H, and p is 1 or 2.

Embodiment 42 is the polymerizable composition of embodiment 40 or embodiment 41, wherein the at least one urethane (meth)acrylate is of Formula (VI):

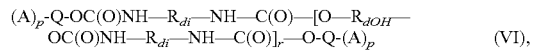

(VI), wherein A has the formula —XC(=O)C(R$_1$)=CH$_2$, wherein X is O, S, or NR$_4$, R$_4$ is H or alkyl of 1 to 4 carbon atoms, and R$_1$ is a lower alkyl of 1 to 4 carbon atoms or H, p is 1 or 2, Q is a polyvalent organic linking group, R$_{di}$ is the residue of a diisocyanate, R$_{dOH}$ is the residue of a polycarbonate polyol, and r averages from 1 to 15.

Embodiment 43 is the polymerizable composition of any of claims 34 to 42, wherein the at least one urethane (meth)acrylate includes a reaction product of an aliphatic polycarbonate diol, a diisocyanate, a diol (meth)acrylate, and a hydroxy functional (meth)acrylate.

Embodiment 44 is the polymerizable composition of embodiment 43, wherein the at least one urethane (meth)acrylate is of Formula (V):

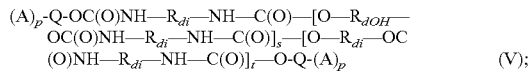

(V);

wherein A has the formula $-XC(=O)C(R_1)=CH_2$, wherein X is O, S, or $NR_4$, $R_4$ is H or alkyl of 1 to 4 carbon atoms, and $R_1$ is a lower alkyl of 1 to 4 carbon atoms or H, p is 1 or 2, Q is a polyvalent organic linking group, $R_{di}$ is the residue of a diisocyanate, $R_{dOH}$ is the residue of a polycarbonate polyol, s and t are independently 1 or greater, and s+t averages from 2 to 15, wherein the s and t units may be connected to each other in any order, and wherein $R_{AD}$ is the residue of a (meth)acrylated diol.

Embodiment 45 is the polymerizable composition of any of embodiments 34 to 44, wherein the at least one urethane (meth)acrylate includes a reaction product of an aliphatic polycarbonate diol and an isocyanate functional (meth)acrylate.

Embodiment 46 is the polymerizable composition of embodiment 45, wherein the at least one urethane (meth)acrylate is of Formula (VIII):

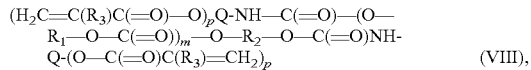

(VIII), wherein Q is a polyvalent organic linking group, $R_3$ is a lower alkyl of 1 to 4 carbon atoms or H, p is 1 or 2, each $R_1$ and $R_2$ are independently an aliphatic, cycloaliphatic, or aliphatic/cycloaliphatic alkylene group and an average number of carbon atoms in a combination of all the $R_1$ and $R_2$ groups is 4 to 10, and m is 2 to 23.

Embodiment 47 is the polymerizable composition of any of embodiments 34 to 46, wherein the at least one urethane (meth)acrylate includes a reaction product of an aliphatic polycarbonate diol, a diisocyanate, and an isocyanate functional (meth)acrylate.

Embodiment 48 is the polymerizable composition of embodiment 47, wherein the at least one urethane (meth)acrylate is of Formula (XI):

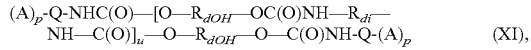

(XI), wherein u is 0 to 15, A has the formula $-XC(=O)C(R_1)=CH_2$, wherein X is O, S, or $NR_4$, $R_4$ is H or alkyl of 1 to 4 carbon atoms, and $R_1$ is a lower alkyl of 1 to 4 carbon atoms or H, p is 1 or 2, Q is a polyvalent organic linking group, $R_{di}$ is the residue of a diisocyanate, and $R_{dOH}$ is the residue of a polycarbonate polyol.

Embodiment 49 is the polymerizable composition of any of embodiments 34 to 48, wherein the at least one urethane (meth)acrylate includes a reaction product of an aliphatic polycarbonate diol, a diisocyanate, a diol (meth)acrylate, and an isocyanate functional (meth)acrylate.

Embodiment 50 is the polymerizable composition of embodiment 49, wherein the at least one urethane (meth)acrylate is of Formula (XII):

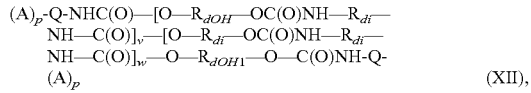

(XII)

wherein, $R_{di}$, $R_{AD}$, Q, A, and p, are defined as above, v+w is 1 to 15, and $R_{dOH1}$ is selected from $R_{dOH}$ or $R_{AD}$, with the provisos that if v is 0 then $R_{dOH1}$ is $R_{dOH}$, and if w is 0 then $R_{dOH1}$ is $R_{AD}$.

Embodiment 51 is the polymerizable composition of any of embodiments 34 to 50, wherein the at least one urethane (meth)acrylate further includes polymerized units of a polyester diol, wherein the urethane (meth)acrylate contains the same or more polymerized units of the aliphatic polycarbonate diol than the polyester diol.

Embodiment 52 is the polymerizable composition of embodiment 51, wherein the at least one urethane (meth)acrylate is of Formula (XIII):

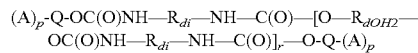

wherein each $R_{dOH2}$ is independently selected from the residue of a polyester polyol or the residue of a polycarbonate polyol, with the proviso that x is greater than 2.

Embodiment 53 is the polymerizable composition of any of embodiments 34 to 52, further including at least one urethane (meth)acrylate lacking aliphatic polycarbonate moieties.

Embodiment 54 is the polymerizable composition of any of embodiments 34 to 53, further including a urethane (meth)acrylate including polymerized units of a polyester diol, wherein the urethane (meth)acrylate including polymerized units of a polyester diol is present in an amount no more than the amount present of the at least one urethane (meth)acrylate including polymerized units of an aliphatic polycarbonate diol.

Embodiment 55 is the polymerizable composition of embodiment 54, wherein the at least one urethane (meth)acrylate including polymerized units of a polyester diol is of Formula (XIII) or Formula (XIV):

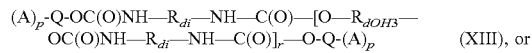
(XIII), or

(XIV), wherein A has the formula $-XC(=O)C(R_1)=CH_2$, wherein X is O, S, or $NR_4$, $R_4$ is H or alkyl of 1 to 4 carbon atoms, and $R_1$ is a lower alkyl of 1 to 4 carbon atoms or H, p is 1 or 2, Q is a polyvalent organic linking group, $R_{di}$ is a residue of a diisocyanate, $R_{dOH3}$ is a residue of a polyester polyol, and r averages from 1 to 15.

Embodiment 56 is the polymerizable composition of any of claims 34 to 55, wherein the aliphatic polycarbonate diol is of Formula (I):

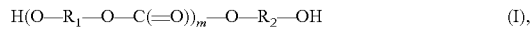
(I), wherein each of $R_1$ in each $(O-R_1-O-C(=O))$ repeat unit and each $R_2$ are independently an aliphatic, cycloaliphatic, or aliphatic/cycloaliphatic alkylene group and an average number of carbon atoms in a combination of all the $R_1$ and $R_2$ groups is 4 to 10, and m is 2 to 23.

Embodiment 57 is the polymerizable composition of any of embodiments 34 to 56, further including a compound of Formula (III):

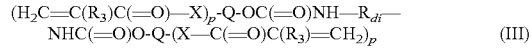
(III)

wherein Q is a polyvalent organic linking group, X is O, S, or $NR_4$, $R_4$ is H or alkyl of 1 to 4 carbon atoms, $R_3$ is a lower alkyl of 1 to 4 carbon atoms or H, p is 1 or 2, and $R_{di}$ is the residue of a diisocyanate.

Embodiment 58 is the polymerizable composition of embodiment 57, wherein the compound of Formula (III) is of Formula (IV):

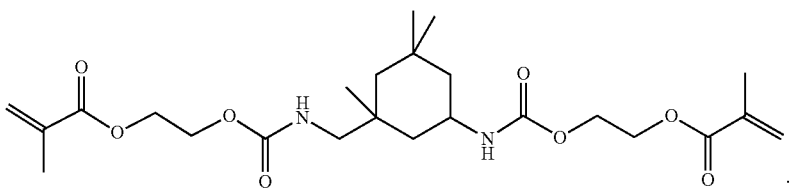

(IV)

Embodiment 59 is the polymerizable composition of any of embodiments 34 to 58, wherein an average of the at least one urethane (meth)acrylate has a weight average molecular weight (Mw) of 1,000 g/mol to 35,000 g/mol.

Embodiment 60 is the polymerizable composition of any of embodiments 34 to 59, further including a difunctional monomer in an amount of up to 15 wt. %, based on the total weight of the polymerizable composition.

Embodiment 61 is the polymerizable composition of any of embodiments 34 to 60, further including a photoinitiator.

Embodiment 62 is the polymerizable composition of any of embodiments 34 to 61, including at least one hydrophilic monomer or polymer having a log P of less than 3, present in an amount of 1% to 29% by weight, based on the total weight of the polymerizable composition.

Embodiment 63 is the polymerizable composition of embodiment 62, including at least one monofunctional (meth)acrylate monomer whose homopolymer has a $T_g$ of 150° C. or greater in an amount of 20% by weight or greater, based on the total weight of the polymerizable composition.

Embodiment 64 is a method of making an orthodontic article. The method includes a) obtaining a photopolymerizable composition; b) selectively curing the photopolymerizable composition; and c) repeating steps a) and b) to form multiple layers and create the orthodontic article. The photopolymerizable composition includes 30-65 parts by weight of monofunctional (meth)acrylate monomer(s) and at least one urethane (meth)acrylate including polymerized units of an aliphatic polycarbonate diol. A cured homopolymer of at least one monofunctional (meth)acrylate monomer has a $T_g$ of 30 degrees Celsius (° C.) or greater.

Embodiment 65 is the method of embodiment 64, wherein the photopolymerizable composition is cured using actinic radiation including UV radiation, e-beam radiation, visible radiation, or a combination thereof.

Embodiment 66 is the method of embodiment 65, wherein the actinic radiation is directed through a wall of a container holding the photopolymerizable composition.

Embodiment 67 is the method of embodiment 65 or embodiment 66, wherein 90% or greater of the actinic radiation is absorbed over a distance of 150 micrometers of the photopolymerizable composition.

Embodiment 68 is the method of any of embodiments 64 to 67, wherein the photopolymerizable composition is cured through a floor of a container holding the photopolymerizable composition.

Embodiment 69 is the method of any of embodiments 64 to 68, further including post curing the orthodontic article using actinic radiation.

Embodiment 70 is the method of any of embodiments 64 to 69, wherein the method includes vat polymerization of the photopolymerizable composition.

Embodiment 71 is the method of any of embodiments 64 to 70, further including subjecting the orthodontic article to a heat treatment.

Embodiment 72 is the method of any of embodiments 64 to 71, wherein the orthodontic article exhibits an initial relaxation modulus of 100 megapascals (MPa) or greater measured at 2% strain at 37° C.

Embodiment 73 is the method of any of embodiments 64 to 72, wherein the orthodontic article exhibits a percent loss of relaxation modulus of 70% or less or 40% or less.

Embodiment 74 is the method of any of embodiments 64 to 73, wherein the orthodontic article exhibits a relaxation modulus of 100 MPa or greater.

Embodiment 75 is the method of any of embodiments 64 to 74, wherein the orthodontic article exhibits an elongation at break of a printed article of 20% or greater or 70% or greater.

Embodiment 76 is the method of any of embodiments 64 to 75, wherein the orthodontic article exhibits a tensile strength at yield of 14 MPa or greater or 25 MPa or greater.

Embodiment 77 is the method of any of embodiments 64 to 76, wherein the orthodontic article contains 1 wt. % or less extractable components.

Embodiment 78 is the method of any of embodiments 64 to 77, wherein the orthodontic article exhibits a peak in loss modulus of 20° C. or less.

Embodiment 79 is the method of embodiment 78, exhibiting a tan delta peak of 80° C. or greater.

Embodiment 80 is the method of any of embodiments 64 to 79, wherein the orthodontic article includes a dental tray, a retainer, or an aligner.

Embodiment 81 is the method of any of embodiments 64 to 80, wherein the orthodontic article includes an aligner.

Embodiment 82 is the method of any of embodiments 64 to 81, wherein the photopolymerizable composition further comprising an antimicrobial lipid.

Embodiment 83 is the method of embodiment 82, wherein the antimicrobial lipid is present in the photopolymerizable composition in an amount of 0.1 wt. % or greater, 0.5 wt. %, 1 wt. %, 1.5 wt. %, 2 wt. %, 3 wt. %, or 4 wt. % or greater, based on the total weight of the photopolymerizable composition, and 20 wt. % or less, 15 wt. %, 12 wt. %, 10 wt. %, 8 wt. %, or 5 wt. % or less, based on the total weight of the photopolymerizable composition.

Embodiment 84 is the method of embodiment 82 or embodiment 83, wherein the antimicrobial lipid comprises monolaurin.

Embodiment 85 is the method of any of embodiments 82 to 84, wherein the photopolymerizable composition further comprises at least one enhancer comprising a carboxylic acid, a phenolic compound, a monohydroxy alcohol, a chelating agent, a surfactant, or a glycol ether.

Embodiment 86 is a non-transitory machine readable medium comprising data representing a three-dimensional model of an orthodontic article, when accessed by one or more processors interfacing with a 3D printer, causes the 3D printer to create an orthodontic article including a reaction product of a photopolymerizable composition. The photopolymerizable composition includes 30-65 parts by weight of monofunctional (meth)acrylate monomer(s) and at least one urethane (meth)acrylate including polymerized units of an aliphatic polycarbonate diol. A cured homopolymer of at least one monofunctional (meth)acrylate monomer has a $T_g$ of 30 degrees Celsius (° C.) or greater. The polymerized reaction product of the photopolymerizable composition has a shape of the orthodontic article.

Embodiment 87 is a method including a) retrieving, from a non-transitory machine readable medium, data representing a 3D model of an article; b) executing, by one or more processors, a 3D printing application interfacing with a manufacturing device using the data; and c) generating, by the manufacturing device, a physical object of the orthodontic article. The orthodontic article includes a reaction product of a photopolymerizable composition. The photopolymerizable composition includes 30-65 parts by weight of monofunctional (meth)acrylate monomer(s) and at least one urethane (meth)acrylate including polymerized units of an aliphatic polycarbonate diol. A cured homopolymer of at least one monofunctional (meth)acrylate monomer has a $T_g$ of 30 degrees Celsius (° C.) or greater. The polymerized reaction product of the photopolymerizable composition has a shape of the orthodontic article.

Embodiment 88 is a method including a) receiving, by a manufacturing device having one or more processors, a digital object comprising data specifying a plurality of layers of an orthodontic article; and b) generating, with the manufacturing device by an additive manufacturing process, the orthodontic article based on the digital object. The orthodontic article includes a reaction product of a photopolymerizable composition. The photopolymerizable composition includes 30-65 parts by weight of monofunctional (meth)acrylate monomer(s) and at least one urethane (meth) acrylate including polymerized units of an aliphatic polycarbonate diol. A cured homopolymer of at least one monofunctional (meth)acrylate monomer has a $T_g$ of 30 degrees Celsius (° C.) or greater. The polymerized reaction product of the photopolymerizable composition has a shape of the orthodontic article.

Embodiment 89 is a system including a) a display that displays a 3D model of an orthodontic article; and b) one or more processors that, in response to the 3D model selected by a user, cause a 3D printer to create a physical object of an orthodontic article. The orthodontic article includes a reaction product of a photopolymerizable composition. The photopolymerizable composition includes 30-65 parts by weight of monofunctional (meth)acrylate monomer(s) and at least one urethane (meth)acrylate including polymerized units of an aliphatic polycarbonate diol. A cured homopolymer of at least one monofunctional (meth)acrylate monomer has a $T_g$ of 30 degrees Celsius (° C.) or greater. The polymerized reaction product of the photopolymerizable composition has a shape of the orthodontic article.

Embodiment 90 is the orthodontic article of any of embodiments 1 to 33, wherein the orthodontic article is an orthodontic alignment tray.

Embodiment 91 is the orthodontic article of any of embodiments 1 to 33 or 90, wherein the polymerizable composition further comprises an antimicrobial lipid.

Embodiment 92 is the orthodontic article of embodiment 91, wherein the antimicrobial lipid is present in the polymerizable composition in an amount of 0.1 wt. % or greater, 0.5 wt. %, 1 wt. %, 1.5 wt. %, 2 wt. %, 3 wt. %, or 4 wt. % or greater, based on the total weight of the polymerizable composition, and 20 wt. % or less, 15 wt. %, 12 wt. %, 10 wt. %, 8 wt. %, or 5 wt. % or less, based on the total weight of the polymerizable composition.

Embodiment 93 is the orthodontic article of embodiment 91 or embodiment 92, wherein the antimicrobial lipid comprises monolaurin.

Embodiment 94 is the orthodontic article of any of embodiments 91 to 93, wherein the polymerizable composition further comprises at least one enhancer comprising a carboxylic acid, a phenolic compound, a monohydroxy alcohol, a chelating agent, a surfactant, or a glycol ether.

Embodiment 95 is the orthodontic article of any of embodiments 1 to 33 or 90 to 94, wherein the polymerizable composition comprises up to 30 wt. % polyether diol, based on the total weight of the polymerizable composition.

Examples

Objects and advantages of this disclosure are further illustrated by the following examples, but the particular materials and amounts thereof recited in these examples, as well as other conditions and details, should not be construed to unduly limit this disclosure.

Materials

Unless otherwise noted, all parts, percentages, ratios, etc. in the examples and the rest of the specification are by weight. The Materials Table (below) lists materials used in the examples and their sources.

| Materials Table | |
|---|---|
| Material designation | Description |
| 1-Adamantanol | Obtained from TCI America, Portland, OR. |
| 212-20 | A polycarbonate diol of about 1500 MW made with $CO_2$ and propylene oxide obtained as "CONVERGE POLYOL 212-20" from Aramco, Dhahran, Saudi Arabia. |
| 4-chloro-1,8-naphthalic anhydride | Obtained from Alfa Aesar, Haverhill, MA. |
| 4-hydroxy-TEMPO | 4-hydroxy-2,2,6,6-tetramethylpiperidine 1-oxyl, obtained from Sigma Aldrich, St. Louis, MO. |
| 4-tert-butylcyclohexanol | 4-tert-butylcyclohexanol, mixture of isomers, obtained from TCI America, Portland, OR. |
| Acetonitrile | Omnisolv HPLC grade obtained from EMD Millipore, a part of Merck KGaA, Darmstadt, Germany. |

Materials Table

| Material designation | Description |
|---|---|
| Acrylic acid | Obtained from Alfa Aesar, Haverill, MA. |
| Acryloyl chloride | Obtained from Sigma-Aldrich Chemical Company, St. Louis, MO. |
| Ammonium formate | Obtained as a 5M aqueous solution from Agilent Technologies, Waldbronn, Germany. |
| Anhydrous magnesium sulfate | Obtained from EMD Millipore, a part of Merck KGaA. |
| BHI Broth | Bacto Brain Heart Infusion (BHI) Broth obtained from Becton, Dickinson and Company (Franklin Lakes, NJ). |
| BEI | 1,1-bis(acryloyloxymethyl) ethyl isocyanate obtained as "KARENZ BEI" from Showa Denko, Tokyo, Japan. |
| BHT | 2,6-di-t-butyl-4-methylphenol obtained from Alfa Aesar, Haverhill, MA. |
| BiN | Bismuth neodecanoate obtained from Sigma-Aldrich, St. Louis, MO. |
| BnMA | Benzylmethacrylate, obtained from Sigma Aldrich. |
| C XP-2613 | A polycarbonate diol of about 2000 MW of what is believed to have about a 75:25 mole ratio of butane diol:hexane diol, obtained as "DESMOPHEN C XP-2613" from Covestro LLC., Leverkusen, Germany. |
| C-1090 | A polycarbonate diol of about 1000 MW made with about a 9:1 mole ratio of 3-methyl-1,5-pentanediol (MPD):1,6-hexane diol (HD), (i.e., 90% MPD,) obtained as "KURARAY POLYOL C-1090" from Kuraray Co. Ltd., Tokyo, Japan. |
| C-2050 | A polycarbonate diol of about 2000 MW made with about a 50% (i.e., 5:5) mole ratio of (MPD):(HD), obtained as "KURARAY POLYOL C-2050" from Kuraray Co. Ltd. |
| C-2090 | A polycarbonate diol of about 2000 MW made with about a 9:1 mole ratio of (MPD):(HD), obtained as "KURARAY POLYOL C-2090" from Kuraray Co. Ltd. |
| C-2100 | A polycarbonate diol of about 1000 MW that it is believed uses HD as the diol, obtained as "DESMOPHEN C-2100" from Covestro LLC. |
| C-2200 | A polycarbonate diol of about 2000 MW that it is believed uses HD as the diol, obtained as "DESMOPHEN C-2200" from Covestro LLC. |
| C-3090 | A polycarbonate diol of about 3000 MW made with about a 9:1 mole ratio of (MPD):(HD), obtained as "KURARAY POLYOL C-3090" from Kuraray Co. Ltd. |
| C-590 | A polycarbonate diol of about 500 MW made with about a 9:1 mole ratio of (MPD):(HD) obtained as "KURARAY POLYOL C-590" from Kuraray Co. Ltd. |
| CEA | 2-Carboxyethyl acrylate, obtained from Sigma-Aldrich, St. Louis, MO. |
| Chloroform | Obtained from EMD Millipore, a part of Merck KGaA, Darmstadt, Germany. |
| CHMA | Cyclohexyl methacrylate, obtained from Alfa Aesar, Haverhill, MA. |
| DBTDL | Dibutyltin diacrylate, obtained from Sigma-Aldrich, St. Louis, MO. |
| DDDMA | 1,12-dodecanediol dimethacrylate obtained as "SR262" from Sartomer, Exton, PA. |
| DCM | Obtained from EMD Millipore, a part of Merck KGaA. |
| DEA | Diethanolamine obtained from Alfa Aesar. |
| Desmodur I (IPDI) | Isophorone diisocyanate, under trade designation "DESMODUR I" equivalent weight 111.11, molecular weight 222.22 g/mole, from Covestro LLC. |

-continued

Materials Table

| Material designation | Description |
|---|---|
| Desmodur W (H12MDI) | Hydrogenated methylene diisocyanate, under trade designation "DESMODUR W", equivalent weight 131.25, molecular weight 262.5 g/mole, from Covestro LLC. |
| DiCPMA | Dicyclopentanyl methacrylate Obtained from TCI America, Portland, OR. |
| DMAP | 4-dimethylaminopyridine, obtained from Alfa Aesar, Haverhill, MA. |
| DMSO | Dimethyl sulfoxide, obtained from Alfa Aesar. |
| EGMM | Ethylene glycol monoacetoacetate monomethacrylate, obtained from TCI America. |
| EHMA | 2-Ethyl hexyl methacrylate, obtained from Alfa Aesar. |
| Ethanol | Obtained from Spectrum Chemicals, New Brunswick, NJ. |
| Ethanolamine | Obtained from Sigma Aldrich. |
| Ethyl acetate | Obtained from EMD Millipore, a part of Merck KGaA. |
| Exothane-10 | A urethane (meth)acrylate oligomer comprising a polyethylene oxide diol of about 400 MW, obtained as "EXOTHANE-10" from Esstech Inc., Essington, PA. |
| Exothane-108 | A urethane (meth)acrylate oligomer comprising a polytetramethylene oxide diol of about 650 MW, obtained as "EXOTHANE-108" from Esstech Inc. |
| G-AC-MAC | Glycerol acrylate methacrylate (1-(acryloyloxy)-3-(methacryloyloxy)-2-propanol, CAS 1709-71-3), obtained from TCI America, Portland, OR. |
| Glycerol-2-methacylate | 1,3-bis hydroxy-propyl-2methacrylate may be prepared according to the procedure of US 4,578,504, Example 5. |
| GMA | Glycidyl methacrylate obtained from Alfa Aesar. |
| HCl | Hydrochloric acid, obtained from Sigma Aldrich. |
| HDDMA | 1,6-Hexanediol dimethacrylate (SR239), obtained from Sartomer. |
| HDI | 1,6-diisocyanatohexane, equivalent weight 84.1, molecular weight 168.2, available under trade designation "DESMODUR H", from Covestro LLC. |
| HEA | Hydroxyethyl acrylate, obtained from Alfa Aesar. |
| HEMA | Hydroxyethyl methacrylate, obtained from TCI America, Portland, OR. |
| Heptane | Heptane (Ultra resi-analyzed) was obtained from Avantor, Center Valley, PA. |
| Hydroquinone | Obtained from Alfa Aesar. |
| IBOA | Isobornyl acrylate, obtained from Alfa Aesar. |
| IBOMA | Isobornyl methacrylate obtained as "SR423A" from Sartomer. |
| IBuMA | Isobutylmethacrylate, obtained from TCI America. |
| IEA | Isocyanatoethyl acrylate, MW 141.12, available under the trade designation "KARENZ AOI," from Showa Denko. |
| IEM | Isocyanatoethyl methacrylate, MW 155.15, available under the trade designation "KARENZ MOI," from Showa Denko. |
| IEM-EO | Isocyanatoethoxyethyl methacrylate, MW 199.2, available under the trade designation "KARENZ MOI-EG," from Showa Denko. |
| iPrOH | Isopropyl alcohol, obtained from EMD Millipore, apart of Merck KGaA. |

-continued

Materials Table

| Material designation | Description |
| --- | --- |
| IRG-TPO | 2,4,6-trimethylbenzoyldiphenylphosphine oxide photoinitiator obtained under the trade designation IRGACURE TPO, obtained from BASF. |
| KOH | Potassium hydroxide, obtained from Sigma Aldrich. |
| MDI | Product trade designation "MONDUR MLQ," an approximate 80:20 mixture of 4,4' and 2,4' diphenylmethane diisocyanate, equivalent weight 125.125, molecular weight 250.25, from Covestro LLC. |
| MeOH | Methanol, obtained from EMD Millipore, a part of Merck KGaA. |
| Methacrylic acid | Obtained from Sigma Aldrich. |
| Methacrylic anhydride | Obtained from Sigma Aldrich. |
| ML | Glyceryl monolaurate (monolaurin), obtained from Pfaltz and Bauer, Waterbury, CT. |
| $Na_2CO_3$ | Sodium Carbonate, obtained from Sigma Aldrich. |
| NL2030B | A polycarbonate diol of about 2000 MW made with about a 3:7 mole ratio of neopentyl glycol:butane diol, obtained as "NL2030B" from Mitsubishi Chemical Company, Tokyo, JP. |
| NL2005B | A polycarbonate diol of about 2000 MW made with about a 5:95 mole ratio of neopentyl glycol:butane diol, obtained as "NL2005B" from Mitsubishi Chemical Company. |
| NL2010DB | A polycarbonate diol of about 2000 MW made with about a 10:90 mole ratio of 1,10-decane diol:butane diol, obtained as "NL2010B" from Mitsubishi Chemical Company. |
| nPrMA | n-Propylmethacrylate, obtained from Sigma Aldrich. |
| NVP | 1-vinyl-2-pyrolidone, obtained from TCI Chemicals, Portland, OR. |
| OMNIRAD 379 | 2-Dimethylamino-2-(4-methyl-benzyl)-1-(4-morpholin-4-yl-phenyl)-butan-1-one, photoinitiator, obtained from IGM Resins, Charlotte, NC. |
| P-510 | A 3-methyl-1,5-pentanediol (MPD) adipate polyester diol of about 500 MW obtained as "KURARAY POLYOL P-510" from Kuraray Co. Ltd., Tokyo, Japan. |
| P-1010 | A 3-methyl-1,5-pentanediol (MPD) adipate polyester diol of about 1000 MW obtained as "KURARAY POLYOL P-1010" from Kuraray Co. Ltd. |
| P-1020 | A 3-methyl-1,5-pentane diol terephthalate diol of about 1000 MW obtained as "KURARAY POLYOL P-1020" from Kuraray. |
| P-6010 | A 3-methyl-1,5-pentanediol (MPD) adipate polyester diol of about 6000 MW obtained as "KURARAY POLYOL P-6010" from Kuraray Co. Ltd. |
| PBS | Phosphate buffered saline (PBS, 10X), pH = 7.4, obtained from Alfa Aesar. |
| PBS | Phosphate buffered saline (PBS, 1X), pH = 7.4, obtained from Fisher BioReagents, Pittsburgh, PA. |

Materials Table

| Material designation | Description |
|---|---|
| PEG600DMA | Polyethylene glycol 600 dimethacrylate, obtained from Sartomer. |
| PEMA | 2-Phenoxy ethyl methacrylate ("SR340"), obtained from Sartomer. |
| Petroleum ether | Obtained from EMD Millipore, a part of Merck KGaA. |
| Phenothiazine | Obtained from TCI America. |
| Propylene Carbonate | Obtained from Alfa Aesar. |
| PTMO-2000 | A poly(tetramethylene oxide) diol of about 2000 MW, obtained as "POLYTHF 2000" polyether from BASF, Florham Park, NJ. |
| p-toluenesulfonic acid | Obtained from TCI, America. |
| Sodium bicarbonate | Obtained from EMD Millipore, a part of Merck KGaA. |
| S. mutans | Streptococcus mutans, (ATCC ® 25175) obtained from American Type Culture Collection, Manassas, VA. |
| Sulfuric acid | Obtained from EMD Millipore, a part of Merck KGaA. |
| tBuA | Tertiary butyl acrylate, obtained from Sigma Aldrich. |
| Tetrahydrofuran | Omnisolv HPLC grade from EMD Millipore, a part of Merck KGaA. |
| THFMA | Tetrahydrofurfuryl methacrylate, obtained from Sartomer. |
| Tinuvin 326 | Phenol, 2-(5-chloro-2H-benzotriazol-2-yl)-6-(1,1-dimethylethyl)-4-methyl, UV-absorber, obtained from BASF. |
| TMXDI | 1,3-Bis(1-isocyanato-1-methylethyl) benzene, equivalent weight 122.15, molecular weight 244.3, from Sigma-Aldrich. |
| TPO | 2,4,6-trimethylbenzoyldiphenylphosphine oxide photoinitiator obtained as "IRGACURE TPO" from BASF. |
| Triethylamine | Obtained from EMD Millipore, a part of Merck KGaA. |
| TFAA | Trifluoroacetic anhydride, obtained from Alfa Aesar. |
| THFMA | Tetrahydrofurfurylmethacrylate under the trade designation SR203, obtained from Sartomer. |
| TMCHMA | 3,3,5-trimethylcylohexanemethacrylate, obtained from Sartomer. |
| Tween 20 | Polyethylene glycol sorbitan monolaurate, obtained from Alfa Aesar. |
| XK-672 | Zn based catalyst obtained as "K-KAT XK-672" from King Industries, Norwalk, CT. |

Preparatory Examples

Preparation of Naphthalimide Acrylate (NapA)

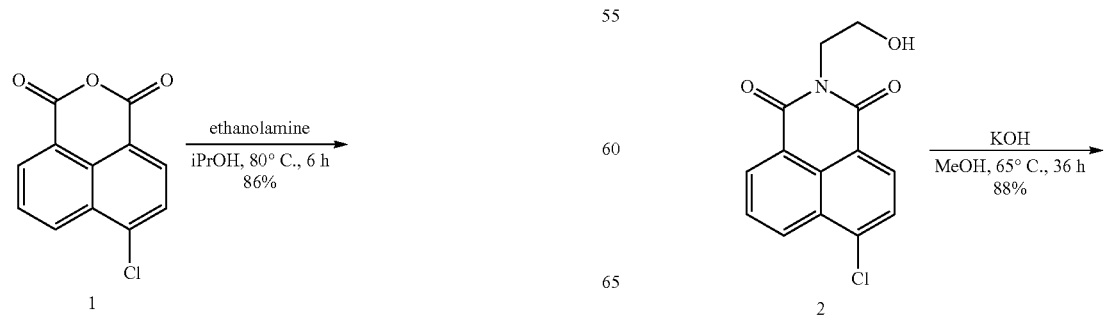

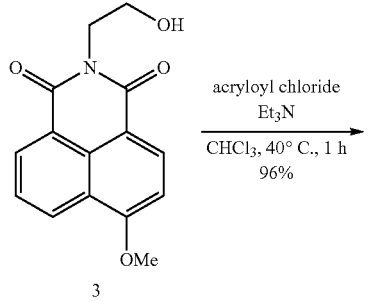

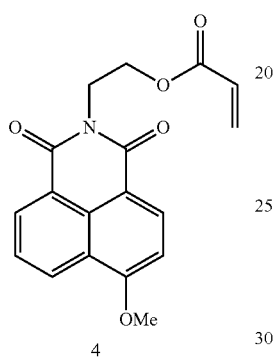

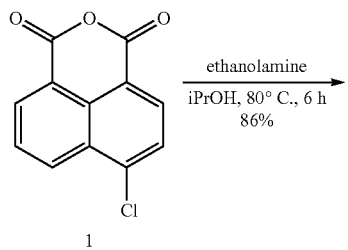

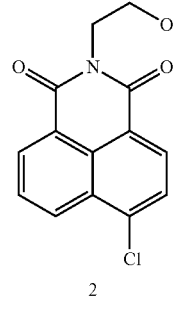

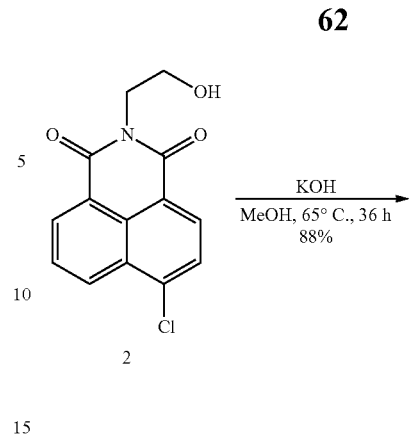

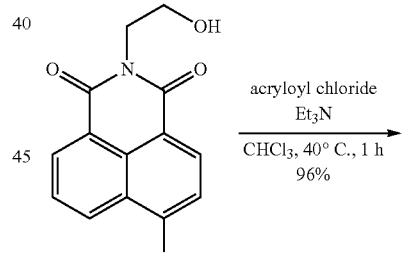

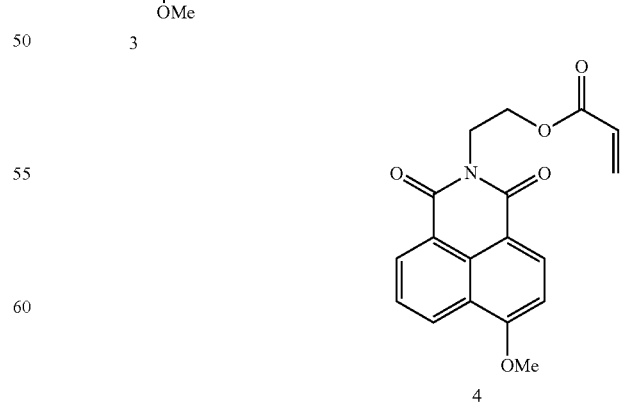

To a 1 L three-neck round-bottom flask was added 4-chloronaphthalic anhydride (100.0 g, 0.4299 moles, 1.0 equiv.), ethanolamine (26.26 g, 0.4299 moles, 1.0 equiv.), and iPrOH (516.7 g). The flask was outfitted with a temperature probe, overhead stirrer, and reflux condenser. The reaction mixture was heated to 80° C. with stirring for 6 hours, then cooled to 10° C. with an ice bath. The resulting yellow solid was collected via filtration and stirred with a mixture of water (300 g), iPrOH (300 g), and concentrated HCl (10 g). The resulting solid was filtered and washed with water/iPrOH (1:1, 500 g) and allowed to air dry. This afforded alcohol 2 (102 g, 86%).

To a 2 L three-neck round-bottom flask was added alcohol 2 (100.0 g, 0.3627 moles, 1.0 equiv.), KOH (40.71 g, 0.7255 moles, 2.0 equiv.), and methanol (581 g). The flask was outfitted with a temperature probe, overhead stirrer, and reflux condenser. The reaction mixture was heated to 65° C. with stirring for 36 hours, then cooled to 10° C. with an ice bath. The resulting yellow solid was collected via filtration and stirred with a mixture of water (300 g), MeOH (300 g), and concentrated HCl (10 g). The resulting solid was filtered and washed with water/MeOH (1:1, 600 g) and allowed to air dry. This afforded alcohol 3 (86.5 g, 88%).

To a 1 L 3-neck round-bottom flask was added alcohol 3 (80.00 g, 0.2949 moles, 1.0 equiv.), chloroform (704 g), and triethylamine (35.81 g, 0.3539 moles, 1.2 equiv.). The flask was outfitted with a Claisen adapter, overhead stirrer, and a pressure-equalizing addition funnel. The Claisen adapter was outfitted with a temperature probe and a reflux condenser. The reaction mixture was stirred and heated to 40° C. Acryloyl chloride (29.36 g, 0.3244 moles, 1.1 equiv.) was added dropwise via the addition funnel such that the reaction temperature did not rise above 45° C. After addition was complete, the reaction was stirred for 30 minutes. Triethylamine (6.00 g, 0.0593 moles, 0.2 equiv.) was added, followed by acryloyl chloride (5.00 g, 0.0552 moles, 0.19 equiv.) dropwise. The reaction was stirred for an additional 30 minutes at 40° C. Next, the reaction flask was outfitted with a distillation head, condenser, and receiving flask. The reaction mixture was heated to strip most of the chloroform. EtOH (500 g) was added, and the strip continued until the distillation head temperature reached 78° C. The reaction mixture was cooled to 10° C. with an ice bath and filtered. The resulting solid was washed with water/HCl (10:1, 500 mL), water/Na$_2$CO$_3$ (10:1, 500 mL), and water/EtOH (1:1, 500 mL). The solid was allowed to dry to afford the product 4 as a pale yellow solid (92.5 g, 96%).

Preparation of Adamantyl-1-Methacrylate (AdMA)

A 2 L, 3 neck round-bottom flask was fitted with a dean-stark trap with a condenser, magnetic stir bar, and a thermometer. 1-Adamantanol (252 g 1.650 mol), hydroquinone (0.3 g), methacrylic acid (455 g, 5.28 mmol), and methylcyclohexane (400 g) were added and the mixture was stirred. Sulfuric acid (10.5 g) was then added to the mixture, and then dry air was slowly bubbled into the mixture. The mixture was heated to reflux under constant bubbling of air for 26 hours, during which time the reaction product water was removed using the trap. The mixture was then cooled to room temperature, and slowly added to a mechanically stirred, ice-bath cooled mixture of 350 g KOH (6.2 mol) in 1000 g of deionized water and 500 g hexanes. After the addition was complete, the resulting mixture was separated using a separatory funnel, and extracted 1×500 mL hexanes. The combined organic extracts were washed with a saturated aqueous sodium bicarbonate solution, and then 20 mg of phenothiazine was added to the organic phase. This was then dried over anhydrous magnesium sulfate, filtered, and concentrated by rotary evaporation. The concentrate was then distilled under vacuum (BP=87-90° C., 0.3 torr), where the receiver flask contained 15 mg of 4-hydroxy-TEMPO, and 320 g of liquid was obtained. BHT (48 mg) was then added and dry air was bubbled into the clear product for 30 seconds before storage. $^1$H NMR: 5.99 (m, 1H), 5.45 (m, 1H), 2.14 (m, 9H), 1.87 (m, 3H), 1.64 (m, 6H). $^{13}$C NMR: 168.5, 138.1, 124.3, 80.4, 41.3, 36.3, 30.9, 18.4. Purity by GC=98.4%.

Characterization of the Above Material by Nuclear Magnetic Resonance (NMR) Spectroscopy An Ultrashield 500 Plus FT NMR instrument from Bruker (Billerica, MA) was used to acquire $^1$H NMR (500 MHz) and $^{13}$C NMR (125 MHz) spectra. Chemical shifts (δ) are reported in ppm relative to CDCl$_3$. Abbreviations for splitting patterns are as follows; s (singlet); d (doublet); t (triplet); q (quartet); m (multiplet); br (broad); app (apparent) and combinations of these abbreviations.

Preparation of 4-Tert-Butylcyclohexyl Methacrylate (Mixture Cis/Trans) (tBuCHMA)

A 2 L, 3 neck round-bottom flask was fitted with a 250 mL addition funnel, magnetic stir bar, and a thermometer. 4-tert-butylcyclohexanol (150 g, 960 mmol), dichloromethane (600 g), triethylamine (178 g, 1760 mmol), and DMAP (6.4 g, 52 mmol) were added to the flask, and then methacrylic anhydride (263 g, 1710 mmol) was added dropwise keeping the temperature below 35° C. This mixture was stirred at room temperature for 24 hours, and then 150 mL water was added and stirred overnight. Dichloromethane (500 g) was then added, and the organic phase was washed with 200 mL water, 200 mL of 0.1 M HCl, and 200 mL saturated sodium bicarbonate. The organic phase was dried over anhydrous magnesium sulfate and 20 mg phenothiazine was added. This was filtered and concentrated by rotary evaporation. The concentrate was then distilled under vacuum (BP=73-90° C., 0.3 torr), where the receiver flask contained 7 mg of 4-hydroxy-TEMPO, and 170 g of liquid was obtained. BHT (26 mg) was then added and dry air was bubbled into the clear product for 30 seconds before storage. $^1$H NMR was consistent with a mixture of 72% trans and 28% cis isomer as described in Macromolecules, 1993, 26, 1659-1665. GC analysis showed a total of 96% of the two isomers with a ratio of 73% trans/27% cis.

Characterization of the Above Material by Gas Chromatography (GC)

Sample purity and product ratios were determined by gas chromatography (GC) and was performed using a Hewlett Packard (Palo Alto, CA) 6890 Series Plus gas chromatograph with a flame ionization detector and HP G1530A digital integrator. Sample injection was done with a 7683 series injector in conjunction with an injection volume of 2 microliters, injection port at a temperature of 250° C., and a split ratio of 20:1. A 30 m×0.53 mm×5 micrometer column obtained under the trade designation "RESTEX RTX-1" from Restek Corp. (Bellefonte, PA) was utilized with a flow rate of 12.4 mL/min He as the carrier gas with a temperature program of 50° C. to 230° C. at 15° C./min; 230° C. to 280° C. at 50° C./min; then hold at 280° C. for 2 min.

Preparation of Diol Diacrylates

Preparation of C-590 Diol Diacrylate

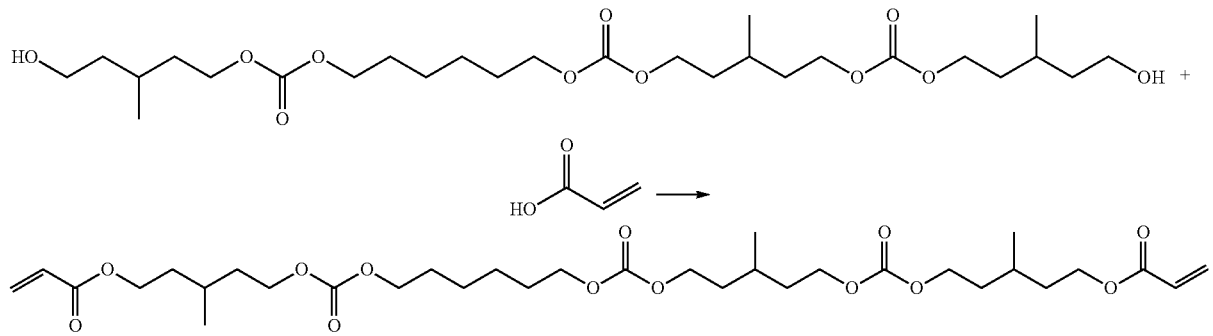

C-590 diol (50 g, 90.79 mmol;) and acrylic acid (19.8 g, 275 mmol,) and p-toluenesulfonic acid (1.96 g, 11.3 mmol,) were charged into a 250 mL 3-neck flask equipped with a magnetic stirring bar, a thermocouple and a condenser. The mixture was heated at 85° C. Vacuum (15-20 torr) was applied for 2 minutes every 15-20 minutes in order to remove any formed water from the reaction. This was repeated for 4 hours at which time there were no signs of H₂O forming or condensing on the flask walls. The heat was turned off After cooling to room temperature, the mixture was dissolved in a 130 mL ethyl acetate/petroleum ether mixture (10:3 ratio). The mixture was extracted with 10% aqueous NaOH (100 mL) then H₂O (200 mL). The organic layer was dried (over Na₂SO₄), then concentrated to give a clear liquid with 91% yield.

Preparation of C-590 Diol Dimethacrylate (C-590 Diol MA)

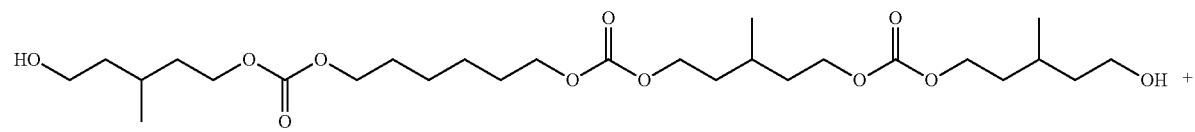

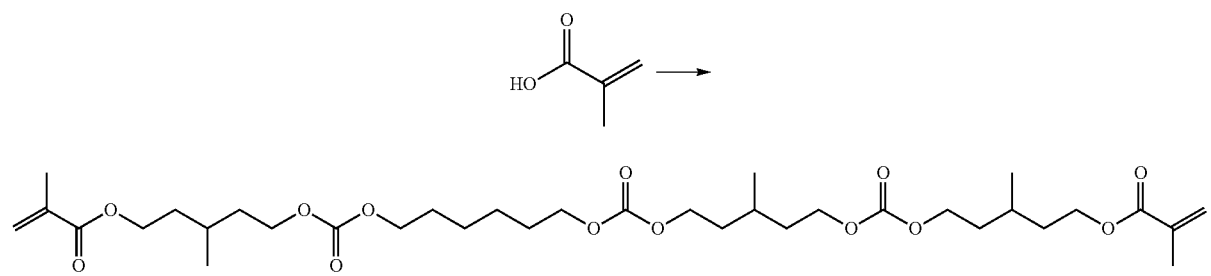

This material was prepared following the procedure described above for preparation of C-590 diol diacrylate, except that methacrylic acid was used instead of acrylic acid. The product was isolated as a low viscosity liquid in 88-93% yield.

Preparation of C-2050 Diol Dimethacrylate (C-2050 Diol MA)

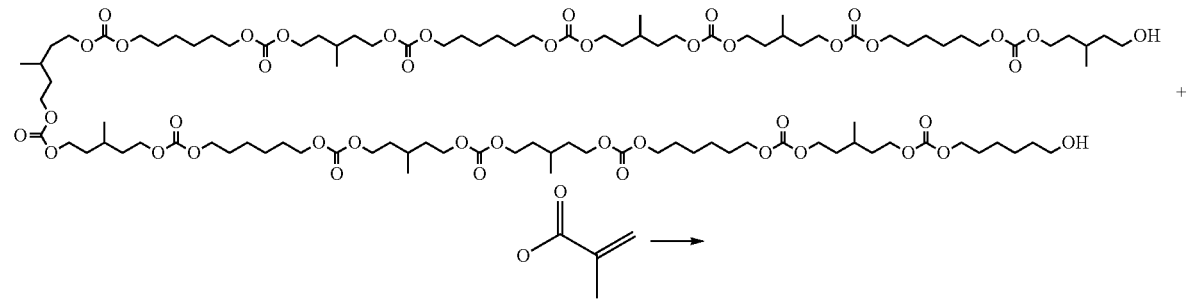

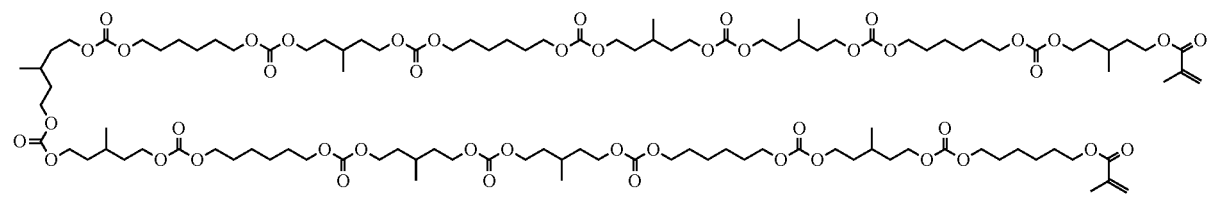

This material was prepared following the procedure described above for preparation of C-590 diol diacrylate, except that methacrylic acid was used instead of acrylic acid and C-2050 diol was used instead of C-590 diol.

Preparation of Acrylated Diol Adduct of Diethanolamine and Isocyanatoethyl Methacrylate

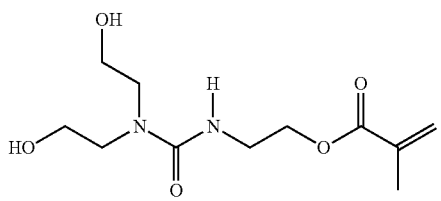 [SMILES: C=C(C)C(=O)OCCNC(=O)N(CCO)CCO]

To 105.14 g (1 eq) diethanolamine, 0.104 (400 ppm on total solids) BHT, and 0.026 g (100 ppm based on total solids) 4-hydroxy-TEMPO in a 500 mL flask with overhead stirrer in ice, was added 155.15 g (1 eq) IEM over 55 minutes. To keep the internal temperature of the reaction under 30° C., ice was at hand to cool the water bath. After addition, a sample was taken for FTIR, showing no —NCO peak at 2265 cm$^{-1}$. The reaction was bottled in a polyethylene container.

Preparation of Acrylated Diol Adduct of Diethanolamine and Isocyanatoethyl Acrylate

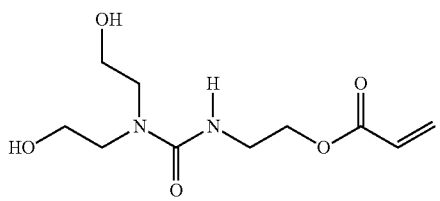 [SMILES: C=CC(=O)OCCNC(=O)N(CCO)CCO]

A dry-ice/water/isopropanol bath was prepared by mixing these three components to control the bath temperature from −70° C. to −10° C. A flask was charged with 50 g of ethyl acetate, and fitted with two pressure equalizing funnels, one containing 42.69 g (0.406 eq) diethanolamine, and the other containing 57.31 g (0.406 eq) IEA. The flask was placed in a −70° C. dry-ice/water/isopropanol bath under dry air, and addition of the DEA and IEA at equimolar rates was started. The DEA was solidifying on the side of the flask at −70° C., so the temperature of the bath was adjusted to −10° C. by addition of water. The addition of the IEA was complete at 54 minutes and the DEA addition was complete at 59 minutes. Both funnels were rinsed with 5 g ethyl acetate each. Solid DEA was present in the reaction, and at 1 hour and 10 minutes, the bath was removed. At about 2 hours the solids were gone. The reaction was concentrated with overhead stirring with the flask in oil bath at about 70° C. at about 1.5 torr for about 1 hour. The material was bottled in a polyethylene container.

Preparation of Diethanolamine-IEM-EO adduct:

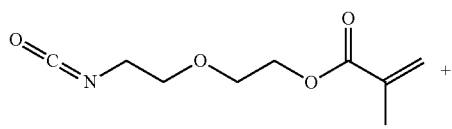

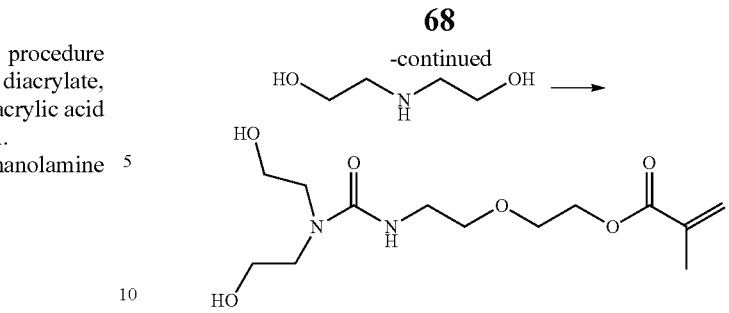

Diethanolamine (81.20 g, 772 mmol) was placed in a 500 mL glass jar equipped with a mechanical stirrer and a thermocouple. BHT (0.1 g) was added. The jar was placed in an ice bath with continuous stirring. When the temperature of diethanolamine reached 15-18° C., IEM-EO (154 g, 773.09 mmol) was added in small increments over 1 hour so that the reaction bulk temperature remained at or below 30° C. After complete addition, the product was obtained as a colorless viscous liquid.

Ethylene Glycol Mono-Acetoacetate Mono-Methacrylate Reaction with 2-Hydroxyethyl Acrylate:

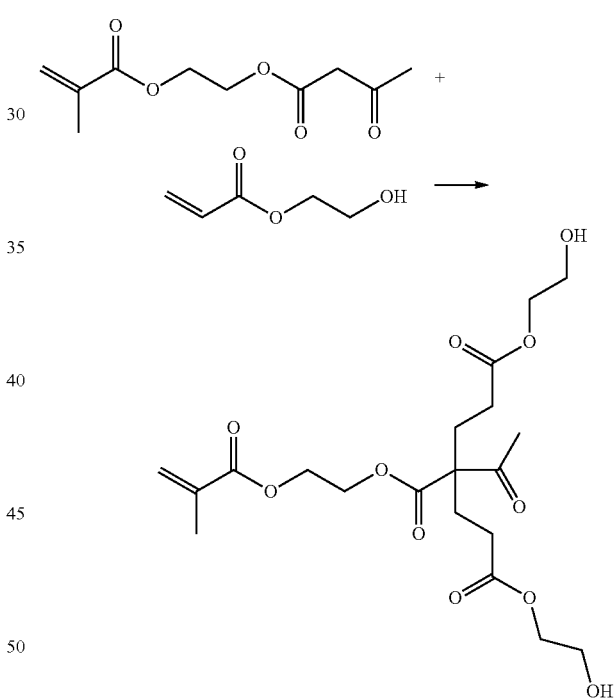

Ethylene glycol monoacetoacetate monomethacrylate (EGMM, 16.6 g, 77.5 mmol) and 2-hydroxyethyl acrylate (HEA, 18 g, 155.01 mmol) were charged into a 100 mL 3-neck round bottom flask equipped with a mechanical stirrer, a thermocouple, and dry air flowing through the reactor then into an oil bubbler. BHT (15 mg) and DBU (0.30 g) were added and the mixture was mixed at room temperature. A mild and slow exotherm was observed where the reaction bulk temperature rose from 25 to 55° C. over 3 hours. After the temperature stabilized, the mixture was then heated at 60° C. for 3 hours. The heat was turned off and the product (ACAC-MA) was collected as a viscous amber colored oil with a quantitative yield.

Preparation of Polycarbonate Diol Based Urethane (Meth) Acrylates

The urethane acrylates are of six main types:

1) Polycarbonate diols reacted with diisocyanates capped with (meth)acrylate mono-ols such as HEA and HEMA. Below is an idealized structure of such a material, illustrated with a hexane diol based polycarbonate diol:

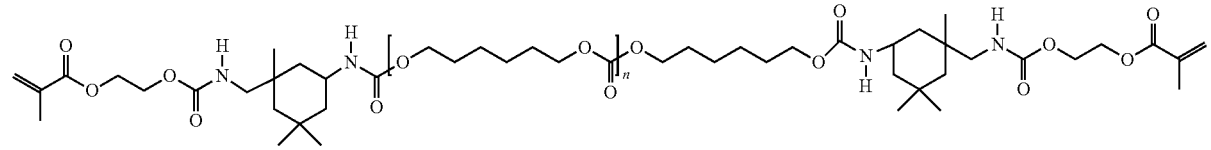

2) Polycarbonate diols capped with isocyanate-(meth)acrylates, illustrated with a hexane diol based polycarbonate diol and IEM:

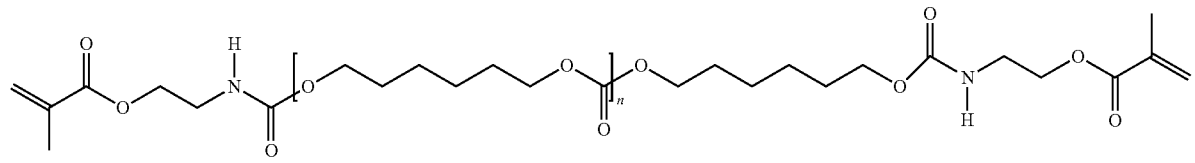

n~6.5 per 1000 MW

3) Diisocyanates capped with (meth)acrylate mono-ols:

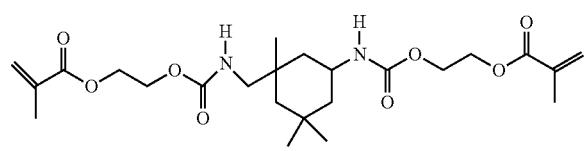 [SMILES: C=C(C)C(=O)OCCOC(=O)NCC1(C)CC(NC(=O)OCCOC(=O)C(=C)C)CC(C)(C)C1]

4) Diisocyanates capped with polyols, then reacted with isocyanato (meth)acrylates:

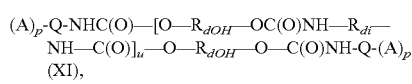

(XI), wherein u is 0 to 15, A has the formula —XC(=O)C($R_1$)=$CH_2$, wherein X is O, S, or $NR_4$, $R_4$ is H or alkyl of 1 to 4 carbon atoms, and $R_1$ is a lower alkyl of 1 to 4 carbon atoms or H, p is 1 or 2, Q is a polyvalent organic linking group, $R_{di}$ is the residue of a diisocyanate, and $R_{dOH}$ is the residue of a polycarbonate polyol.

5) Polycarbonate diols reacted with diisocyanates, diol (meth)acrylate, and hydroxy functional (meth)acrylates:

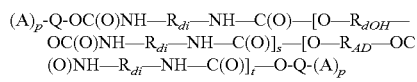

wherein A has the formula —XC(=O)C($R_1$)=$CH_2$, wherein X is O, S, or $NR_4$, $R_4$ is H or alkyl of 1 to 4 carbon atoms, and $R_1$ is a lower alkyl of 1 to 4 carbon atoms or H.s, p is 1 or 2, Q is a polyvalent organic linking group, $R_{di}$ is the residue of a diisocyanate, $R_{dOH}$ is the residue of a polycarbonate polyol, s and t are independently 1 or greater, and s+t averages from 2 to 15, wherein the s and t units may be connected to each other in any order, wherein $R_{AD}$ is the residue of a (meth)acrylated diol.

6) Polycarbonate diols reacted with diisocyanates, diol (meth)acrylate, and isocyanato functional (meth)acrylates:

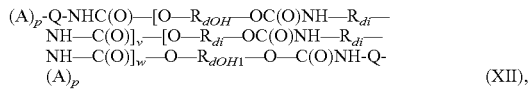

(XII), wherein, $R_{di}$ is the residue of a diisocyanate, $R_{AD}$ is the residue of a (meth)acrylated diol, Q is a polyvalent organic linking group, A has the formula —XC(=O)C($R_1$)=$CH_2$, wherein X is O, S, or $NR_4$, $R_4$ is H or alkyl of 1 to 4 carbon atoms, and $R_1$ is a lower alkyl of 1 to 4 carbon atoms or H, p is 1 or 2, v+w is 1 to 15, and $R_{dOH1}$ is selected from $R_{dOH}$ or $R_A$, with the provisos that if v is 0 then $R_{dOH1}$ is $R_{dOH}$, and if w is 0 then $R_{dOH1}$ is $R_{AD}$.

Type 1: 4 IPDI/2 C-2050/2 HEMA (PE-1)

A 1 L three-necked round-bottom flask was charged with 514.75 g C-2050 (0.52285 eq, 984.5 hydroxide equivalent weight (OH EW)), heated to about 45° C., then were added 116.19 g IPDI (1.0457 eq), 0.280 g BHT (400 ppm), and 0.175 DBTDL (250 ppm). The reaction was heated under dry air to an internal setpoint of 105° C. (temperature reached at about 20 minutes). At 1 hour and 20 minutes 69.06 g HEMA (0.5307 eq, 130.14 MW, a 1.5% excess) was added via an addition funnel at a steady rate over 1 hour and 10 minutes. The reaction was heated for about 2.5 hours at 105° C., then an aliquot was checked by Fourier transform infrared spectroscopy (FTIR) and found to have no —NCO peak at 2265 $cm^{-1}$ and the product was isolated as a clear, viscous material.

Type 2: C-2050/2 IEM (PE-2)

A 1 L three-necked round-bottom flask was charged with 431.93 g C-2050 (0.43873 eq, 984.5 OH EW), 0.200 g BHT (400 ppm), and 0.125 g DBTDL (250 ppm) and heated to an internal temperature of about 60° C. under dry air. Then 68.07 g IEM (0.43873 eq, 155.15 MW) was added via an addition funnel over about 1 hour and 20 minutes. At 1 hour and 30 minutes an aliquot was checked by FTIR and found to have no —NCO peak at 2265 cm$^{-1}$. At 1 hour and 38 minutes 1.32 g more IEM was added, and an aliquot was checked by FTIR and found to have no —NCO peak at 2265 cm$^{-1}$. At 4 hours into the reaction, the reaction was stopped and the product was isolated as a clear, viscous material.

Type 3: IPDI/HEMA (PE-3)

A 1 L three-necked round-bottom flask was charged with 319.80 g IPDI (2.878 eq), 0.280 g BHT, and 0.175 g bismuth neodecanoate (250 ppm based on solids) and heated to an internal temperature of about 55° C. under dry air. Then 380.20 g (2.921 eq) HEMA was added over 1 hour and 45 minutes, with the internal temperature rising to a maximum of 90° C. At 2 hours and 25 minutes an aliquot was checked by FTIR and found to have no —NCO peak at 2265 cm$^{-1}$.

Type 4: 2 IPDI/4 C-1090/2 IEM (PE-51)

A 1 L flask was charged with 44.40 g IPDI (0.39996 eq), 390.51 C-190 ((0.799132 eq) and 0.125 g XK-672 (250 ppm based on total solids), and heated to 100° C. After about 45 minutes, 65.09 g IEM (0.4195 eq) was added over about 20 minutes. At 4.75 hours an aliquot was checked by FTIR and found to have a very small —NCO peak at 2265 cm$^{-1}$. About 250 g was retained at 100% solids. A portion, 255.03 g, was diluted with 109.3 g IBOMA.

Type 5: 4 IPDI/2 C-2050/1 IEM-DEA/1 HEMA (PE-56)

A 250 mL three-necked round-bottom flask with overhead stirrer, under dry air, was charged with 16.58 g IPDI (0.1492 eq), 4.85 g IEM-DEA (0.0373 eq), 0.040 g BHT (400 ppm with respect to total solids), and 0.025 g XK-672 (250 ppm), and heated to 80° C. for 15 minutes. At 25 minutes the setpoint for the reaction was adjusted to 100° C. At 1 hour and 25 minutes, 73.42 g C-2050 (0.0746 eq, OH EW 984.2) was charged to the reaction. At 3 hours and 45 minutes, an aliquot was checked by Fourier transform infrared spectroscopy (FTIR) and found to have a small —NCO peak at 2265 cm$^{-1}$. At 4 hours, 0.5 g more HEMA was added to the reaction. At 7 hours and 20 minutes, FTIR analysis showed no —NCO peak. The 99.03 g of solids of product was diluted with 66.02 g IBOMA to provide a clear, viscous liquid.

Type 6: 2 IPDI/3 C-2050/1 IEM-DEA/1 IEM (PE-57)

A 250 mL three-necked round-bottom flask with overhead stirrer, under dry air, was charged with 6.13 g IPDI (0.05513 eq), 3.59 g IEM-DEA (0.02757 eq), 81.39 g C-2050 (0.08270 eq, OH EW 984.2) 0.040 g BHT (400 ppm with respect to total solids), and 0.025 g XK-672 (250 ppm), and heated to 85° C. for 23 minutes. At 23 minutes, the setpoint for the reaction was adjusted to 100° C. At 2 hours and 10 minutes, 8.90 g IEM (0.05734 eq) was added. At 4 hours, an aliquot was checked by Fourier transform infrared spectroscopy (FTIR) and found to have a very small —NCO peak at 2265 cm$^{-1}$. The product was then diluted with 66.6 g IBOMA to provide a clear, viscous liquid.

The samples in Tables 2, 3, and 4 below were prepared by methods according to those of Types 1-6 described above, using the amounts and types of materials indicated in the table.

TABLE 2

Preparative Examples of Polycarbonate Diol Based Polyurethane (Meth) Acrylates

| Sample | Designation | Isocyanate Type | g | Diol Type | g | OH EW | Hydroxy functional (meth)-acrylate Type | g | Catalyst Type | g | BHT g |
|---|---|---|---|---|---|---|---|---|---|---|---|
| PE-4 | 4 IPDI/2 P-1020/2 HEMA | IPDI | 39.02 | P-1020 | 87.79 | 500 | HEMA | 23.19 | DBTDL | 0.075 | 0 |
| PE-5 | 4 IPDI/2 C-2050/2 HEMA | IPDI | 82.99 | C-2050 | 367.68 | 984.2 | HEMA | 49.33 | DBTDL | 0.125 | 0.200 |
| PE-6 | 4 H12MDI/2 C-2050/2 HEMA | H12MDI | 95.17 | C-1090 | 356.94 | 984.2 | HEMA | 47.89 | DBTDL | 0.125 | 0.200 |
| PE-7 | 4 IPDI/2 C-2050/2 HEMA | IPDI | 82.99 | C-2050 | 367.68 | 984.2 | HEMA | 49.33 | DBTDL | 0.125 | 0.200 |
| PE-8 | 4 IPDI/2 C-2020/2 HEMA | IPDI | 83.81 | C-2020 | 366.37 | 971.42 | HEMA | 49.82 | DBTDL | 0.125 | 0.200 |
| PE-9 | C-2090/IEM | IEM | 69.63 | C-2090 | 430.37 | 959 | — | | DBTDL | 0.125 | 0.200 |
| PE-10 | C-2090/IEM-EO | IEM-EO | 86.00 | C-2050 | 414.00 | 959 | — | | DBTDL | 0.125 | 0.200 |
| PE-11 | C-2050/IEM | IEM | 18.91 | C-2050 | 120.00 | 984.2 | — | | DBTDL | 0.035 | 0.056 |
| PE-12 | C-2200/IEM | IEM | 68.86 | C-2200 | 431.14 | 971.42 | — | | DBTDL | 0.125 | 0.200 |
| PE-13 | 4 IPDI/2 C-3090/2 HEMA | IPDI | 60.57 | C-3090 | 403.43 | 1480.21 | HEMA | 36.00 | DBTDL | 0.125 | 0.200 |
| PE-14 | C-3090/IEM | IEM | 47.44 | C-3090 | 452.56 | 1480.21 | — | — | DBTDL | 0.125 | 0.200 |
| PE-15 | C-1090/IEM | IEM | 117.78 | C-1090 | 382.22 | 503.5 | — | — | DBTDL | 0.125 | 0.200 |
| PE-16 | C-590/IEM | IEM | 192.83 | C-590 | 307.17 | 247.14 | — | — | DBTDL | 0.125 | 0.200 |
| PE-17 | 4 IPDI/2 212-20/2 HEMA | IPDI | 98.96 | 212-20 | 342.22 | 768.49 | HEMA | 58.82 | DBTDL | 0.125 | 0.200 |
| PE-18 | 4 IPDI/2 PTMO-2000/2 HEMA | IPDI | 82.82 | PTMO-2000 | 367.95 | 997.0 | HEMA | 49.23 | DBTDL | 0.125 | 0.200 |
| PE-19 | 4 IPDI/1.5 C-2050/2.5 HEMA | IPDI | 98.70 | C-2050 | 327.96 | 984.2 | HEMA | 73.34 | DBTDL | 0.125 | 0.200 |
| PE-20 | 4 IPDI/2.5 C-2050/1.5 HEMA | IPDI | 71.6 | C-2050 | 396.49 | 984.2 | HEMA | 31.92 | DBTDL | 0.125 | 0.200 |
| PE-21 | 4 TMXDI/2 C-2050/2 HEMA | TMXDI | 89.78 | C-2050 | 361.68 | 984.2 | HEMA | 48.54 | DBTDL | 0.125 | 0.200 |
| PE-22 | 4 IPDI/2 C-2050/2 HEA | IPDI | 117.46 | C-2050 | 520.24 | 984.2 | HEA | 62.3 | DBTDL | 0.125 | 0.200 |
| PE-23 | 4 HDI/2 C-2050/2 HEMA | HDI | 65.47 | C-2050 | 383.11 | 984.2 | HEMA | 51.42 | DBTDL | 0.125 | 0.200 |

TABLE 2-continued

Preparative Examples of Polycarbonate Diol Based Polyurethane (Meth) Acrylates

| Sample | Designation | Isocyanate Type | g | Diol Type | g | OH EW | Hydroxy functional (meth)-acrylate Type | g | Catalyst Type | g | BHT g |
|---|---|---|---|---|---|---|---|---|---|---|---|
| PE-24 | 4 MDI/2 C-2050/2 HEMA | MDI | 91.56 | C-2050 | 360.11 | 984.2 | HEMA | 48.33 | DBTDL | 0.125 | 0.200 |
| PE-25 | 4 IPDI/2 C-1090/2 HEMA | IPDI | 131.81 | C-1090 | 289.85 | 488.67 | HEMA | 78.35 | DBTDL | 0.125 | 0.200 |
| PE-26 | 4 IPDI/2 C-2015N/2 HEMA | IPDI | 83.44 | C-2015N | 366.97 | 977.35 | HEMA | 49.60 | DBTDL | 0.125 | 0.200 |
| PE-27 | 4 IPDI/2 C-2050/2 HEMA | IPDI | 117.46 | C-2050 | 520.24 | 984.2 | HEMA | 69.82 | BiN | 0.177 | 0.283 |
| PE-28 | 4 IPDI/2 XP C2613/2 HEMA | IPDI | 82.91 | XP C2613 | 373.11 | 1000 | HEMA | 49.29 | DBTDL | 0.125 | 0.200 |
| PE-29 | 4 IPDI/2 C 7203/2 HEMA | IPDI | 81.08 | C 7203 | 370.73 | 1016.12 | HEMA | 48.19 | DBTDL | 0.125 | 0.200 |
| PE-30 | 4 IPDI/1.5 C-3090/2.5 HEMA | IPDI | 74.20 | C-3090 | 370.67 | 1480.21 | HEMA | 55.13 | DBTDL | 0.125 | 0.200 |
| PE-31 | 4 IPDI/1 C-3090/3 HEMA | IPDI | 95.75 | C-3090 | 318.88 | 1480.21 | HEMA | 85.37 | DBTDL | 0.125 | 0.200 |
| PE-32 | 4 IPDI/2 C-2050/2 HEMA | IPDI | 265.57 | C-2050 | 1176.6 | 984.2 | HEMA | 157.86 | BiN | 0.400 | 0.640 |
| PE-33 | IPDI/HEMA | IPDI | 319.8 | — | — | — | HEMA | 380.20 | BiN | 0.175 | 0.280 |
| PE-34 | 4 IPDI/2 C-2050/2 HEMA | IPDI | 83.01 | C-2050 | 367.65 | 984.2 | HEMA | 49.34 | XK-672 | 0.125 | 0.200 |
| PE-35 | 4 IPDI/2 C-2050/2 HEMA | IPDI | 83.01 | C-2050 | 367.65 | 984.2 | HEMA | 49.34 | XK-672 | 0.125 | 0.200 |
| PE-36 | 4 IPDI/2 C-2050/2 HEMA | IPDI | 83.01 | C-2050 | 367.65 | 984.2 | HEMA | 49.34 | XK-672 | 0.125 | 0.200 |
| PE-37 | 4 IPDI/2 C-2090/2 HEMA | IPDI | 125.16 | C-2090 | 550.45 | 977.35 | HEMA | 74.40 | XK-672 | 0.125 | 0.200 |
| PE-38 | 4 IPDI/2 C-3090/2 HEMA | IPDI | 90.85 | C-3090 | 605.15 | 1480.21 | HEMA | 54.00 | XK-672 | 0.125 | 0.200 |
| PE-39 | 4 IPDI/2.5 C-2090/1.5 HEMA | IPDI | 108.02 | C-2090 | 593.83 | 977.35 | HEMA | 48.15 | XK-672 | 0.125 | 0.200 |
| PE-40 | 4 IPDI/3 C-2090/1 HEMA | IPDI | 95.00 | C-2090 | 626.76 | 977.35 | HEMA | 28.24 | XK-672 | 0.125 | 0.200 |
| PE-41 | 4 IPDI/2 C-1090/2 HEMA | IPDI | 117.78 | C-1090 | 262.21 | 494.71 | HEMA | 70.01 | XK-672 | 0.113 | 0.180 |
| PE-42 | 4 IPDI/2.5 C-1090/1.5 HEMA | IPDI | 106.42 | C-1090 | 296.14 | 494.71 | HEMA | 47.44 | XK-672 | 0.113 | 0.180 |
| PE-43 | 4 IPDI/3 C-1090/1 HEMA | IPDI | 97.06 | C-1090 | 324.10 | 494.71 | HEMA | 28.85 | XK-672 | 0.113 | 0.180 |
| PE-44 | 4 IPDI/2 C-2050/2 HEMA | IPDI | 248.55 | C-2050 | 1100.80 | 984.2 | HEMA | 150.65 | XK-672 | 0.375 | 0.600 |
| PE-45 | 4 IPDI/2 NL2030B/2 HEMA | IPDI | 97.35 | NL2030B | 442.80 | 1010.8 | HEMA | 59.86 | XK-672 | 0.15 | 0.240 |
| PE-46 | 4 IPDI/2 NL2005B/2 HEMA | IPDI | 95.91 | NL2005B | 445.11 | 1031.25 | HEMA | 58.98 | XK-672 | 0.15 | 0.240 |
| PE-47 | 4 IPDI/2 NL2010DB/2 HEMA | IPDI | 98.25 | NL2010DB | 441.34 | 998.22 | HEMA | 60.41 | XK-672 | 0.15 | 0.240 |
| PE-48 | H12MDI/HEMA | H12MDI | 310.25 | | | | HEMA | 324.73 | XK-672 | 0.159 | 0.254 |
| PE-49 | 4 IPDI/2 C-3090/1 HEMA/1 G-AC-MAC | IPDI | 71.35 | C-3090 | 470.32 | 1464.75 | HEMA/ G-AC-MAC | 22.04/ 36.28 | XK-672 | 0.159 | 0.254 |
| PE-50 | 4 IPDI/2 C-3090/2 G-AC-MAC | IPDI | 69.70 | C-3090 | 459.42 | 1467.75 | G-AC-MAC | 72.49 | XK-672 | 0.159 | 0.254 |

*add diol over 1.5 h

TABLE 3

Preparative Examples of Diisocyanates Capped with Polyols, then Reacted with Isocyanato (meth)acrylates (containing 250 ppm XK-672 catalyst and 400 ppm BHT in all examples, *250 ppm DBTDL)

| Sample | Designation | Diisocyanate Type | g | Diol Type | g | OH EW | Isocyanato (meth)-acrylate Type | g |
|---|---|---|---|---|---|---|---|---|
| PE-51 | 2 IPDI/4 C-1090/2 IEM* | IPDI | 44.40 | C-1090 | 390.51 | 488.67 | IEM | 65.09 |
| PE-52 | 2 IPDI/4 C-2050/2 IEM | IPDI | 24.77 | C-2050 | 438.90 | 984.2 | IEM | 36.32 |

TABLE 3-continued

Preparative Examples of Diisocyanates Capped with Polyols, then Reacted with Isocyanato (meth)acrylates (containing 250 ppm XK-672 catalyst and 400 ppm BHT in all examples, *250 ppm DBTDL)

| Sample | Designation | Diisocyanate Type | g | Diol Type | g | OH EW | Isocyanato (meth)-acrylate Type | g |
|---|---|---|---|---|---|---|---|---|
| PE-53 | 2 MDI/4 C-1090/2 IEM | MDI | 10.31 | C-1090 | 80.61 | 488.67 | IEM | 13.44 |
| PE-54 | 2 IPDI/4 C-1090/1 IEM/1 BEI | IPDI | 8.58 | C-1090 | 75.44 | 488.67 | IEM-6.29 | BEI-9.69 |
| PE-55 | 2 IPDI/4 C-1090/2 BEI | IPDI | 8.29 | C-1090 | 72.96 | 488.67 | BEI | 18.75 |

TABLE 4

Preparative Examples of Diol (Meth)Acrylate Based Polyurethane (Meth)Acrylates (containing 250 ppm XK-672 catalyst and 400 ppm BHT in all examples)

| Sample | Designation | Isocyanate Type or type-g | Diol Type or type-g | Diol Type or type-g | Diol g or type-g | Diol Acrylate IEM-DEA unless otherwise noted g | Hydroxy functional (meth)-acrylate Type | G | Type |
|---|---|---|---|---|---|---|---|---|---|
| PE-56 | 4 IPDI/1 IEM-DEA/2 C-2050/1 HEMA | IPDI | 16.58 | C-2050 | 73.42 | 4.85 | HEMA | 5.15 | 1 |
| PE-57 | 2 IPDI/1 IEM-DEA/3 C-2050/2 IEM | IPDI-6.13 IEM-8.9 | | C-2050 | 81.39 | 3.59 | HEMA | 0 | 2 |
| PE-58 | 4 IPDI/1 IEM-DEA/2 C-1090/1 HEMA | IPDI | 26.3 | C-1090 | 57.84 | 7.7 | HEMA | 8.16 | 1 |
| PE-59 | 4 IPDI/1 IEM-DEA/2 C-2050R/1 HEMA | IPDI | 25.01 | C-2050R | 110.75 | 7.32 | HEMA | 6.93 | 1 |
| PE-60 | 4 IPDI/1 IEM-DEA/2 C-2050R/.5 HEMA/.5 G-Ac-Mac | IPDI | 16.31 | C-2050R | 72.22 | 4.78 | HEMA G-Ac-Mac | 2.53 4.17 | 1 |
| PE-61 | 4 MDI/1 IEM-DEA 2 C-2050R/1 HEMA | MDI | 18.27 | C-2050R | 71.93 | 4.76 | HEMA | 5.04 | 1 |
| PE-62 | 4 IPDI/1.17 IEM-DEA/2 C-3090/1 HEMA | IPDI | 12.13 | C-3090 | 80.8 | 4.15 | HEMA | 3.76 | 1 |
| PE-63 | 4 IPDI/0.5 IEM-DEA/1.5 C-2050/2 HEMA | IPDI | 19.65 | C-2050 | 65.27 | 2.88 | HEMA | 12.2 | 1 |
| PE-64 | 4 IPDI/2 IEM-DEA/1 C-2050/1 HEMA | IPDI | 24.33 | C-2050 | 53.87 | 14.25 | HEMA | 7.55 | 1 |
| PE-65 | 4 IPDI/1 IEM-DEA/1 C-2050/1 P-2010/1 HEMA | IPDI | 16.41 | C-2050-36.35 | P-2010-37.34 | 4.81 | HEMA | 5.09 | 1 |
| PE-66 | 2 IPDI/1 IEM-DEA/3 C-2050/1 IEM/1 BEI | IPDI-5.98 IEM-4.34 | BEI-6.7 | C2-050 | 79.48 | 3.5 | BEI | 0 | 2 |
| PE-67 | 4 IPDI/IEM- EO/2 -DEA - C-2050R/1 HEMA | IPDI | 16.44 | C2-050R | 72.82 | IEM- EO/2 -DEA 5.63 | HEMA | 5.1 | 1 |
| PE-68 | 4 IPDI/1 IEM-DEA/2 C-2050/1 HEMA | IPDI | 16.58 | C-2050 | 73.42 | 4.85 | HEMA | 5.15 | 1 |
| PE-69 | 4 IPDI/1 IEM-DEA/2 C-2050/1 HEMA | IPDI | 16.58 | C-2050 | 73.42 | I4.85 | HEMA | 5.15 | 1 |
| PE-70 | 4 IPDI/1 IEA-DEA/2 C-2050/1 HEA | IPDI | 16.71 | C-2050 | 74.03 | IEA-DEA -4.63 | HEA | 4.63 | 1 |
| PE-71 | 4 IPDI/ACAC-MA/2 C-2050/1 HEMA | IPDI | 16.03 | C-2050 | 70.98 | ACAC-MA-8.01 | HEMA | 4.97 | 1 |
| PE-72 | 4 IPDI/1 GMMA/2 C-2050/1 HEMA | IPDI | 16.91 | C-2050 | 74.88 | GMMA-2.97 | HEMA | 5.25 | 1 |

TABLE 5

Preparative Examples of Polycarbonate and Polyester Diol Polyurethane (Meth)acrylates
(containing 250 ppm XK-672 catalyst and 400 ppm BHT in all examples)

| Sample | Designation | Isocyanate Type or type-g | | Diol Type or type-g | g or type-g | OH EW | Hydroxy functional (meth)-acrylate Type | g |
|---|---|---|---|---|---|---|---|---|
| PE-73 | 4 IPDI/2 C-2050/2 HEMA | IPDI | 496.37 | C-2050 | 2198.4 | 984.2 | HEMA | 305.23 |
| PE-74 | 4 IPDI/2 C-2050/2 HEMA | IPDI | 1588.39 | C-2050 | 7034.88 | 984.2 | HEMA | 976.73 |
| PE-75 | 4 IPDI/2 P-2010/2 HEMA | IPDI | 324.91 | P-2010 | 1475.29 | 1009 | HEMA | 199.80 |
| PE-76 | 4 IPDI/2 C-2050/2 HEMA | IPDI | 1648.17 | C-2050 | 7338.35 | 984.2 | HEMA | 1013.49 |
| PE-77 | 4 IPDI/2 C-2050/2 HEMA | IPDI | 82.65 | C-2050 | 366.05 | 984.2 | HEMA | 51.31 |
| PE-78 | 4 IPDI/0.5 P-2010/1.5 C-2050/2 HEMA | IPDI | 16.45 | P-2010-18.71 | P-2050 54.63 | P-2010-1011 C-2050 984.2 | HEMA | 10.21 |
| PE-79 | 4 IPDI/1 P-2010/1 C-2050/2 HEMA | IPDI | 16.37 | P-2010-37.23 | P-2050 36.24 | P-2010-1011 C-2050 984.2 | HEMA | 10.16 |
| PE-88 | 4 IPDI/3 C-590/1 HEMA | IPDI | 33.57 | C-590 | 56.01 | 247.14 | HEMA | 10.42 |

TABLE 6

Preparative Examples of Polyol, and Isocyanato (meth)acrylate
(250 ppm DBTDL catalyst and 400 ppm BHT in all examples)

| Sample | Designation | Isocyanate Type or type-g | Type or type-g | Diol Type | g | OH EW |
|---|---|---|---|---|---|---|
| PE-80 | C-2050/IEM | IEM | 68.07 | C-2050 | 431.93 | 984.5 |
| PE-81 | C-2050/IEA | IEA | 141.12 | C-2050 | 437.31 | 984.5 |
| PE-82 | C-3090/IEA | IEA | 43.52 | C-3090 | 456.48 | 1480.21 |
| PE-83 | C-2090/IEA | IEA | 63.37 | C-2090 | 436.63 | 972.27 |
| PE-84 | P-2010/IEM | IEM | 39.98 | P-2010 | 260.02 | 1009 |
| PE-85 | P-1010/IEM | IEM | 227.8 | P-1010 | 227.80 | 489.5 |

TABLE 7

Adducts of Diisocyanates and Hydroxy functional
(Meth)acrylates (containing 250 ppm XK-672
catalyst and 400 ppm BHT in all examples)

| Sample | Designation | Diisocyanate Type | g | (meth)-acrylate mono-ol Type | g |
|---|---|---|---|---|---|
| PE-86 | IPDI/HEMA | IPDI | 685.29 | HEMA | 846.81 |
| PE-87 | IPDI/HEA | IPDI | 332.93 | HEA | 388.05 |

Determination of HEMA-IPDI-HEMA Oligomer Concentration.

Determination of a concentration of HEMA-IPDI-HEMA oligomer was performed by liquid chromatography-mass spectrometry (LC/MS) on an Agilent 1260 Infinity Series liquid chromatography system (Agilent Technologies, Waldbronn, Germany) using an Agilent Poroshell 120 SB-C8 2.1 mm×50 mm 2.7 micrometer column eluted at 40° C. with a flow rate of 0.5 mL per minute. 2 microliter samples were injected and eluted with a linear gradient as described below. The water was Omnisolv HPLC grade from EMD Millipore, a part of Merck KGaA. The re-equilibration time between experiments was 5 minutes. Detection was with an Agilent 6130 Quadrupole LC/MS detector with electrospray ionization. Sample quantification was done by integration of the chromatographic peak detected at 500.3 m/z (M-NH$_4$). Mass spectrometer parameters were in atmospheric pressure ionization-electrospray (API-ES) mode: capillary voltage 4 kV, nebulizer gas pressure 50 psig (345 kPa gauge), drying gas flow rate 10 liters per minute, drying gas temperature 300° C.

TABLE 8

Solvent elution gradient

| Solvent | Time (min) |
|---|---|
| 6 mM ammonium formate in water | 0 |
| 6 mM ammonium formate in 98% acetonitrile/2% water | 3 |
| 6 mM ammonium formate in 98% acetonitrile/2% water | 5 |
| 89% acetonitrile 10% tetrahydrofuran 1% formic acid | 6 |
| 89% acetonitrile 10% tetrahydrofuran 1% formic acid | 8 |
| 6 mM ammonium formate in water | 9 |

Calibration samples were prepared by dissolution of 0.1009 g of material polyurethane acrylate PE-33 in a 100 mL volumetric flask using ethyl acetate. This solution was then diluted 1 mL into a 100 mL volumetric flask using acetonitrile to produce dilution 1. Dilution 1 was further diluted to 2.02, 0.505, 0.101 and 0.0121 ppm concentrations in acetonitrile and filtered through 0.22 micron PTFE syringe filters (Fisher Brand, Thermo Fisher Scientific, Hampton, NH). The calibration curve was linear from 2.02-0.0121 ppm. Calibrations were performed directly preceding analytical samples.

Analytical samples were prepared by dissolution of 0.1-0.3 g of material in a 100 mL volumetric flask using ethyl acetate. This solution was then diluted 1 mL into a 100 mL volumetric flask using acetonitrile to produce dilution 1. Dilution 1 was filtered through 0.22 micron PTFE syringe filters (Fisher Brand) and analyzed as discussed above. The results for each sample are shown in Table 9 below.

TABLE 9

| Sample | Polyol | Catalyst | IPDI:Polyol:HEMA eq ratio | % HEMA-IDPI-HEMA in polymer (does not include IBOMA diluent if present) |
|---|---|---|---|---|
| PE-13 | C-3090 | DBTDL | 4:2:2 | 5.0% |
| PE-30 | C-3090 | DBTDL | 4:1.5:2.5 | 11.1% |
| PE-31 | C-3090 | DBTDL | 4:1:3 | 20.7% |
| PE-37 | C-2090 | XK-672 | 4:2:2 | 5.4% |
| PE-38 | C-3090 | XK-672 | 4:2:2 | 3.8% |
| PE-7 | C-2050 | DBTDL | 4:2:2 | 5.6% |

TABLE 9-continued

| Sample | Polyol | Catalyst | IPDI:Polyol:HEMA eq ratio | % HEMA-IDPI-HEMA in polymer (does not include IBOMA diluent if present) |
|---|---|---|---|---|
| PE-9 | C-2050 | DBTDL | 4:2:2 | 5.5% |
| PE-32 | C-2050 | BiN | 4:2:2 | 5.7% |
| PE-25 | C-1090 | DBTDL | 4:2:2 | 8.6% |
| PE-39 | C-2090 | XK-672 | 4:2.5:1.5 | 3.0% |
| PE-40 | C-2090 | XK-672 | 4:3:1 | 0.3% |
| PE-41 | C-1090 | XK-672 | 4:2:2 | 7.5% |
| PE-42 | C-1090 | XK-672 | 4:2.5:1.5 | 1.8% |
| PE-43 | C-1090 | XK-672 | 4:3:1 | 0.1% |
| PE-44 | C-2050 | XK-672 | 4:2:2 | 5.0% |

General Procedure for Formulation Preparation

Formulations were prepared by weighing the components (indicated in Tables 10-36) in an amber jar, followed by rolling on a roller (having the trade designation "OLDE MIDWAY PRO18" and manufactured by Olde Midway) at 60° C. until mixed.

TABLE 10

Example formulations (amounts in parts by weight)

| Components | EX-1 | EX-2 | EX-3 | EX-4 | EX-5 | EX-6 |
|---|---|---|---|---|---|---|
| PE-41 | 50 | | | | | |
| PE-42 | | 50 | | | | |
| PE-43 | | | 50 | | | |
| PE-37 | | | | 50 | | |
| PE-39 | | | | | 50 | |
| PE-40 | | | | | | 50 |
| IBOMA | 50 | 50 | 50 | 50 | 50 | 50 |
| TPO | 2 | 2 | 2 | 2 | 2 | 2 |

TABLE 11

Example formulations (amounts in parts by weight)

| Components | EX-7 | EX-8 | EX-9 | EX-10 | EX-11 | EX-12 | EX-13 | EX-14 |
|---|---|---|---|---|---|---|---|---|
| PE-19 | 50 | | | | | | | |
| PE-7 | | 50 | | | | | | |
| PE-22 | | | 50 | | | | | |
| PE-20 | | | | 50 | | | | |
| PE-21 | | | | | 50 | | | |
| PE-23 | | | | | | 50 | | |
| PE-24 | | | | | | | 50 | |
| PE-6 | | | | | | | | 50 |
| IBOMA | 50 | 50 | 50 | 50 | 50 | 50 | 50 | 50 |
| TPO | 2 | 2 | 2 | 2 | 2 | 2 | 2 | 2 |
| BHT | | 0.025 | | | | | | |

TABLE 12

Example formulations (amounts in parts by weight)

| Components | EX-15 | EX-16 | EX-17 | EX-18 | EX-19 |
|---|---|---|---|---|---|
| PE-38 | 50 | | | | |
| PE-31 | | 50 | | | |
| PE-26 | | | 50 | | |
| PE-8 | | | | 50 | |
| PE-28 | | | | | 50 |
| IBOMA | 50 | 50 | 50 | 50 | 50 |
| TPO | 2 | 2 | 2 | 2 | 2 |

TABLE 13

Example formulations (amounts in parts by weight)

| Components | EX-20 | EX-21 | EX-22 | EX-23 | EX-24 | EX-25 |
|---|---|---|---|---|---|---|
| PE-25 | 25 | 18 | | 10 | 15 | |
| PE-13 | 25 | 32 | 25 | | 35 | |
| PE-19 | | | 25 | | | |
| PE-26 | | | | 40 | | |
| PE-30 | | | | | | 40 |
| PE-14 | | | | | | 10 |
| AdMA | | | | | | 50 |
| IBOMA | 50 | 50 | 50 | 50 | 50 | |
| TPO | 2 | 2 | 2 | 2 | 2 | 2 |

TABLE 14

Example formulations (amounts in parts by weight)

| Components | EX-26 | EX-27 | EX-28 | EX-29 | EX-30 |
|---|---|---|---|---|---|
| PE-13 | 45 | 40 | | | |
| PE-30 | | | 47.5 | | |
| PE-32 | | | | 47.5 | |
| PE-33 | 5 | 10 | 2.5 | 2.5 | 5 |
| PE-11 | | | | | 45 |
| IBOMA | 50 | 50 | 50 | 50 | 50 |
| TPO | 2 | 2 | 2 | 2 | 2 |

TABLE 15

Example formulations (amounts in parts by weight)

| Components | EX-31 | EX-32 | EX-33 | EX-34 | EX-35 | EX-36 |
|---|---|---|---|---|---|---|
| PE-5 | 40 | 40 | 40 | 40 | | |
| PE-7 | | | | | 40 | 40 |
| PE-9 | 10 | | | | | |
| PE-10 | | 10 | | | | |
| PE-11 | | | 10 | | | |
| PE-12 | | | | 10 | | |
| PE-15 | | | | | 10 | |
| PE-16 | | | | | | 10 |
| IBOMA | 50 | 50 | 50 | 50 | 50 | 50 |
| TPO | 2 | 2 | 2 | 2 | 2 | 2 |

TABLE 16

Example formulations (amounts in parts by weight)

| Components | EX-37 | EX-38 | EX-39 | EX-40 |
|---|---|---|---|---|
| PE-7 | 40 | 40 | | |
| PE-5 | | | 45 | |
| PE-32 | | | | 50 |
| C-590 diol MA | 10 | | | |
| C-2050 diol MA | | 10 | | |
| DDDMA | | | 5 | |
| HDDMA | | | | 10 |
| IBOMA | 50 | 50 | 50 | 40 |
| TPO | 2 | 2 | 2 | 2 |

TABLE 17

Example formulations (amounts in parts by weight)

| Components | EX-41 | EX-42 | EX-43 | EX-44 | EX-45 | EX-46 | EX-47 | EX-48 | EX-49 |
|---|---|---|---|---|---|---|---|---|---|
| PE-19 | 50 | | | | | | | | |
| PE-5 | | 40 | 60 | | | | | | |
| PE-32 | | | | 50 | 50 | 50 | 50 | | |
| PE-14 | | | | | | | | 45 | |
| PE-33 | | | | | | | | 5 | |
| PE-7 | | | | | | | | | 50 |
| IBOMA | | 60 | 40 | | | | | 50 | |
| DiCPMA | 50 | | | | 50 | | | | |
| AdMA | | | | 50 | | | | | |
| tBuCHMA | | | | | | 50 | | | |
| CHMA | | | | | | | 50 | | |
| TMCHMA | | | | | | | | | 50 |
| TPO | 2 | 2 | 2 | 2 | 2 | 2 | 2 | 2 | 2 |

TABLE 18

Example formulations (amounts in parts by weight)

| Components | EX-50 | EX-51 | EX-52 | EX-53 | EX-54 | EX-55 |
|---|---|---|---|---|---|---|
| PE-19 | 50 | | | | | |
| PE-22 | | 50 | | | | |
| PE-27 | | | 50 | | | |
| PE-34 | | | | 50 | | |
| PE-35 | | | | | 50 | |
| PE-36 | | | | | | 50 |
| IBOMA | | | 50 | 50 | 50 | 50 |
| IBOA | 50 | 50 | | | | |
| TPO | 2 | 2 | 2 | 2 | 2 | 2 |

TABLE 19

Example formulations (amounts in parts by weight)

| Components | EX-79 | EX-80 | EX-81 | EX-82 | EX-83 | EX-84 |
|---|---|---|---|---|---|---|
| PE-13 | | | | 45 | | |
| PE-45 | 50 | | | | | |
| PE-46 | | 50 | | | | |
| PE-47 | | | 50 | | | |
| PE-48 | | | | 5 | | |
| PE-49 | | | | | 50 | |
| PE-50 | | | | | | 50 |
| IBOMA | 50 | 50 | 50 | 50 | 50 | 50 |
| TPO | 2 | 2 | 2 | 2 | 2 | 2 |

TABLE 20

Example formulations (amounts in parts by weight)

| Components | EX-90 | EX-91 | EX-92 | EX-93 | EX-94 | EX-95 | EX-96 |
|---|---|---|---|---|---|---|---|
| PE-15 | 60 | 60 | | | | | |
| PE-11 | | | 50 | 45 | 50 | 45 | 45 |
| PE-86 | | 5 | | 5 | 5 | 10 | |
| PE-48 | | | | | | | 5 |
| IBOMA | 40 | 35 | 50 | 50 | 45 | 45 | 50 |
| TPO | 2 | 2 | 2 | 2 | 2 | 2 | 2 |

TABLE 21

Example formulations (amounts in parts by weight)

| Components | EX-97 | EX-98 | EX-99 | EX-100 | EX-101 | EX-102 | EX-103 |
|---|---|---|---|---|---|---|---|
| PE-11 | 45 | 50 | | | | | |
| PE-80 | | | 40 | | | | |

TABLE 21-continued

Example formulations (amounts in parts by weight)

| Components | EX-97 | EX-98 | EX-99 | EX-100 | EX-101 | EX-102 | EX-103 |
|---|---|---|---|---|---|---|---|
| PE-9 | | | | 50 | 50 | | |
| PE-10 | | | | | | 50 | 50 |
| PE-87 | 5 | | | | | | |
| PE-86 | | 5 | 10 | | 5 | | 5 |
| IBOMA | 50 | | | 50 | 45 | 50 | 45 |
| AdMA | | 45 | | | | | |
| CHMA | | | 50 | | | | |
| TPO | 2 | 2 | 2 | 2 | 2 | 2 | 2 |

TABLE 22

Example formulations (amounts in parts by weight)

| Components | EX-104 | EX-105 | EX-106 | EX-107 | EX-108 | EX-109 | EX-110 |
|---|---|---|---|---|---|---|---|
| PE-14 | 50 | 45 | 45 | | | | |
| PE-12 | | | | 50 | 50 | | |
| PE-81 | | | | | | 45 | 45 |
| PE-86 | | 5 | 10 | | 5 | 5 | |
| PE-87 | | | | | | | 5 |
| IBOMA | 50 | 50 | 45 | 50 | 45 | 50 | 50 |
| TPO | 2 | 2 | 2 | 2 | 2 | 2 | 2 |

TABLE 23

Example formulations (amounts in parts by weight)

| Components | EX-111 | EX-112 | EX-113 | EX-114 | EX-115 | EX-116 | EX-117 |
|---|---|---|---|---|---|---|---|
| PE-81 | 35 | | | | | | |
| PE-83 | | 45 | | | | | |
| PE-82 | | | 45 | | | | |
| PE-51 | | | | 50 | | | |
| PE-52 | | | | | 50 | | |
| PE-53 | | | | | | 50 | |
| PE-54 | | | | | | | 50 |
| PE-87 | 15 | | | | | | |
| PE-86 | | 5 | 5 | | | | |
| IBOA | 50 | | | | | | |
| IBOMA | | 50 | 50 | 50 | 50 | 50 | 50 |
| TPO | 2 | 2 | 2 | 2 | 2 | 2 | 2 |

TABLE 24

Example formulations (amounts in parts by weight)

| Components | EX-118 | EX-119 | EX-120 | EX-121 | EX-122 | EX-123 | EX-124 |
|---|---|---|---|---|---|---|---|
| PE-55 | 60 | | | | | | |
| PE-74 | | 22.5 | 30 | 27.5 | | | |
| PE-75 | | 22.5 | 20 | 17.5 | | | |
| PE-86 | | 5 | | 5 | | | |
| PE-78 | | | | | 50 | | |
| PE-79 | | | | | | 50 | |
| PE-7 | | | | | | | 40 |
| PE-14 | | | | | | | 10 |
| IBOMA | 40 | 50 | 50 | 50 | 50 | 50 | 50 |
| TPO | 2 | 2 | 2 | 2 | 2 | 2 | 2 |

TABLE 25

Example formulations (amounts in parts by weight)

| Components | EX-125 | EX-126 | EX-127 | EX-128 | EX-129 | EX-130 | EX-131 |
|---|---|---|---|---|---|---|---|
| PE-7 | 40 | 40 | | | | | |
| PE-15 | 10 | | | 15 | | | |

TABLE 25-continued

Example formulations (amounts in parts by weight)

| Components | EX-125 | EX-126 | EX-127 | EX-128 | EX-129 | EX-130 | EX-131 |
|---|---|---|---|---|---|---|---|
| PE-16 |  | 10 | 15 |  |  |  |  |
| PE-73 |  |  | 48 | 40 | 42.85 | 40 | 40 |
| PE-11 |  |  |  |  | 10.71 | 5 | 10 |
| PE-86 |  |  | 5 | 5 | 5.35 | 5 | 5 |
| IBOMA | 50 | 50 | 32 | 40 | 41.08 | 50 | 45 |
| TPO | 2 | 2 | 2 | 2 | 2 | 2 | 2 |

TABLE 26

Example formulations (amounts in parts by weight)

| Components | EX-132 | EX-133 | EX-134 | EX-135 | EX-136 | EX-137 | EX-138 |
|---|---|---|---|---|---|---|---|
| PE-73 | 40 | 30 | 20 | 30 | 30 | 30 | 30 |
| PE-11 | 15 | 20 |  |  |  |  |  |
| PE-80 |  |  | 30 | 20 | 20 | 20 | 20 |
| PE-86 | 5 | 10 | 10 |  |  | 10 | 10 |
| PE-48 |  |  |  | 10 |  |  |  |
| PE-87 |  |  |  |  | 10 |  |  |
| IBOMA | 40 | 40 | 40 | 40 | 40 |  |  |
| AdMA |  |  |  |  |  | 40 |  |
| CHMA |  |  |  |  |  |  | 40 |
| TPO | 2 | 2 | 2 | 2 | 2 | 2 | 2 |

TABLE 27

Example formulations (amounts in parts by weight)

| Components | EX-139 | EX-140 | EX-141 | EX-142 | EX-143 | EX-144 | EX-145 |
|---|---|---|---|---|---|---|---|
| PE-73 | 30 | 30 | 30 | 40 | 30 | 40 |  |
| PE-74 |  |  |  |  |  |  | 40 |
| PE-9 | 20 |  |  |  |  |  |  |
| PE-10 |  | 20 |  |  |  |  |  |
| PE-12 |  |  | 20 |  |  |  |  |
| PE-14 |  |  |  | 10 |  |  |  |
| PE-80 |  |  |  |  | 20 |  |  |
| PE-81 |  |  |  |  |  | 5 |  |
| PE-83 |  |  |  |  |  |  | 10 |
| PE-86 | 10 | 10 | 10 | 5 |  | 5 | 5 |
| PE-87 |  |  |  |  | 10 |  |  |
| IBOMA | 40 | 40 | 40 | 45 | 40 | 50 | 45 |
| TPO | 2 | 2 | 2 | 2 | 2 | 2 | 2 |

TABLE 28

Example formulations (amounts in parts by weight)

| Components | EX-146 | EX-147 | EX-148 | EX-149 | EX-150 | EX-151 | EX-152 |
|---|---|---|---|---|---|---|---|
| PE-73 |  | 40 |  |  | 30 |  |  |
| PE-74 | 40 |  |  |  |  |  |  |
| PE-22 |  |  | 40 | 35 |  |  |  |
| PE-82 | 5 |  |  |  |  |  |  |
| PE-81 |  | 5 | 10 | 5 |  |  |  |
| PE-84 |  |  |  |  | 20 |  |  |
| PE-56 |  |  |  |  |  | 50 |  |
| PE-65 |  |  |  |  |  |  | 50 |
| PE-86 | 5 |  |  |  | 10 |  |  |
| PE-87 |  | 5 | 5 | 10 |  |  |  |
| IBOMA | 50 | 50 | 45 |  | 40 | 50 | 50 |
| IBOA |  |  |  | 50 |  |  |  |
| TPO | 2 | 2 | 2 | 2 | 2 | 2 | 2 |

TABLE 29

Example formulations (amounts in parts by weight)

| Components | EX-153 | EX-154 | EX-155 | EX-156 | EX-157 | EX-158 | EX-159 | EX-160 |
|---|---|---|---|---|---|---|---|---|
| PE-58 | 60 | | | | | | | |
| PE-59 | | 50 | | | | | | |
| PE-60 | | | 50 | | | | | |
| PE-61 | | | | 50 | | | | |
| PE-62 | | | | | 50 | | | |
| PE-63 | | | | | | 50 | | |
| PE-70 | | | | | | | 35 | 35 |
| PE-86 | | | | | | | | 5 |
| IBOMA | 40 | 50 | 50 | 50 | 50 | 50 | | |
| IBOA | | | | | | | 65 | 60 |
| TPO | 2 | 2 | 2 | 2 | 2 | 2 | 2 | 2 |

TABLE 30

Example formulations (amounts in parts by weight)

| Components | EX-161 | EX-162 | EX-163 | EX-164 | EX-165 | EX-166 | EX-167 |
|---|---|---|---|---|---|---|---|
| PE-71 | 55 | | | | | | |
| PE-72 | | 50 | | | | | |
| PE-57 | | | 50 | | | | |
| PE-66 | | | | 50 | | | |
| PE-67 | | | | | 50 | | |
| PE-68 | | | | | | 50 | |
| PE-69 | | | | | | | 50 |
| IBOMA | 45 | 50 | 50 | 50 | 50 | | |
| IBOA | | | | | | 50 | |
| CHMA | | | | | | | 50 |
| TPO | 2 | 2 | 2 | 2 | 2 | 2 | 2 |

TABLE 31

Example formulations (amounts in parts by weight)

| Components | EX-168 | EX-169 | EX-170 | EX-171 | EX-172 | EX-173 | EX-174 |
|---|---|---|---|---|---|---|---|
| PE-25 | 45 | 55 | 40 | 55 | 50 | 50 | 50 |
| PE-86 | 10 | 10 | 10 | 10 | | 10 | 5 |
| PEMA | 45 | 35 | 50 | | | | |
| THFMA | | | | 35 | | | |
| IBuMA | | | | | 50 | | |
| tBuA | | | | | | 40 | |
| BnMA | | | | | | | 45 |
| TPO | 2 | 2 | 2 | 2 | 2 | 2 | 2 |

TABLE 32

Example formulations (amounts in parts by weight)

| Components | EX-175 | EX-176 | EX-177 | EX-178 | EX-179 | EX-180 |
|---|---|---|---|---|---|---|
| PE-25 | 40 | | | | | |
| PE-77 | | 50 | 50 | 50 | | |
| PE-76 | | | | | 40 | |
| PE-88 | | | | | | 60 |
| PE-86 | 10 | | | | | |
| Exothane 10 | | | | 10 | | |
| nPrMA | 50 | | | | | |
| IBOMA | | 40 | 30 | 25 | 50 | 40 |
| HEMA | | 10 | 20 | 25 | | |
| TPO | 2 | 2 | 2 | 2 | 2 | 2 |

TABLE 33

Example formulations (amounts in parts by weight)

| Components | EX-181 | EX-182 | EX-183 | EX-184 | EX-185 | EX-186 | EX-187 |
|---|---|---|---|---|---|---|---|
| PE-11 | 40 | | | | | | |
| PE-81 | | 50 | 40 | 38 | | | 10 |
| PE-82 | | | | | | 50 | |
| PE-87 | | | 10 | 12 | | | 5 |

TABLE 33-continued

Example formulations (amounts in parts by weight)

| Components | EX-181 | EX-182 | EX-183 | EX-184 | EX-185 | EX-186 | EX-187 |
|---|---|---|---|---|---|---|---|
| PE-86 | 5 | | | | | | |
| PE-83 | | | | | 50 | | |
| PE-22 | | | | | | | 35 |
| CHMA | 50 | | | | | | |
| IBOMA | | 50 | | | 50 | 50 | 50 |
| IBOA | | | 50 | 50 | | | |
| TPO | 2 | 2 | 2 | 2 | 2 | 2 | 2 |

TABLE 34

Example formulations (amounts in parts by weight)

| Components | EX-85 | EX-87 | EX-88 | EX-89 |
|---|---|---|---|---|
| PE-32 | 50 | 50 | 50 | |
| PE-5 | | | | 70 |
| PEMA | | 50 | | |
| THFMA | | | 50 | |
| tBuCHMA | 50 | | | |
| IBOMA | | | | 30 |
| TPO | 2 | 2 | 2 | 2 |
| BHT | | | | 0.025 |

TABLE 35

Comparative example formulations (amounts in parts by weight)

| Components | CE-1 | CE-2 | CE-3 | CE-4 |
|---|---|---|---|---|
| PE-32 | 50 | 50 | | |
| Exothane 10 | | | 30 | 50 |
| CEA | | | 50 | |
| NVP | | | 20 | |
| IBOMA | | | | 50 |
| EHMA | | 50 | | |
| PEMA | | | | |
| PEG600DMA | 50 | | | |
| THFMA | | | | |
| TPO | 2 | 2 | 2 | 2 |

TABLE 36

Comparative example formulations (amounts in parts by weight)

| Components | CE-5 | CE-6 | CE-7 | CE-8 | CE-9 |
|---|---|---|---|---|---|
| Exothane 108 | 50 | | | | |
| PE-18 | | 50 | | | |
| PE-17 | | | 50 | | |
| PE-5 | | | | 30 | |
| PE-4 | | | | | 50 |
| IBOMA | 50 | 50 | 50 | 70 | 50 |
| TPO | 2 | 2 | 2 | 2 | 2 |
| BHT | | 0.025 | | 0.025 | |

Polymer/Oligomer Molecular Weight Characterization Method:

The molecular weights of the oligomers and the polymers were characterized using gel permeation chromatography (GPC). The GPC equipment consisted of an e2695 Separation Module and a 2414 dRI detector, both from Waters Corporation (Milford, MA). It was operated at a flow rate of 0.6 mL/min using tetrahydrofuran as the eluent. The GPC column was a HSPgel HR MB-M column also from Waters Corporation. The column compartment and differential refractive index detector were set to 35° C. The molecular weight standards were EasiVial PMMA from Agilent Technologies (The $M_v$ values of the PMMA molecular weight standards used in the calibration curve ranged from 550 D to 1,568,000 g/mol.) The relative number average molecular weight (Mn) and weight average molecular weight (Mn) of selected oligomers/polymers are tabulated below in Table 37, in kiloDaltons (kD):

TABLE 37

| Sample | Mn (kD) | Mw (kD) | Polydispersity |
|---|---|---|---|
| PE-6 | 4.3 | 18.1 | 4.2 |
| PE-7 | 3.5 | 12.1 | 3.4 |
| PE-8 | 3.5 | 12.4 | 3.5 |
| PE-9 | 3.0 | 7.5 | 2.5 |
| PE-10 | 3.1 | 7.4 | 2.4 |
| PE-11 | 3.1 | 8.1 | 2.6 |
| PE-12 | 3.3 | 8.7 | 2.6 |
| PE-13 | 4.3 | 17.9 | 4.1 |
| PE-14 | 4.5 | 11.5 | 2.6 |
| PE-17 | 1.6 | 6.3 | 4.1 |
| PE-18 | 3.8 | 12.9 | 3.4 |
| PE-19 | 2.1 | 8.9 | 4.3 |
| PE-20 | 5.0 | 16.4 | 3.3 |
| PE-21 | 3.7 | 14.3 | 3.9 |
| PE-22 | 3.1 | 11.6 | 3.7 |
| PE-23 | 3.9 | 17.0 | 4.4 |
| PE-24 | 3.4 | 14.0 | 4.1 |
| PE-25 | 2.0 | 5.6 | 2.8 |
| PE-26 | 2.9 | 12.8 | 4.3 |
| PE-27 | 3.3 | 14.0 | 4.3 |
| PE-28 | 2.8 | 12.3 | 4.4 |
| PE-29 | 3.6 | 11.5 | 3.2 |
| PE-30 | 2.9 | 12.9 | 4.4 |
| PE-31 | 2.0 | 9.8 | 4.9 |
| PE-32 | 3.9 | 12.1 | 3.1 |
| PE-33 | 4.1 | 14.4 | 3.5 |
| PE-35 | 3.5 | 12.9 | 3.7 |
| PE-36 | 3.6 | 12.0 | 3.4 |
| PE-39 | 7.4 | 21.8 | 3.0 |
| PE-40 | 11.3 | 30.5 | 2.7 |
| PE-41 | 2.8 | 6.3 | 2.2 |
| PE-42 | 3.9 | 9.1 | 2.3 |
| PE-43 | 6.3 | 15.8 | 2.5 |
| PE-44 | 4.6 | 12.8 | 2.8 |
| PE-45 | 14.3 | 24.6 | 1.7 |
| PE-46 | 15.6 | 25.8 | 1.8 |
| PE-47 | 18.3 | 32.1 | 1.8 |
| PE-56 | 7.2 | 20.3 | 2.8 |
| PE-58 | 4.8 | 10.6 | 2.2 |
| PE-59 | 9.5 | 22.8 | 2.4 |
| PE-60 | 8.8 | 21.6 | 2.5 |
| PE-61 | 10.1 | 24.6 | 2.4 |
| PE-62 | 13.9 | 35.0 | 2.5 |
| PE-63 | 4.6 | 10.4 | 2.3 |
| PE-64 | 5.2 | 14.4 | 2.8 |
| PE-65 | 9.0 | 21.8 | 2.4 |
| PE-57 | 6.3 | 12.0 | 1.9 |
| PE-66 | 6.6 | 12.1 | 1.8 |
| PE-67 | 8.8 | 20.9 | 2.4 |
| PE-68 | 8.1 | 21.4 | 2.6 |
| PE-69 | 5.7 | 19.5 | 3.4 |
| PE-70 | 7.6 | 20.5 | 2.7 |
| PE-71 | 9.4 | 20.8 | 2.2 |

TABLE 37-continued

| Sample | Mn (kD) | Mw (kD) | Polydispersity |
|---|---|---|---|
| PE-72 | 9.1 | 21.3 | 2.3 |
| PE-78 | 6.3 | 11.6 | 1.8 |
| PE-79 | 6.4 | 11.7 | 1.8 |
| PE-88 | 4.7 | 8.6 | 1.8 |

General Procedure of Formulation Casting and Curing

Each formulation indicated in Tables 10-36 was poured into a silicone dogbone mold (Type V mold of 1 mm thickness, ASTM D638-14) for preparing tensile specimens, and a rectangular mold of dimensions (9.4 mm×25.4 mm×1 mm) for DMA 3-point bend test specimens. A 2 mil (0.05 mm) polyethylene terephthalate (PET) release liner (obtained under the trade designation "SCOTCHPAK" from 3M Company (St. Paul, MN)) was rolled on the filled mold, and the filled mold along with the liner was placed between two glass plates held by binder clips. The formulation was cured in an Asiga Pico Flash post-curing chamber (obtained from Asiga USA, Anaheim Hills, CA) for 30 minutes. The specimens were removed from the mold followed by additional light exposure for 30 minutes using the Asiga Pico Flash post-curing chamber. Specimens were then kept in an oven set at 100° C. for 30 minutes. The dogbone specimens were conditioned in Phosphate-buffered saline (PBS, 1×, pH=7.4) for 24 hours at 37° C. The DMA 3-point bend test specimens were conditioned in deionized (DI) water for 48 hours at room temperature.

General Procedure for Determination of Loss Modulus and Tan Delta Using Dynamic Mechanical Analysis Dynamic mechanical analysis (DMA) was performed on rectangular cured samples (approximately 25.4 mm×9.4 mm×1 mm) using a TA Instruments model Q800 dynamic mechanical analyzer (TA Instruments (Newcastle, DE)) using a tension clamp in controlled strain mode, 0.2% strain, 0.02 N preload force, 125% force track, 1 Hz. Temperature was swept at a rate of 2° C./min from −40° C. to 200° C. Samples were immersed in deionized water at 37° C. for at least 24 hours, at which time the samples were fully saturated with water prior to testing and tested immediately after removal from water.

TABLE 38

Measured physical properties of samples.

| Sample | Resin 1 | Resin 2 | Peak loss modulus (° C.) | Peak Tan delta (° C.) |
|---|---|---|---|---|
| EX-8 | PE-7 | IBOMA | 2 | 121 |
| EX-47 | PE-32 | CHMA | 0 | 73 |
| CE-9 | PE-4 | IBOMA | 44 | 129 |
| EX-44 | PE-32 | AdMA | 5 | 117 |
| EX-87 | PE-32 | PEMA | −7 | 31 |
| CE-2 | PE-32 | EHMA | −21 | 26 |
| EX-51 | PE-22 | IBOA | −14 | 67 |
| CE-4 | Exothane 10 | IBOMA | 31 | 124 |

Additive Manufacturing of Formulated Resins

Unless otherwise noted, all 3D-printed examples were manufactured either on an Asiga Pico 2 HD or Asiga Max, a vat polymerization 3D printer available from Asiga USA, Anaheim Hills, CA Each formulation listed in Tables 39-42 was photopolymerized on an Asiga 3D printer with a LED light source of 385 nm. Tensile test bars of Type V according to ASTM D638-14 (2014) and DMA 3-point bend test specimens were manufactured. The resin bath of the printer was heated to 35-50° C. before photopolymerization to reduce the viscosity to be able to manufacture the tensile test bars. The following settings were used for the printing: slice thickness=50 μm; burn in layers=1; separation velocity=1.5 mm/s, separation distance=10 mm, approach velocity=1.5 mm/s. On the Asiga Pico 2 HD, 1 slide per layer was used at a speed of 7 mm/min. In addition, Table 43 describes the printer type, and the exposure time, burn-in time, and temperature used for printing the formulations indicated in Tables 39-42. The printed parts were washed using propylene carbonate followed by isopropanol to remove unreacted resin. The printed part was then post-cured using Asiga Pico Flash post-curing chamber for 90 minutes on each side (except for EX-189, which was post-cured using a Clearstone CA320UV LED curing chamber for 5 minutes on each side), followed by heating in an oven at 100° C. for 30 minutes. The dogbone specimens were conditioned in phosphate-buffered saline (PBS, 1×, pH=7.4) for 24 hours at 37° C. The DMA 3-point bend test specimens were conditioned in DI water for 48 hours at room temperature.

TABLE 39

Example formulations for additive manufacturing (amounts in parts by weight)

| Component | EX-56 | EX-57 | EX-58 | EX-59 | EX-60 |
|---|---|---|---|---|---|
| PE-43 | 50 | | | | |
| PE-44 | | 50 | 50 | 50 | |
| PE-32 | | | | | 50 |
| IBOMA | 50 | 50 | 50 | 50 | 50 |
| TPO | 2 | 2 | 0.5 | 0.5 | |
| BHT | 0.025 | 0.025 | 0.025 | 0.025 | 0.025 |
| Omnirad 379 | | | | | 0.75 |
| NapA | 0.025 | 0.025 | 0.1 | | 0.0175 |
| Tinuvin 326 | | | | 0.025 | |

TABLE 40

Example formulations for additive manufacturing (amounts in parts by weight)

| Component | EX-61 | EX-62 | EX-63 | EX-64 | EX-65 | EX-66 | EX-67 |
|---|---|---|---|---|---|---|---|
| PE-7 | 47 | | | | | | |
| PE-5 | | 44 | | | | | |
| PE-6 | | | 50 | | | | |

TABLE 40-continued

Example formulations for additive manufacturing (amounts in parts by weight)

| Component | EX-61 | EX-62 | EX-63 | EX-64 | EX-65 | EX-66 | EX-67 |
|---|---|---|---|---|---|---|---|
| PE-37 | | | | 50 | | | |
| PE-25 | | | | | 25 | | |
| PE-13 | | | | | 25 | 25 | 20 |
| PE-19 | | | | | | 25 | 30 |
| IBOMA | 53 | 56 | 50 | 50 | 50 | 50 | 50 |
| TPO | 2 | 2 | 2 | 2 | 2 | 2 | 2 |
| BHT | 0.025 | 0.025 | 0.025 | 0.025 | 0.025 | 0.025 | 0.025 |
| NapA | 0.025 | 0.025 | 0.025 | 0.025 | 0.025 | 0.025 | 0.025 |

TABLE 41

Example formulations for additive manufacturing (amounts in parts by weight)

| Component | EX-68 | EX-69 | EX-70 | EX-71 | EX-72 | EX-73 | EX-74 |
|---|---|---|---|---|---|---|---|
| PE-19 | 50 | | | | | | |
| PE-44 | | 49.42 | 45.22 | 44.69 | 44.16 | 39.96 | |
| PE-33 | | 5.58 | 9.78 | 7.81 | 5.84 | 10.04 | 5 |
| PE-13 | | | | | | | 45 |
| IBOMA | 40 | 45 | 45 | 47.5 | 50 | 50 | 50 |
| HDDMA | 10 | | | | | | |
| TPO | 0.5 | 2 | 2 | 2 | 2 | 2 | 2 |
| BHT | 0.025 | 0.025 | 0.025 | 0.025 | 0.025 | 0.025 | 0.025 |
| NapA | 0.1 | 0.025 | 0.025 | 0.025 | 0.025 | 0.025 | 0.025 |

TABLE 42

Example formulations for additive manufacturing (amounts in parts by weight)

| Component | EX-75 | EX-76 | EX-77 | EX-78 | EX-86 | EX-188 | EX-189 |
|---|---|---|---|---|---|---|---|
| PE-19 | 50 | | | | | | |
| PE-32 | | 50 | | | | | |
| PE-13 | | | 50 | | | | |
| PE-30 | | | | 40 | | | |
| PE-14 | | | | 10 | | | |
| PE-47 | | | | | 50 | | |
| PE-25 | | | | | | 50 | |
| PE-86 | | | | | | 5 | |
| PE-56 | | | | | | | 50 |
| DiCPMA | 50 | | | | | | |
| AdMA | | 50 | 50 | 50 | | | |
| IBOMA | | | | | 50 | | 50 |
| BnMA | | | | | | 45 | |
| TPO | 2 | 2 | 2 | 2 | 2 | 2 | 2 |
| BHT | 0.025 | 0.025 | 0.025 | 0.025 | 0.025 | 0.025 | 0.025 |
| NapA | 0.025 | 0.025 | 0.025 | 0.025 | | | |
| Tinuvin 326 | | | | | 0.025 | 0.025 | 0.025 |

TABLE 43

Additive manufacturing conditions.

| Example | Printer | Exposure Time (sec) | Burn-in Time (sec) | Temperature (° C.) |
|---|---|---|---|---|
| EX-56 | Asiga Pico 2 HD | 2.25 | 15 | 50 |
| EX-57 | Asiga Max | 3 | 10 | 40 |
| EX-58 | Asiga Max | 5 | 10 | 40 |
| EX-59 | Asiga Pico 2 HD | 3.75 | 20 | 50 |
| EX-60 | Asiga Max | 4.5 | 10 | 40 |
| EX-61 | Asiga Pico 2 HD | 2 | 8 | 50 |
| EX-62 | Asiga Pico 2 HD | 2.5 | 8 | 50 |
| EX-63 | Asiga Max | 2.5 | 10 | 40 |
| EX-64 | Asiga Pico 2 HD | 2 | 8 | 50 |
| EX-65 | Asiga Pico 2 HD | 2 | 8 | 50 |
| EX-66 | Asiga Max | 3 | 10 | 40 |
| EX-67 | Asiga Pico 2 HD | 2 | 8 | 50 |
| EX-68 | Asiga Pico 2 HD | 2 | 8 | 50 |
| EX-69 | Asiga Max | 3 | 10 | 40 |
| EX-70 | Asiga Max | 3 | 10 | 40 |
| EX-71 | Asiga Max | 3 | 10 | 40 |

TABLE 43-continued

Additive manufacturing conditions.

| Example | Printer | Exposure Time (sec) | Burn-in Time (sec) | Temperature (° C.) |
|---|---|---|---|---|
| EX-72 | Asiga Max | 3 | 10 | 40 |
| EX-73 | Asiga Max | 3 | 10 | 40 |
| EX-74 | Asiga Pico 2 HD | 2 | 8 | 50 |
| EX-75 | Asiga Pico 2 HD | 2 | 8 | 50 |
| EX-76 | Asiga Pico 2 HD | 2 | 8 | 50 |
| EX-77 | Asiga Pico 2 HD | 2 | 8 | 50 |
| EX-78 | Asiga Pico 2 HD | 2 | 8 | 50 |
| EX-86 | Asiga Max | 5 | 10 | 40 |
| EX-188 | Asiga Max | 3.25 | 8 | 40 |
| EX-189 | Asiga Max | 6 | 20 | 40 |

General Procedure for Tensile Testing

PBS conditioned dogbones were tested on an Instron 5944 (Instron, Norwood, MA) with a 500 N load cell. The test speed was 5 mm/minute and the initial grip separation was 1 inch (2.5 cm). The gauge length was set to 1 inch (2.5 cm). Five replicate samples for each formulation were tested, and the average value are reported. The tensile strength at yield was determined according to ASTM D638-14 (2014) and shown in Table 44 and Table 45 below. For specimens that did not yield, maximum tensile strength was determined. Elongation at break was determined from the crosshead movement of the grips.

General Procedure for the Determination of Relaxation Modulus Using Dynamic Mechanical Analysis Rectangular specimens were water conditioned by soaking in deionized water for 48 hours at room temperature at 22 to 25° C. and were tested in a TA Q800 DMA equipped with a submersion 3-point bending clamp. The water conditioned rectangular specimens were placed in water filled submersion fixture. The specimens were equilibrated for 10 minutes at 37° C., followed by applying a 2% strain. Relaxation modulus was measured for 30 minutes using TA Advantage software, and is reported in Tables 44 and 45.

TABLE 44

Yield strength, elongation and relaxation modulus of cast formulations.

| Sample | Strength at Yield (MPa) | Elongation at Break (%) | Initial Relaxation Modulus (MPa) | Relaxation Modulus at 30 Minutes (MPa) | Percent Loss of Relaxation Modulus After 30 Minutes |
|---|---|---|---|---|---|
| CE-1 | 1.3* | 5.8 | N.M1 | N.M1 | N.M1 |
| CE-2 | 2.9* | 87.7 | N.M1 | N.M1 | N.M1 |
| CE-3 | 1.2* | 32.0 | N.M1 | N.M1 | N.M1 |
| CE-4 | 46.9 | 2.9 | 1662.0 | 712.5 | 57.1 |
| CE-5 | 26.1 | 9.3 | 1027.0 | 265.8 | 74.1 |
| CE-6 | 15.2 | 122.7 | 401.5 | 51.2 | 87.2 |
| CE-7 | 15.7* | 1.0 | N.M2 | N.M2 | N.M2 |
| CE-8 | 29.3* | 1.7 | N.M2 | N.M2 | N.M2 |
| CE-9 | 64.8* | 2.8 | 2829.0 | 1859.0 | 34.3 |
| EX-1 | 56.2 | 7.6 | 1442.0 | 720.9 | 50.0 |
| EX-2 | 42.0 | 12.9 | 798.4 | 313.4 | 60.7 |
| EX-3 | 28.7 | 84.2 | 594.3 | 212.9 | 64.2 |
| EX-4 | 30.7 | 38.9 | 794.8 | 312.4 | 60.7 |
| EX-5 | 22.1 | 80.8 | 540.8 | 214.2 | 60.4 |
| EX-6 | 17.6 | 113.9 | 498.5 | 198.8 | 60.1 |
| EX-7 | 39.1 | 17.1 | 1213.0 | 545.1 | 55.1 |
| EX-42 | 39.7 | 16.5 | 1096.0 | 557.9 | 49.1 |
| EX-43 | 17.4 | 92.7 | 438.1 | 84.1 | 80.8 |
| EX-9 | 22.2 | 36.4 | 632.3 | 174.3 | 72.4 |
| EX-10 | 20.2 | 90.3 | 565.6 | 182.2 | 67.8 |
| EX-11 | 22.5 | 70.0 | 740.8 | 219.8 | 70.3 |
| EX-12 | 14.7 | 75.8 | 500.1 | 143.2 | 71.4 |

TABLE 44-continued

Yield strength, elongation and relaxation modulus of cast formulations.

| Sample | Strength at Yield (MPa) | Elongation at Break (%) | Initial Relaxation Modulus (MPa) | Relaxation Modulus at 30 Minutes (MPa) | Percent Loss of Relaxation Modulus After 30 Minutes |
|---|---|---|---|---|---|
| EX-13 | 27.7 | 46.3 | 922.2 | 365.7 | 60.3 |
| EX-14 | 28.5 | 46.7 | 867.1 | 380.8 | 56.1 |
| EX-15 | 23.1 | 90.7 | 655.8 | 258.5 | 60.6 |
| EX-16 | 38.3 | 12.2 | 949.6 | 458.8 | 51.7 |
| EX-50 | 17.2 | 64.1 | 263.4 | 17.6 | 93.3 |
| EX-17 | 26.8 | 44.7 | 763.1 | 219.6 | 71.2 |
| EX-18 | 21.1 | 65.5 | 498.0 | 147.6 | 70.4 |
| EX-19 | 23.5 | 15.5 | 772.8 | 295.0 | 61.8 |
| EX-20 | 35.5 | 25.1 | 1020.0 | 434.7 | 57.4 |
| EX-21 | 33.2 | 30.9 | 977.7 | 391.6 | 59.9 |
| EX-24 | 27.3 | 66.6 | 780.3 | 287.9 | 63.1 |
| EX-23 | 32.9 | 54.9 | 1173.0 | 397.1 | 66.1 |
| EX-22 | 30.4 | 48.0 | 859.1 | 368.4 | 57.1 |
| EX-44 | 33.3 | 27.5 | 837.5 | 325.0 | 61.2 |
| EX-45 | 21.5 | 67.9 | 369.7 | 71.9 | 80.6 |
| EX-41 | 32.8 | 35.2 | 808.1 | 229.3 | 71.6 |
| EX-46 | 16.6 | 66.6 | 345.8 | 73.6 | 78.7 |
| EX-47 | 14.0 | 125.6 | 169.0 | 13.9 | 91.8 |
| EX-29 | 28.4 | 37.8 | 746.3 | 267.7 | 64.1 |
| EX-28 | 29.0 | 34.7 | 879.7 | 362.3 | 58.8 |
| EX-26 | 30.8 | 47.5 | 824.4 | 366.9 | 55.4 |
| EX-27 | 37.8 | 12.5 | 985.1 | 476.6 | 51.6 |
| EX-31 | 24.1 | 63.7 | 612.6 | 201.5 | 67.1 |
| EX-32 | 24.7 | 58.1 | 602.8 | 197.0 | 67.3 |
| EX-33 | 26.8 | 53.9 | 691.4 | 246.8 | 64.3 |
| EX-34 | 26.3 | 57.1 | 577.6 | 172.8 | 70.1 |
| EX-35 | 27.8 | 53.0 | 698.4 | 220.0 | 68.5 |
| EX-36 | 34.4 | 28.4 | 882.6 | 327.2 | 62.9 |
| EX-25 | 28.7 | 56.3 | 738.1 | 285.1 | 61.4 |
| EX-30 | 23.3 | 51.0 | 458.0 | 109.0 | 76.2 |
| EX-48 | 24.1 | 28.2 | 591.9 | 177.3 | 70.0 |
| EX-37 | 30.0 | 29.2 | 691.0 | 251.7 | 63.6 |
| EX-38 | 24.6 | 66.0 | 640.6 | 196.0 | 69.4 |
| EX-39 | 32.8 | 30.5 | 916.3 | 410.2 | 55.2 |
| EX-40 | 21.3 | 66.2 | 570.5 | 156.7 | 72.5 |
| EX-8 | 26.9 | 54.4 | 765.0 | 264.7 | 65.4 |
| EX-49 | 22.2* | 75.5 | 261.1 | 56.1 | 78.5 |
| Eχ-52 | 27.8 | 63.4 | 749.0 | 282.4 | 62.3 |
| Eχ-53 | 25.1 | 53.0 | 636.2 | 236.1 | 62.9 |
| Eχ-54 | 27.9 | 53.5 | 761.9 | 264.1 | 65.3 |
| Eχ-55 | 26.1 | 49.9 | 746.3 | 258.6 | 65.3 |
| Eχ-51 | 18.8* | 101.0 | 121.1 | 20.5 | 83.1 |
| Eχ-79 | 35.0 | 14.9 | 1051.0 | 457.8 | 56.4 |
| Eχ-80 | 19.6* | 28.5 | 486.0 | 190.0 | 60.9 |
| Eχ-81 | 30.1 | 33.3 | 891.0 | 369.7 | 58.5 |
| Eχ-82 | 32.7 | 24.2 | 924.5 | 441.3 | 52.3 |
| Eχ-83 | 26.3 | 50.2 | 741.5 | 335.4 | 54.8 |
| Eχ-84 | 29.7 | 30.4 | 649.4 | 311.8 | 52.0 |
| Eχ-85 | 16.6 | 66.6 | 345.8 | 73.6 | 78.7 |
| Eχ-90 | 20.1 | 22.7 | 423.8 | 50.7 | 88.1 |
| Eχ-91 | 49.5 | 25.9 | 406.8 | 48.9 | 88.0 |
| Eχ-92 | 22.0 | 55.1 | 447.3 | 100.0 | 77.7 |
| Eχ-93 | 33.7 | 22.1 | 698.8 | 210.5 | 69.9 |
| Eχ-94 | 22.2 | 42.8 | 604.7 | 149.1 | 75.3 |
| Eχ-95 | 32.3 | 23.7 | 863.2 | 287.3 | 66.7 |
| Eχ-96 | 29.4 | 20.1 | 795.2 | 273.5 | 65.6 |
| Eχ-97 | 29.1 | 22.7 | 750.6 | 213.9 | 71.5 |
| Eχ-98 | 24.5 | 48.1 | 531.0 | 130.9 | 75.4 |
| Eχ-99 | 21.6 | 37.2 | 373.3 | 40.4 | 89.2 |
| Eχ-100 | 24.6 | 51.9 | 530.2 | 142.5 | 73.1 |
| Eχ-101 | 23.9 | 57.7 | 558.8 | 129.7 | 76.8 |
| Eχ-102 | 20.1 | 65.3 | 502.6 | 114.2 | 77.3 |
| Eχ-103 | 22.0 | 40.9 | 537.5 | 109.3 | 79.7 |
| Eχ-104 | 18.9 | 67.7 | 369.6 | 97.2 | 73.7 |
| Eχ-105 | 27.1 | 42.4 | 722.0 | 262.8 | 63.6 |
| Eχ-106 | 24.4 | 46.9 | 519.2 | 137.5 | 73.5 |
| Eχ-107 | 21.6 | 75.8 | 496.6 | 110.2 | 77.8 |
| Eχ-108 | 22.2 | 63.0 | 541.0 | 115.2 | 78.7 |
| Eχ-109 | 25.5 | 40.0 | 639.9 | 173.9 | 72.8 |
| Eχ-110 | 24.2 | 33.6 | 483.9 | 124.3 | 74.3 |
| Eχ-111 | 17.4 | 33.8 | 263.4 | 21.7 | 91.8 |
| Eχ-112 | 24.6 | 25.7 | 642.3 | 194.6 | 69.7 |

TABLE 44-continued

Yield strength, elongation and relaxation modulus of cast formulations.

| Sample | Strength at Yield (MPa) | Elongation at Break (%) | Initial Relaxation Modulus (MPa) | Relaxation Modulus at 30 Minutes (MPa) | Percent Loss of Relaxation Modulus After 30 Minutes |
|---|---|---|---|---|---|
| EX-113 | 20.4 | 42.8 | 568.5 | 182.2 | 68.0 |
| EX-114 | 29.3 | 58.3 | 665.2 | 178.6 | 73.2 |
| EX-115 | 17.3 | 120.3 | 450.8 | 128.3 | 71.5 |
| EX-116 | 29.8 | 41.1 | 699.2 | 191.8 | 72.6 |
| EX-117 | 29.5 | 23.1 | 732.1 | 243.8 | 66.7 |
| EX-118 | 17.3 | 35.5 | 405.5 | 90.1 | 77.8 |
| EX-119 | 14.8 | 74.7 | 323.2 | 58.3 | 82.0 |
| EX-120 | 11.3 | 119.7 | 233.6 | 35.7 | 84.7 |
| EX-121 | 17.5 | 83.4 | 356.4 | 73.8 | 79.3 |
| EX-122 | 35.1 | 62.4 | 776.8 | 300.8 | 61.3 |
| EX-123 | 31.3 | 76.2 | 648.3 | 237.2 | 63.4 |
| EX-124 | 24.6 | 62.3 | 614.1 | 214.0 | 65.2 |
| EX-125 | 27.8 | 53.0 | 698.4 | 220.0 | 68.5 |
| EX-126 | 34.4 | 28.4 | 882.6 | 327.2 | 62.9 |
| EX-127 | 20.6 | 45.4 | 436.2 | 68.3 | 84.3 |
| EX-128 | 27.7 | 53.8 | 649.1 | 170.5 | 73.7 |
| EX-129 | 26.6 | 29.0 | 529.0 | 156.1 | 70.5 |
| EX-130 | 39.4 | 26.1 | 1113.0 | 471.6 | 57.6 |
| EX-131 | 27.8 | 37.6 | 776.9 | 269.9 | 65.3 |
| EX-132 | 21.5 | 43.7 | 501.7 | 113.3 | 77.4 |
| EX-133 | 29.3 | 45.1 | 763.2 | 226.7 | 70.3 |
| EX-134 | 27.5 | 27.5 | 588.6 | 165.8 | 71.8 |
| EX-135 | 28.2 | 32.3 | 649.8 | 214.4 | 67.0 |
| EX-136 | 23.5 | 27.1 | 477.9 | 99.0 | 79.3 |
| EX-137 | 29.7 | 34.7 | 779.5 | 230.4 | 70.4 |
| EX-138 | 21.7 | 40.1 | 491.5 | 70.1 | 85.7 |
| EX-139 | 28.4 | 38.7 | 723.0 | 224.9 | 68.9 |
| EX-140 | 28.0 | 37.5 | 759.1 | 220.7 | 70.9 |
| EX-141 | 30.7 | 41.1 | 713.6 | 257.9 | 63.9 |
| EX-142 | 29.8 | 66.2 | 769.8 | 260.1 | 66.2 |
| EX-143 | 24.8 | 40.9 | 661.9 | 144.0 | 78.3 |
| EX-144 | 35.4 | 30.4 | 1131.0 | 492.7 | 56.4 |
| EX-145 | 25.4 | 55.1 | 716.9 | 212.2 | 70.4 |
| EX-146 | 26.3 | 20.1 | 1075.0 | 465.3 | 56.7 |
| EX-147 | 36.3 | 29.6 | 937.9 | 370.9 | 60.5 |
| EX-148 | 22.9 | 41.6 | 555.9 | 145.6 | 73.8 |
| EX-149 | 18.4 | 31.4 | 299.5 | 31.2 | 89.6 |
| EX-150 | 23.5 | 45.8 | 629.3 | 164.5 | 73.9 |
| EX-151 | 27.6 | 58.5 | 795.0 | 303.0 | 61.9 |
| EX-152 | 23.0 | 70.9 | 736.4 | 263.5 | 64.2 |
| EX-153 | 35.8 | 34.9 | 903.0 | 286.7 | 68.3 |
| EX-154 | 25.4 | 47.4 | 596.8 | 198.1 | 66.8 |
| EX-155 | 30.9 | 26.4 | 932.2 | 385.0 | 58.7 |
| EX-156 | 28.5 | 27.7 | 846.2 | 311.1 | 63.2 |
| EX-157 | 21.0 | 55.1 | 642.2 | 245.9 | 61.7 |
| EX-158 | 41.5 | 28.4 | 1166.1 | 550.0 | 52.8 |
| EX-159 | 22.6* | 48.9 | 370.3 | 94.1 | 74.6 |
| EX-160 | 21.1 | 22.9 | 518.8 | 125.1 | 75.9 |
| EX-161 | 21.5 | 60.5 | 560.8 | 171.8 | 69.4 |
| EX-162 | 34.1 | 71.2 | 789.2 | 329.5 | 58.3 |
| EX-163 | 23.7 | 75.2 | 573.0 | 155.4 | 72.9 |
| EX-164 | 25.7 | 38.9 | 729.0 | 235.2 | 67.7 |
| EX-165 | 27.7 | 54.2 | 764.0 | 277.6 | 63.7 |
| EX-166 | 12.0 | 109.9 | 181.3 | 14.6 | 91.9 |
| EX-167 | 17.5 | 122.8 | 178.1 | 17.2 | 90.4 |
| EX-168 | 18.0 | 27.3 | 166.5 | 13.5 | 91.9 |
| EX-169 | 20.7 | 36.2 | 121.3 | 11.3 | 90.7 |
| EX-170 | 20.4 | 50.5 | 138.8 | 10.1 | 92.7 |
| EX-171 | 20.0 | 38.6 | 124.3 | 12.6 | 89.9 |
| EX-172 | 16.8 | 83.5 | 138.8 | 8.5 | 93.9 |
| EX-173 | 20.6 | 48.4 | 198.3 | 12.1 | 93.9 |
| EX-174 | 24.7 | 60.7 | 272.5 | 12.8 | 95.3 |
| EX-175 | 27.6 | 33.2 | 424.4 | 34.5 | 91.9 |
| EX-176 | 26.6 | 66.6 | 486.2 | 74.5 | 84.7 |
| EX-177 | 16.6 | 91.9 | 316.7 | 21.7 | 93.1 |
| EX-178 | 14.1 | 105.8 | 153.9 | 9.4 | 93.9 |
| EX-179 | 36.0 | 23.3 | 926.9 | 346.3 | 62.6 |
| EX-180 | 49.7 | 11.1 | 1188.0 | 312.7 | 73.7 |
| EX-181 | 18.0* | 57.4 | 156.5 | 13.2 | 91.58 |
| EX-182 | 17.8* | 38.5 | 296.5 | 68.5 | 76.90 |
| EX-183 | 20.1* | 59.7 | 105.8 | 13.7 | 87.02 |
| EX-184 | 17.1* | 37.1 | 161.7 | 15.9 | 90.16 |
| EX-185 | 28.4* | 74.0 | 338.2 | 82.8 | 75.52 |
| EX-186 | 19.5* | 48.4 | 312.3 | 79.4 | 74.59 |
| EX-187 | 20.4* | 59.8 | 227.7 | 28.5 | 87.48 |
| EX-87 | 9.3* | 167.5 | N.M1 | N.M1 | N.M1 |
| EX-88 | 8.6* | 181.1 | N.M1 | N.M1 | N.M1 |
| EX-89 | 25.2* | 130.9 | 106.2 | 17.2 | 83.8 |

N.M1. Not measured since these samples were very flexible and soft, and couldn't be successfully clamped for DMA testing.
N.M2. Not measured since these specimens were very brittle.
*maximum tensile strength is reported for specimens that did not have a distinct yield point.

TABLE 45

Yield strength, elongation and relaxation modulus of printed formulations.

| Sample | Strength at Yield (MPa) | Elongation at Break (%) | Initial Relaxation Modulus (MPa) | Relaxation Modulus at 30 Minutes (MPa) | Percent Loss of Relaxation Modulus After 30 Minutes |
|---|---|---|---|---|---|
| EX-56 | 24.1 | 91.2 | 536.0 | 187.6 | 65.0 |
| EX-57 | 25.0 | 103.0 | 722.5 | 252.7 | 65.0 |
| EX-58 | 21.6 | 83.8 | 666.1 | 227.7 | 65.8 |
| EX-59 | 21.9 | 126.4 | 612.7 | 194.4 | 68.3 |
| EX-60 | 23.8 | 93.2 | 675.7 | 226.5 | 66.5 |
| EX-61 | 28.3 | 96.7 | 857.5 | 325.0 | 62.1 |
| EX-62 | 36.5 | 24.7 | 1175.0 | 460.1 | 60.8 |
| EX-63 | 29.0 | 76.4 | 710.8 | 277.7 | 60.9 |
| EX-64 | 27.1 | 126.0 | 805.2 | 303.4 | 62.3 |
| EX-65 | 31.3 | 70.4 | 978.2 | 383.7 | 60.8 |
| EX-66 | 25.0 | 111.1 | 406.3 | 157.2 | 61.3 |
| EX-67 | 29.4 | 75.0 | 879.5 | 368.8 | 58.1 |
| EX-68 | 24.2 | 32.8 | 620.9 | 211.2 | 66.0 |
| EX-69 | 26.7 | 65.5 | 696.4 | 249.4 | 64.2 |
| EX-70 | 35.6 | 41.2 | 1007.0 | 436.1 | 56.7 |
| EX-71 | 35.7 | 43.5 | 983.0 | 441.2 | 55.1 |
| EX-72 | 36.6 | 42.9 | 925.3 | 413.6 | 55.3 |
| EX-73 | 43.7 | 20.6 | 1199.0 | 564.8 | 52.9 |
| EX-74 | 23.8 | 98.7 | 649.0 | 261.8 | 59.7 |
| EX-75 | 28.9 | 74.7 | 800.3 | 249.1 | 68.9 |
| EX-76 | 30.3 | 88.7 | 789.4 | 288.3 | 63.5 |
| EX-77 | 22.7 | 144.9 | 738.1 | 285.1 | 61.4 |
| EX-78 | 27.6 | 95.9 | 707.1 | 265.0 | 62.5 |
| EX-86 | 28.9 | 28.3 | 715.4 | 322.7 | 54.9 |
| EX-188 | 29.4 | 96.5 | 828.6 | 322.0 | 61.1 |
| EX-189 | 18.0 | 62.8 | 109.8 | 8.7 | 92.1 |

Additive Manufacturing of Aligner Articles from the Formulated Resin

The formulation of EX-57 was photopolymerized on the Asiga Max printer with a LED light source of 385 nm. A stereolithography file format (STL file) of the aligner was loaded into the Asiga Composer software, and support structures were generated. The resin bath of the printer was heated to 40° C. before photopolymerization to reduce the viscosity to be able to manufacture the article. The following settings were used for the printing: slice thickness=50 m; burn in layers=1; separation velocity=1.5 mm/min, burn-in exposure time=10 sec; exposure time=3 sec. The printed part was washed using propylene carbonate followed by isopropanol to remove unreacted resin. The printed specimen was then post-cured using an Asiga Pico Flash post-curing chamber for 90 minutes on each side. The photopolymerized aligners fit the models, showing precision of the additive manufacture part. The aligner had acceptable strength and flexibility.

Test Procedure for Gravimetric Analysis of Extractable from Printed Articles

Articles shaped as a continuous 5-tooth row (30.4 mm×9.24 mm×8.17 mm) using formulations of EX-57 and EX-58 were printed and post processed according to the procedure described above. The thickness of the article was 0.49 mm. 3×5-tooth articles (total surface area of 45 cm$^2$) were placed in a 40 mL glass vial and weighed. 15 mL of solvent (either heptane or 5% ethanol/Milli-Q water) was added to the vial, with one 15 mL blank (vial without articles) for each solvent. The vials were covered with TEFLON caps, and the samples were kept at 37° C. for 24 hours while shaking at 80 RPM in a LabLine Bench top incubated shaker Model 4628. The samples were allowed to cool before transferring the extraction solution to a new 20 mL glass vial. A 5 mL aliquot was transferred to a pre-weighed 8 mL glass vial and set to evaporate under a nitrogen purge. The vials were weighed once the solvent dried off, until a constant weight was reached. % Residue was calculated using the following formula shown below. The test was completed in triplicates, all run at the same time, and result shown is the average of the three replicates.

$$\% \text{ Residue} = \left[ \frac{\substack{\text{(Vial after evaporation(g)} - \\ \text{Vial tare (g))} * 15 \text{ mL solvent}}}{\substack{\text{Mass of article (g)} * \\ 5 \text{ mL solvent analyzed}}} \right] * 100$$

TABLE 46

| Sample | % Extractable in Heptane | % Extractable in 5% EtOH/H$_2$O |
|---|---|---|
| EX-57 | 0.444 | 0.129 |
| EX-58 | 0.280 | 0.072 |

Antimicrobial Testing:
Preparation of Formulated Resins:

The formulations shown in Table 47 were prepared according to the General Procedure for Formulation Preparation method.

General Procedure of Formulation Casting and Curing

Each formulation listed in Table 47 was coated between two sheets of silicone treated PET films having a thickness of 0.03 mm (0.001 inches) using a knife coater having a 500 microns knife gap set by a feeler gauge. The coated films were cured with four passes under a 600 Watt/inch Fusion D bulb at 90 feet per minute (fpm), with normally 6000 milliwatts per square centimeter (mW/cm$^2$) irradiation per pass, and approximately 600 millijoule per square centimeter (mJ/cm$^2$) irradiation energy per pass using a LH-10 Curing system equipped with a DRS-10 conveyer from Heraeus Noblelight America LLC (Gaithersburg, MD). The films were then kept in an oven set at 100° C. for 30 minutes.

Additive Manufacturing of 3D Printed Sheets

Each formulation listed in Table 47 was photopolymerized on an Asiga Max 3D printer (vat polymerization 3D printer available from Asiga USA, Anaheim Hills, CA) with a LED light source of 385 nanometer (nm) to generate sheets of dimension 120 mm×60 mm×0.5 mm. The following settings were used for the printing: slice thickness=50 micrometers (µm); burn in layers=1; separation velocity=1.5 millimeters per second (mm/s), separation distance=10 millimeters (mm), approach velocity=1.5 mm/s. The printed parts were washed using propylene carbonate followed by isopropanol to remove unreacted resin. The printed part was then post-cured using a Clearstone 3200 UV chamber (365 nm, 385 nm, 405 nm LEDs-all of them switched on) for 5 minutes each side under nitrogen purge. The parts were then heated in an oven at 100° C. for 30 minutes.

Media Preparation: Brain Heart Infusion (BHI) broth was prepared as directed on the manufacturer's label by dissolving 37 g/L in deionized water and filter sterilizing the solution using 500-mL Nalgene Rapid-Flow sterile bottle top filters, 0.2 µm PES membrane.

Bacterial Culture: An overnight culture of *Streptococcus mutans* (ATCC® 25175) was grown by using a sterile, serological pipet to scrape and transfer a small amount of a 25% glycerol freezer stock of the microorganism to a 15-mL conical tube containing 5 mL of BHI. The tube was incubated at 37° C. under static (non-shaking) conditions for 12-16 hours. Two 1-mL aliquots of the overnight culture were centrifuged at 5000×g for 5 minutes to pellet the cells, the supernatant was removed from each and the bacteria in each tube were resuspended in 1 mL of phosphate buffered saline (PBS; pH 7.4). The 1 mL of PBS containing *S. mutans* from one tube was then transferred to a 15-mL conical vial and diluted with PBS to a final volume of 10 mL. The resulting solution was used as the PBS inoculum. The remaining 1 mL of bacteria was transferred to a 15-mL conical vial containing 9 mL of 2.22 wt. % monolaurin (ML), so that the final concentration of the solution was 2 wt. % ML. The ML solution was prepared by dissolving 1 g of ML in 2 mL of DMSO, then diluting into PBS so that the final concentration in the inoculum was 2%.

Sample Preparation: A 20-mm diameter circular hollow punch was used to cut out individual discs. The discs were removed from the punch and transferred to a sterile 6-well plate (Falcon Polystyrene Microplates obtained from Thermo Fisher Scientific, Hampton, NH). Two discs were placed in each well. The following samples were prepared for testing:

Sample Inoculation and Incubation: Samples were inoculated by pipetting 100 microliters of the corresponding inoculation solution (in PBS or in 2% ML) onto one of the 20 mm discs in each well. The second disc in each well was then placed on top of the inoculum on the first disc, sandwiching the inoculum between the two film samples. After inoculation, half of the 6-well plates were placed inside a ZIPLOC bag containing a paper towel saturated with molecular biology grade water (Fisher BioReagents) and moved to 37° C. incubator (Nor-Lake Scientific, Hudson, WI) for a 24 hour static incubation. The other half of the samples were harvested immediately for quantitative recovery at the 0 hour time point. All samples were prepared in triplicate.

Sample recovery: Each sample was transferred to an individual 50-mL conical vial containing 10 mL of PBS buffer containing 0.05% Tween 20. Each tube was vortexed for 1 minute, then sonicated for 30 seconds (2 second pulses with 0.5 seconds between pulses, at level 3 on Misonix Sonicator Ultrasonic Processor XL), then vortexed for 1 minute. After the second vortexing step, each tube was serially diluted in Butterfield's buffer to the −6 dilution (the original tube served as the −1 dilution) and 1 mL from each dilution was plated on 3M Aerobic Count PetriFilm. The PetriFilm was sealed in an air tight anaerobic box with two BD GasPak EZ pouches (BD GasPak EZ Anaerobe Container System with Indicator) and placed in an incubator at 37° C. for 24 hours. The number of colony forming units (CFU) on each plate were counted after the 24 hour incubation using a 3M PetriFilm reader. The procedure described above was adapted from the Japanese Industrial Standard (JIS) Z 2801 2000 (E) (Antimicrobial products—Test for antimicrobial activity and efficacy) and was modified to decrease the disc size and sandwich the inoculum between two discs.

TABLE 47

Formulations (amounts in parts by weight)

|  | EX-190 | EX-191 |
|---|---|---|
| PE-76 | 50 | 50 |
| IBOMA | 50 | 50 |
| TPO | 2 | 2 |
| BHT | 0.025 | 0.025 |
| Tinuvin 326 | 0.025 | 0.025 |
| Monolaurin |  | 2 |

TABLE 48

| | | 0 hours | | 24 hours | | Log10 | |
|---|---|---|---|---|---|---|---|
| | | | Log10 | | Log10 | | |
| Formulation | Description | Average CFU Recovered | Log10 Standard Deviation | Log10 Average CFU | Log10 Standard Deviation | reduction after 24 h incubation | Notes |
| PBS inoculum solution | Inoculation Control | 6.89 | n/a | 6.00 | n/a | 0.89 | Slight reduction |
| 2% ML inoculum solution | Inoculation Control | 6.88 | n/a | 0.00 | n/a | 6.88 | Full kill |
| S. mutans in DMSO | Inoculation Control | 6.88 | n/a | 6.08 | n/a | 0.80 | Slight reduction |
| EX-191 | Cast | 6.79 | 0.12 | 4.58 | 1.08 | 2.21 | Reduction |
| EX-191 | Cast + 2% ML solution | 6.55 | 0.20 | 0.00 | 0.00 | 6.55 | Full kill |
| EX-190 | Cast | 6.61 | 0.12 | 0.00 | 0.00 | 6.61 | Full kill |
| EX-191 | Printed | 6.75 | 0.11 | 5.32 | 0.18 | 1.43 | Reduction |
| EX-191 | Printed + 2% ML solution | 6.96 | 0.01 | 0.72 | 1.24 | 6.24 | Full kill |
| EX-190 | Printed | 6.81 | 0.02 | 0.00 | 0.00 | 6.81 | Full kill |

As the data denotes, some viability was lost during the 24 hour period for the samples lacking ML. These are labeled as either "slight reduction" (less than one log 10) or "reduction" (~1-2 log 10). The slight reduction and reduction observed in controls is not considered to be due to antimicrobial properties of the sample.

All of the patents and patent applications mentioned above are hereby expressly incorporated by reference. The embodiments described above are illustrative of the present invention and other constructions are also possible. Accordingly, the present invention should not be deemed limited to the embodiments described in detail above and shown in the accompanying drawings, but instead only by a fair scope of the claims that follow along with their equivalents.

The invention claimed is:

1. An orthodontic article comprising the reaction product of a polymerizable composition comprising:
   30-65 parts by weight of monofunctional (meth)acrylate monomer(s) per 100 parts of the total polymerizable composition, wherein a cured homopolymer of at least one monofunctional (meth)acrylate monomer has a $T_g$ of 30 degrees Celsius (° C.) or greater, at least 40, 50, 60, 70, 80, or 90° C.; and
   at least one urethane (meth)acrylate comprising polymerized units of an aliphatic polycarbonate diol, wherein the at least one urethane (meth)acrylate comprises a reaction product of at least one of the following:
   i) an aliphatic polycarbonate diol, a diisocyanate, a diol (meth)acrylate, and a hydroxy functional (meth)acrylate;
   ii) an aliphatic polycarbonate diol and an isocyanate functional (meth)acrylate;
   iii) an aliphatic polycarbonate diol, a diisocyanate, and an isocyanate functional (meth)acrylate; or
   iv) an aliphatic polycarbonate diol, a diisocyanate, a diol (meth)acrylate, and an isocyanate functional (meth) acrylate.

2. The orthodontic article of claim 1, wherein the monofunctional (meth)acrylate monomer(s) having a $T_g$ of at least 30° C. has a log P value of greater than 1, 1.5, 2, 2.5, or 3.

3. The orthodontic article of claim 1, wherein the at least one urethane (meth)acrylate comprises the reaction product of an aliphatic polycarbonate diol, a diisocyanate, and a hydroxy functional (meth)acrylate.

4. The orthodontic article of claim 3, wherein the hydroxy functional (meth)acrylate is of Formula (II):

wherein Q is a polyvalent organic linking group and A is a (meth)acryl functional group of the formula —XC(=O)C($R_1$)=$CH_2$, wherein X is O, S, or $NR_4$, $R_4$ is H or alkyl of 1 to 4 carbon atoms, $R_1$ is a lower alkyl of 1 to 4 carbon atoms or H, and p is 1 or 2.

5. The orthodontic article of claim 3, wherein the at least one urethane (meth)acrylate is of Formula (VI):

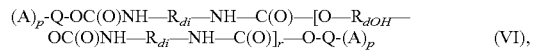

wherein A has the formula —XC(=O)C($R_1$)=$CH_2$, wherein X is O, S, or $NR_4$, $R_4$ is H or alkyl of 1 to 4 carbon atoms, and $R_1$ is a lower alkyl of 1 to 4 carbon atoms or H, p is 1 or 2, Q is a polyvalent organic linking group, $R_{di}$ is the residue of a diisocyanate, $R_{dOH}$ is the residue of a polycarbonate polyol, and r averages from 1 to 15.

6. The orthodontic article of claim 1, wherein the at least one urethane (meth)acrylate comprises the reaction product of an aliphatic polycarbonate diol, a diisocyanate, a diol (meth)acrylate, and a hydroxy functional (meth)acrylate.

7. The orthodontic article of claim 6, wherein the at least one urethane (meth)acrylate is of Formula (V):

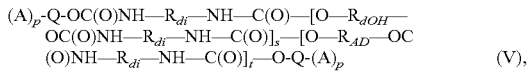

(V), wherein A has the formula $-XC(=O)C(R_1)=CH_2$, wherein X is O, S, or $NR_4$, $R_4$ is H or alkyl of 1 to 4 carbon atoms, and $R_1$ is a lower alkyl of 1 to 4 carbon atoms or H, p is 1 or 2, Q is a polyvalent organic linking group, $R_{di}$ is the residue of a diisocyanate, $R_{dOH}$ is the residue of a polycarbonate polyol, s and t are independently 1 or greater, and s+t averages from 2 to 15, wherein the s and t units may be connected to each other in any order, wherein $R_{AD}$ is the residue of a (meth)acrylated diol.

8. The orthodontic article of claim 1, wherein the at least one urethane (meth)acrylate comprises the reaction product of an aliphatic polycarbonate diol and an isocyanate functional (meth)acrylate.

9. The orthodontic article of claim 8, wherein the at least one urethane (meth)acrylate is of Formula (VIII):

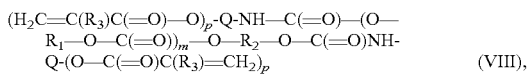

(VIII), wherein Q is a polyvalent organic linking group, $R_3$ is a lower alkyl of 1 to 4 carbon atoms or H, p is 1 or 2, each $R_1$ and $R_2$ are independently an aliphatic, cycloaliphatic, or aliphatic/cycloaliphatic alkylene group and an average number of carbon atoms in a combination of all the $R_1$ and $R_2$ groups is 4 to 10, and m is 2 to 23.

10. The orthodontic article of claim 1, wherein the at least one urethane (meth)acrylate comprises the reaction product of an aliphatic polycarbonate diol, a diisocyanate, and an isocyanate functional (meth)acrylate.

11. The orthodontic article of claim 10, wherein the at least one urethane (meth)acrylate is of Formula (XI):

(XI), wherein u is 0 to 15, A has the formula $-XC(=O)C(R_1)=CH_2$, wherein X is O, S, or $NR_4$, $R_4$ is H or alkyl of 1 to 4 carbon atoms, and $R_1$ is a lower alkyl of 1 to 4 carbon atoms or H, p is 1 or 2, Q is a polyvalent organic linking group, $R_{di}$ is the residue of a diisocyanate, and $R_{dOH}$ is the residue of a polycarbonate polyol.

12. The orthodontic article of claim 1, wherein the at least one urethane (meth)acrylate comprises the reaction product of an aliphatic polycarbonate diol, a diisocyanate, a diol (meth)acrylate, and an isocyanate functional (meth)acrylate.

13. The orthodontic article of claim 12, wherein the at least one urethane (meth)acrylate is of Formula (XII):

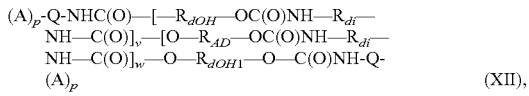

(XII), wherein, $R_{di}$ is the residue of a diisocyanate, $R_{AD}$ is the residue of a (meth)acrylated diol, Q is a polyvalent organic linking group, A has the formula $-XC(=O)C(R_1)=CH_2$, wherein X is O, S, or $NR_4$, $R_4$ is H or alkyl of 1 to 4 carbon atoms, and $R_1$ is a lower alkyl of 1 to 4 carbon atoms or H, p is 1 or 2, v+w is 1 to 15, and $R_{dOH1}$ is selected from $R_{dOH}$ or $R_{AD}$, with the provisos that if v is 0 then $R_{dOH1}$ is $R_{dOH}$, and if w is 0 then $R_{dOH1}$ is $R_{AD}$.

14. The orthodontic article of claim 1, wherein the urethane (meth)acrylate further comprises polymerized units of a polyester diol, wherein the urethane (meth)acrylate contains the same or more polymerized units of the aliphatic polycarbonate diol than the polyester diol.

15. The orthodontic article of claim 14, wherein the at least one urethane (meth)acrylate is of Formula (XIII):

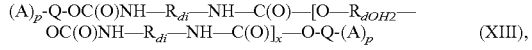

(XIII), wherein Q is a polyvalent organic linking group, A is a (meth)acryl functional group of the formula $-XC(=O)C(R_1)=CH_2$, wherein X is O, S, or $NR_4$, $R_4$ is H or alkyl of 1 to 4 carbon atoms, $R_1$ is a lower alkyl of 1 to 4 carbon atoms or H, and wherein p is 1 or 2, $R_{di}$ is the residue of a diisocyanate, and each $R_{dOH2}$ is independently selected from the residue of a polyester polyol or the residue of a polycarbonate polyol, with the proviso that x is greater than 2.

16. The orthodontic article of claim 1, wherein the aliphatic polycarbonate diol is of Formula (I):

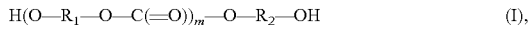

(I), wherein each of $R_1$ in each $(O-R_1-O-C(=O))$ repeat unit and each $R_2$ are independently an aliphatic, cycloaliphatic, or aliphatic/cycloaliphatic alkylene group and an average number of carbon atoms in a combination of all the $R_1$ and $R_2$ groups is 4 to 10, and m is 2 to 23.

17. The orthodontic article of claim 1, wherein the polymerizable composition further comprises an antimicrobial lipid in an amount of 0.1 wt. % or greater, 0.5 wt. %, 1 wt. %, 1.5 wt. %, 2 wt. %, 3 wt. %, or 4 wt. % or greater, based on the total weight of the polymerizable composition, and 20 wt. % or less, 15 wt. %, 12 wt. %, 10 wt. %, 8 wt. %, or 5 wt. % or less, based on the total weight of the polymerizable composition.

18. The orthodontic article of claim 17, wherein the antimicrobial lipid comprises monolaurin.

19. The orthodontic article of claim 1, wherein the polymerizable composition is polymerized and the polymerized composition exhibits an elongation at break of 15% or greater and a tensile strength at yield of at least 10 MPa as determined according to ASTM D638-14 after conditioning in phosphate-buffered saline having a pH of 7.4, for 24 hours at a temperature of 37° C.

20. The orthodontic article of claim 1, wherein the polymerizable composition is polymerized and the polymerized composition exhibits a 3-point bend modulus of at least 100 MPa as determined according to dynamic mechanical analysis at 2% strain after conditioning in deionized water at 20-25° C. for 48 hours.

21. The orthodontic article of claim 1, wherein the orthodontic article is an orthodontic alignment tray.

22. A method comprising:
a) obtaining a photopolymerizable composition comprising:
30-65 parts by weight of monofunctional (meth)acrylate monomer(s) per 100 parts of the total polymerizable composition, wherein a cured homopolymer of at least one monofunctional (meth)acrylate monomer has a $T_g$ of 30° C. or greater; and
at least one urethane (meth)acrylate comprising polymerized units of an aliphatic polycarbonate diol, wherein the at least one urethane (meth)acrylate comprises a reaction product of at least one of the following:
i) an aliphatic polycarbonate diol, a diisocyanate, a diol (meth)acrylate, and a hydroxy functional (meth)acrylate;

ii) an aliphatic polycarbonate diol and an isocyanate functional (meth)acrylate;

iii) an aliphatic polycarbonate diol, a diisocyanate, and an isocyanate functional (meth)acrylate; or iv) an aliphatic polycarbonate diol, a diisocyanate, a diol (meth)acrylate, and an isocyanate functional (meth)acrylate;

b) selectively curing the photopolymerizable composition; and c) repeating steps a) and b) to form multiple layers and create the orthodontic article.

23. A non-transitory machine readable medium comprising data representing a three-dimensional model of an orthodontic article, when accessed by one or more processors interfacing with a 3D printer, causes the 3D printer to create an orthodontic article comprising a reaction product of a photopolymerizable composition comprising a blend of:

30-65 parts by weight of monofunctional (meth)acrylate monomer(s) per 100 parts of the total polymerizable composition, wherein a cured homopolymer of at least one monofunctional (meth)acrylate monomer has a $T_g$ of 30° C. or greater; and at least one urethane (meth)acrylate comprising polymerized units of an aliphatic polycarbonate diol, wherein the at least one urethane (meth)acrylate comprises a reaction product of at least one of the following:

i) an aliphatic polycarbonate diol, a diisocyanate, a diol (meth)acrylate, and a hydroxy functional (meth)acrylate;

ii) an aliphatic polycarbonate diol and an isocyanate functional (meth)acrylate;

iii) an aliphatic polycarbonate diol, a diisocyanate, and an isocyanate functional (meth)acrylate; or iv) an aliphatic polycarbonate diol, a diisocyanate, a diol (meth)acrylate, and an isocyanate functional (meth)acrylate.

24. A method comprising:

a) receiving, by a manufacturing device having one or more processors, a digital object comprising data specifying a plurality of layers of an orthodontic article; and b) generating, with the manufacturing device by an additive manufacturing process, the orthodontic article based on the digital object, the orthodontic article comprising a reaction product of a photopolymerizable composition, the photopolymerizable composition comprising a blend of:

30-65 parts by weight of monofunctional (meth)acrylate monomer(s) per 100 parts of the total polymerizable composition, wherein a cured homopolymer of at least one monofunctional (meth)acrylate monomer has a $T_g$ of 30° C. or greater; and at least one urethane (meth)acrylate comprising polymerized units of an aliphatic polycarbonate diol, wherein the at least one urethane (meth)acrylate comprises a reaction product of at least one of the following:

i) an aliphatic polycarbonate diol, a diisocyanate, a diol (meth)acrylate, and a hydroxy functional (meth)acrylate;

ii) an aliphatic polycarbonate diol and an isocyanate functional (meth)acrylate;

iii) an aliphatic polycarbonate diol, a diisocyanate, and an isocyanate functional (meth)acrylate; or iv) an aliphatic polycarbonate diol, a diisocyanate, a diol (meth)acrylate, and an isocyanate functional (meth)acrylate.

* * * * *